United States Patent
Vitti

(10) Patent No.: US 12,123,022 B2
(45) Date of Patent: *Oct. 22, 2024

(54) MESENCHYMAL STEM CELL COMPOSITIONS AND METHODS OF MAKING

(71) Applicant: Vitti Labs, Liberty, MO (US)

(72) Inventor: Philipp Vitti, Kansas City, MO (US)

(73) Assignee: Vitti Labs, Liberty, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/162,557

(22) Filed: Jan. 31, 2023

(65) Prior Publication Data

US 2023/0250395 A1 Aug. 10, 2023

Related U.S. Application Data

(63) Continuation of application No. 17/968,631, filed on Oct. 18, 2022, which is a continuation-in-part of application No. 17/085,695, filed on Oct. 30, 2020.

(51) Int. Cl.
*C12N 5/0775* (2010.01)

(52) U.S. Cl.
CPC ........ *C12N 5/0662* (2013.01); *C12N 2501/10* (2013.01); *C12N 2501/90* (2013.01); *C12N 2501/998* (2013.01)

(58) Field of Classification Search
None
See application file for complete search history.

(56) References Cited

U.S. PATENT DOCUMENTS

| | | |
|---|---|---|
| 11,359,058 B2 | 6/2022 | Gao et al. |
| 2015/0125950 A1 | 5/2015 | Lim et al. |
| 2019/0134101 A1 | 5/2019 | Braid et al. |
| 2020/0281983 A1 | 9/2020 | Mitsialis et al. |
| 2020/0283715 A1 | 9/2020 | Andriolo et al. |

FOREIGN PATENT DOCUMENTS

| | | |
|---|---|---|
| WO | 2016196774 A1 | 12/2016 |
| WO | 2017214707 A1 | 12/2017 |
| WO | 2018199603 A1 | 11/2018 |

OTHER PUBLICATIONS

Kim et al. "Cyclic tangential flow filtration system for isolation of extracellular vesicles" (2021), APL Bioengineering, vol. 5, 016103, 1-10. (Year: 2021).*
Davies & Rafiq "Considerations for the bioprocessing, manufacture and translation of extracellular vesicles for therapeutic and diagnostic applications" (2017), Cell Gene Ther Insights, 3(6): 683-694. (Year: 2017).*
Wang et al. "Bioloigcal conduits combining bone marrow mesenchymal stem cells and extracellular matrix to treat long-segment sciatic nerve defects" (2015) Neural Regen Res, 10(6): 965-971. (Year: 2015).*
Hassan et al. "Allogeneic cell therapy bioprocess economics and optimization: downstream processing decisions" (2015), REgen Med., 10(5): 591-609. (Year: 2015).*
Haraszti et al. "Exosomes Produced from 3D Cultures of MSCs by Tangential Flow Filtration Show Higher Yield and Improved Activity" (2018), Molecular Therapy, vol. 26, No. 12: 2838-2847. (Year: 2018).*
Cunha et al. "Filtration methoodolgies for the clarification and concentration of human mesenchymal stem cells" (2015), J Membrane Sci, vol. 478: 117-129. (Year: 2015).*
Haraszti, R. A. et al., "Exosomes Produced from 3D Cultures of MSCs by Tangential Flow Filtration Show Higher Yield and Improved Activity," Molecular Therapy, vol. 26, No. 12, Dec. 2018, pp. 2838-2847.
Busatto, S. et al., "Tangential Flow Filtration for Highly Efficient Concentration of Extracellular Vesicles from Large Volumes of Fluid", Cells 2018, 7, pp. 1-11.
Zhang, B. et al., "Mesenchymal Stem Cells Secrete Immunologically Active Exosomes," Stem Cells and Development, vol. 23, No. 11, Jun. 1, 2014.
Harrell, C. R. et al. "Therapeutic Potential of Mesenchymal Stem Cell-Derived Exosomes in the Treatment of Eye Diseases", Cell Biology and Translational Medicine, vol. 2, pp. 47-57.
Kim, Y. et al. "Conditioned media from human umbilical cord blood-derived mesenchymal stem cells stimulate rejuvenation function in human skin", Biochemistry and Biophysics Reports 16, accepted Oct. 9, 2018, pp. 96-102.
Joe, A. et al., "Mesenchymal stem cells and potential applications in treating ocular disease", Current Eye Research vol. 35, No. 11, Nov. 2010, pp. 941-952.

* cited by examiner

*Primary Examiner* — Teresa E Knight
(74) *Attorney, Agent, or Firm* — Polsinelli PC

(57) ABSTRACT

Disclosures herein are directed to first compositions comprising exosomes and extracellular matrix components and their use thereof. Also described are methods and kits wherein these first compositions are packaged and used with second compositions comprising mesenchymal stem cells. The first and second compositions are derived from the same tissue source using tangential flow filtration.

13 Claims, 1 Drawing Sheet

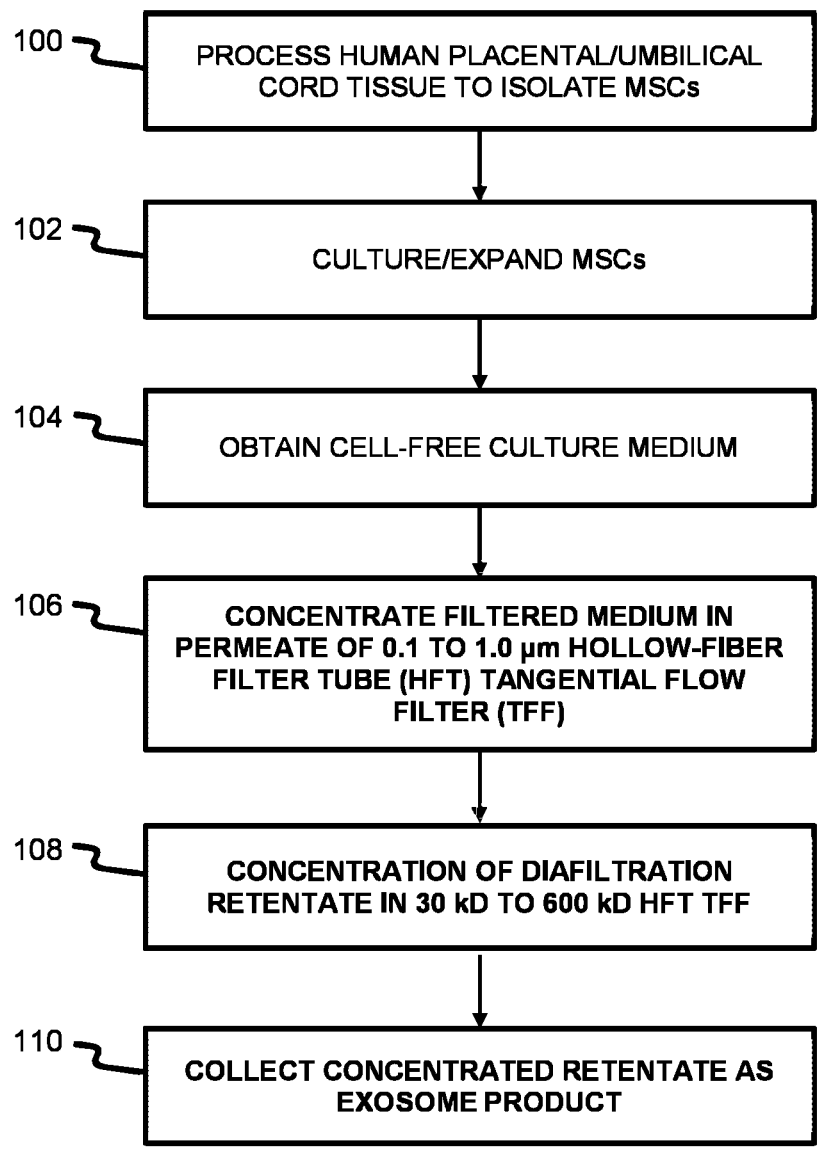

MESENCHYMAL STEM CELL COMPOSITIONS AND METHODS OF MAKING

CROSS-REFERENCE TO RELATED APPLICATIONS

This application is a continuation of U.S. application Ser. No. 17/968,631 which is a continuation in part that claims benefit to U.S. application Ser. No. 17/085,695, filed Oct. 30, 2020, each of which are incorporated herein by reference in their entirety for all purposes.

BACKGROUND

1. Field

The present invention relates to compositions comprising exosomes and extracellular matrix components and the use thereof.

2. Discussion of Related Art

Mesenchymal stem cells (MSCs) are highly proliferative, multipotent cells that can be isolated from tissues including umbilical cord, placenta, bone marrow, and fat and can differentiate into mesenchymal cell with negligible risk of teratoma formation. These cells secrete exosomes which are nano particles or extracellular vesicles of about 30 nm to −250 nm in diameter. Exosomes carry proteins, lipids, and nucleic acids (miRNA mRNA, ssDNA), loads from the cell, and as such, perform a functional role that mediates paracrine signaling, cellular-cell communication, trophic factor regulation and immunomodulation. They are also thought to play a role as biomarkers of certain disease models. Because exosomes are a form of "natural' drug delivery, and do not elicit acute immune rejection, they can be loaded ex vivo with certain therapeutic agents and targeted to deliver their therapeutic loads to specific cell types. In addition to exosomes, there are components normally encapsulated in an extracellular matrix (e.g., growth factors, signaling molecules) that can be useful as therapeutics. However, it is difficult to concentrate these components and isolate them from an intact cell culture and tissue sample. As an example, these useful components are often discarded in supernatant fractions when exosomes are prepared and purified using centrifugation.

Thus, methods of obtaining preparations of exosomes and components from that are homogenous, intact, free of contaminants, and concentrated enough to provide commercially viable and therapeutic yields are still needed.

SUMMARY

Various aspects of the present disclosure are directed to method for preparing compositions comprising mesenchymal stem cells or exosomes.

In certain aspects, a method for preparing an MSC composition is provided, the method comprising: (a) culturing mesenchymal stem cells (MSCs) in a culture media; (b) collecting the mesenchymal stem cells from the culture in an MSC fraction further comprising exosomes, extracellular matrix colonies, and fragments thereof, and (c) filtering the MSC fraction through a first section of a tangential flow filtration system to obtain a retentate comprising the mesenchymal stem cells, wherein the retentate is the MSC composition.

In various aspects, the method of preparing an MSC composition does not comprise ultra-centrifugation. In other aspects, the first section of the tangential flow filtration system can comprise a filter having a pore size of about 0.5 to 1 microns.

In various aspects, the method of preparing an MSC composition further comprises obtaining the mesenchymal stem cells from a tissue sample. In some instances, the tissue sample may comprise umbilical cord blood, placental tissue, umbilical cord tissue, adipose tissue, bone marrow, skin, ocular tissue, or teeth.

Further aspects of the present disclosure provide for a method for preparing an exosome composition, the method comprising: (a) culturing mesenchymal stem cells in a culture media; (b) collecting the culture media as a first fraction and collecting the mesenchymal stem cells as a second fraction, the second fraction further comprising exosomes and extracellular matrix colonies and fragments thereof, (c) filtering the second fraction through a first section of a tangential flow filtration system to obtain a first permeate comprising the exosomes and the extracellular matrix colonies and fragments thereof, (d) filtering the first permeate through a second section of the tangential flow filtration system to generate a second permeate comprising exosomes and at least one extracellular matrix component, (e) combining the second permeate with the first fraction collected in step (b) to form a third fraction; and (0 collecting the third fraction as the exosome composition.

In certain aspects, step (a) can further comprise culturing the mesenchymal stem cells for a time sufficient to generate a conditioned media and step (b) comprises collecting the conditioned media as the first fraction.

In any of the above and related aspects, the method of preparing an exosome composition does not comprise ultra-centrifugation.

In various aspects, the first section of the tangential flow filtration system comprises a filter having a pore size of about 0.5 to 1 micron and/or the second section of the tangential flow filtration system comprises a filter having a pore size of about 50 kD to about 500 kD.

In various aspects, the method of preparing an exosome composition further comprises obtaining the mesenchymal stem cells from a tissue sample. In various aspects, the tissue sample can comprise umbilical cord blood, placental tissue, umbilical cord tissue, adipose tissue, bone marrow, skin, ocular tissue, or teeth.

In various aspects, the method of preparing an exosome composition provided herein can further comprise filtering the third fraction through a third section of the tangential flow filtration system to form a third permeate and collecting the third permeate as the exosome composition. In various aspects, the third section of the tangential flow filtration system may comprise a filter having a pore size of about 200 to 800 kD.

In certain aspects, the method of preparing an exosome composition as provided herein further comprises filtering the third filtrate through a fourth section of the tangential flow filtration system to form a fourth permeate and collecting the fourth permeate as the exosome composition. In various aspects, the fourth section of the tangential flow filtration system can comprise a filter having a pore size of about 50 to 100 kD.

Various aspects of the present disclosure are also directed to an MSC composition as prepared according to a method described herein. Likewise, additional aspects of the present disclosure are directed to an exosome composition prepared according to any method described herein.

In further aspects, a kit is also provided, the kit comprising (a) an MSC composition prepared according to any method described herein and/or (b) an exosome composition prepared according to any method described herein In various aspects, a method of treating a subject in need thereof is also provided, the method comprising administering (a) an MSC composition prepared according to a method described herein and (b) an exosome composition prepared according to a method herein to the subject.

Still further aspect of the present disclosure are directed to methods of preparing an MSC composition and an exosome composition, the method comprising (a) culturing mesenchymal stem cells in a culture media; (b) collecting the culture media as a first fraction and collecting the mesenchymal stem cells as a second fraction, the second fraction further comprising exosomes and extracellular matrix colonies and fragments thereof; (c) filtering the second fraction through a first section of a tangential flow filtration system to obtain a first permeate comprising the exosomes, the extracellular matrix colonies and fragments thereof and a retentate comprising the mesenchymal stem cells; (d) collecting the retentate as the MSC composition; (e) filtering the first permeate through a second section of the tangential flow filtration system to generate a second permeate comprising exosomes and at least one extracellular matrix component; (f) combining the second permeate with the first fraction collected in step (b) to generate a third fraction; and (f) collecting the third fraction as the exosome composition.

The foregoing and other objects of the present disclosure, the various features thereof, as well as the disclosure itself may be more fully understood from the following description, when read together with the accompanying drawings in which:

BRIEF DESCRIPTION OF THE DRAWINGS

The foregoing and other objects of the present disclosure, the various features thereof, as well as the disclosure itself may be more fully understood from the following description, when read together with the accompanying drawing in which:

FIG. 1 is a flow chart delineating the steps (bolded) of the method according to one embodiment of the disclosure.

DETAILED DESCRIPTION

In various aspects, the present disclosure is directed to therapeutic compositions comprising at least one exosome (e.g., as isolated from a mesenchymal stem cell), and at least one extracellular matrix component (ECM component) wherein the composition does not comprise an intact extracellular matrix. Methods of preparing these therapeutic compositions and exemplary therapeutic uses are also provided herein.

I. Compositions

In one aspect of the disclosure, an exosome composition is provided comprising at least one exosome isolated from a mesenchymal stem cell, and at least one component isolated from an extracellular matrix (e.g., an "ECM component"). In another aspect of the disclosure, an MSC composition is provided comprising at least one mesenchymal stem cell, wherein the MSC composition is free of any extracellular matrix or fragments thereof. Advantageously, the exosome compositions herein do not comprise any intact extracellular matrix (for example, ECM that is in contact with the mesenchymal stem cell). Also advantageously, the present compositions derive their therapeutic benefits without genomic modifications (e.g., without incorporating gene edited cells) and without subjecting the mesenchymal stem cells to stressful conditions (e.g., hypoxia). In various aspects, the exosome composition and the MSC composition provided herein are each prepared from a single tissue sample using a process comprising tandem tangential flow filtration.

Mesenchymal Stem Cells

Mesenchymal stem cells (MSCs) are highly proliferative, multipotent cells that can be isolated from umbilical cord tissue or blood, placental tissues, bone marrow, skin, and fat and can differentiate into mesenchymal cells with negligible risk of teratoma formation. These cells secrete exosomes which are nanoparticles or extracellular vesicles of about 30 nm to 250 nm in diameter.

Extracellular Matrix

The extracellular matrix (ECM) is secreted by cells and surrounds them in tissues. Its purpose is to be the structural support for cells since its characteristics determine the characteristics of the tissue (bone compared to cartilage to organs). ECM is not passive mechanical support for cells. It in fact an incredibly complex scaffold composed of a variety of biologically active molecules that are highly regulated and critical for determining the action and fate of the cells that it surrounds.

ECM proteins (growth factors, cytokines, peptides, poly peptides etc. . . . ) play crucial and complex roles during cell surface receptor signaling. ECM serves as a reservoir for growth factors, allowing for their local release and association with their canonical receptors. Many ECM proteins have binding sites for both cell adhesion and growth factors, allowing local concentration of the growth factors near to their cell surface receptors and cell adhesion sites. This localization of growth factors, and thus their signaling, by the ECM probably contributes to the establishment of gradients of the soluble, diffusible growth factor morphogens, which play vital roles in patterning in developmental processes.

The two basic constructs of the Extracellular Matrix are the basement membrane and the interstitial matrix. The basement membrane encompasses the ECM between and around the epithelial and stromal layers of cells. The ECM is produced by epithelial cells and stromal cells found within the matrix itself, including fibroblasts, osteoblasts, and basal epithelial cells. It provides mechanical structure, separates different cell types and signals for cell differentiation, migration and survival. The ECM also provides much of the structural support available to parenchymal cells in tissues. This provides tensile strength and flexibility. The interstitial matrix is a type of extracellular matrix found in between various animal cells in the intercellular space. It is characterized by the presence of fibronectins and types I, III, V, VI, VII and XII collagens. ECM surrounding cells forms a porous 3D lattice and the interstitial matrix acts as a compression buffer against stress placed on the ECM.

The ECM is a complex mixture of proteins and glycosoaminoglycans (negatively charged polysaccharides) and generally contains three categories of materials: (a) glyocosaminoglycans and their proteoglycans which resist compressive forces, (b) adhesive glycoproteins and (c) fibrous proteins that provide tensile strength. Each are described further below.

(a) Glycosaminoglycans (GAGs).

Glycosaminoglycans (GAGs) are linear polysaccharides composed of two basic saccharides: an amino sugar and an uronic acid. The origin of the ECM determines the carbohydrate chain and the other chemical modifications that determine their specificity and functionality. GAGs were originally primarily known for being "space fillers" in the ECM. More recently they have been shown to be active signaling molecules whose roles in a variety of cellular processes (including cytokine production, leukocyte recruitment and inflammatory response) are important for controlling cell fate. There are four classes of glycosaminoglycans: (1) hyaluronan, (2) chondroitin sulfate (CS)/dermatan sulfate (DS), (3) heparan sulfate (HS)/heparin, and (4) keratan sulfate (KS). Hyaluronan is a naturally occurring biopolymer possessing numerous functions within the body including wound facilitation, cell migration, and cell signaling. Hyaluronan is an extremely versatile material with various unique properties. Commonly excreted by cells such as fibroblasts and chondrocytes, Hyaluronan is an important part of the extracellular matrix and also functions in cell signaling and wound repair8. Hyaluronan is composed of multiple negatively charged hyaluronic acid subunits, allowing it to attract and retain water. The binding of water provides support to the extracellular matrix and allows for compressibility and tensile strength. The other GAGs are chondroitin sulfate (CS), dermatan sulfate (DS), keratan sulfate (KS), and heparan sulfate (HS). These four GAGS are typically covalently attached to proteins to form proteoglycans.

Related to glycosaminoglycans are proteoglycans. A proteoglycan is composed of a core protein with one or more covalently attached GAGs. They are stored in secretory granules, inserted into the plasma membrane or secreted into the ECM.

(b) Adhesive Glycoproteins

Various adhesive glycoproteins are included in extracellular matrices—including laminin, fibronectin and integrins, described below.

Laminin. Laminins are the most abundant glycoproteins of the basement membrane extracellular matrix (ECM) and can be found in almost all tissues of the body. Laminin is composed of α, β, and γ chains of which there are 5 α, 4 β, and 6 γ chains. It has a cross-like structure with 3 short arms and 1 long arm. The α chains possess a large globular domain known as the G domain at the C-termini. Laminin, as a key component of the basement membrane extracellular matrix (ECM), regulates tissue morphogenesis. Laminin supports growth and differentiation of many cell types including epithelial, endothelial, neural, muscle and organ cells. They play essential roles in the establishment of tissue architecture and stability and provide cells with a structural scaffold. As such, laminins are involved in a variety of biological processes ranging from tissue survival, angiogenesis[13], and neural development, to skin re-epithelialization and wound healing. Laminins have been shown to regulate core cellular activities, such as adhesion, apoptosis, proliferation, migration, and differentiation.

Fibronectin. Fibronectin (FBN) is a high-molecular weight glycoprotein of the extracellular matrix. FBN is an ECM component that, through binding integrin receptors of the cell surface, acts as a key player of the communication between the intra and the extracellular environment, thus controlling cell behavior. It binds collagen, heparin, other fibronectin proteins, and cell surface integrins. Fibronectin binds integrins through the tri-peptide motif of arginine, glycine, and aspartic acid.

Integrins. Integrins are the main cell adhesion receptors involved in focal adhesion formation and are required for cell migration. Cells respond to the mechanical and biochemical changes in ECM through the crosstalk between integrins and the actin cytoskeleton. Integrins are heterodimeric transmembrane receptors composed of eighteen a subunits and eight b subunits that can be non-covalently assembled into 24 combinations. The integrin dimers bind to an array of different ECM molecules with overlapping binding affinities. Therefore, the specific integrin expression patterns by a cell dictate which ECM substrate the cell can bind and the composition of integrin adhesomes determines the downstream signaling events, thus the eventual cell behavior and fate. Integrins have unique ability to respond to the molecular composition and physical properties of the ECM and integrate both mechanical and chemical signals through direct association with the cytoskeleton, which also determines the selection of specific integrin species to be involved.

(c) Fibrous Proteins

ECM further comprises various fibrous proteins that provide tensile strength. Exemplary fibrous proteins are collagen and elastin, discussed below.

Collagens. Collagens are the major structural component of the ECM. Collagens provide scaffolding for the attachment of laminin, proteoglycans and cell surface receptors. Twenty-eight types of collagens (I-XXVIII) with multiple sub types have been identified so far in the ECM. Collagens play structural roles and contribute to mechanical properties, organization, and shape of tissues. They interact with cells via several receptor families and regulate their proliferation, migration, and differentiation. Collagens are deposited in the extracellular matrix where most of them form supramolecular assemblies (e.g., fibrillar, fibril-associated, beaded filament, network-forming, or transmembrane collagens). Fibrillar assemblies, formed from types I, II, III, V, XI, XXIV, and XXVII collagens, are the most comment type of assemblies—accounting for 90% of the collagen in the body and concentrated in healthy bone, skin, tendons, ligaments and cartilage. Fibril-associated (FACIT) collagens (IX, XII, XIV, XVI, XIX, XX, XXI, XXII) do not form fibrils, but do attach to fibril forming collagens. This group is thought to serve as molecular bridges important for organization and stability of extracellular matrices. They reinforce and make dense connective tissues, bones, tendons, joints and ligaments. Beaded filament (VI) collagen maintains regularity in muscle function and stabilizes the cell membrane. Network-forming (IV, VIII and X) form net-like structures such as the basement membrane and interact with anchoring fibrils (type VII) which link the basement membrane to collagen and laminin in the ECM. This group is essential for providing a scaffold for assembly and mechanical stability but are also important in cell adhesion, migration, survival, proliferation and differentiation. Finally, transmembrane collagens (XIII, XVII, XXIII, XXV) have a function role in cell adhesion, differentiation, tissue development and structural integrity. Accordingly, collagens may be understood to exist in a monomer or fragmented state and also in supramolecular assemblies which may or may not include fibrils.

Elastin provides elasticity to the ECM. It is produced as tropoelastin, a 72 kDa precursor protein that is secreted from the cell. In the extracellular space it crosslinks with other elastin molecules to form sheets and fibers. Elastin is a key ECM protein that provides resilience and elasticity to tissues and organs. Elastin is roughly 1000 times more flexible than collagens thus providing for its function to increase the elasticity of tissues. This is critical for organs and tissues that require elastic recoil and flexibility.

In addition to these large structural components, the extracellular matrix also contains various factors (growth factors or cytokines), signaling molecules, nucleic acids, lipids, and extra cellular vesicles (e.g., exosomes) that are valuable for cell signaling and that may be useful in various therapeutics. In various aspects of the present disclosure, it is desirable to obtain these structural components and these growth factors/signaling molecules and vesicles and isolate them from the extracellular matrix.

In various aspects, the exosome composition provided herein can comprise one or more exosomes and one or more components isolated from an extracellular matrix (e.g., one or more of the components listed above, each of which are referred to herein as an "ECM component"). The exosome composition described herein are prepared from a single tissue sample using tangential flow filtration, and preferably tandem tangential flow filtration.

In still further aspects, the exosome compositions may comprise one or more component isolated from an extracellular matrix (ECM component). In various aspects, the one or more ECM component may comprise a glycosaminoglycan or proteoglycan thereof, an adhesive glycoprotein, a fibrous protein, and a growth factor.

In various aspects, the one or more ECM component may comprise a glycosaminoglycan. In some aspects, the glycosaminoglycan is selected from the group consisting of hyaluronan, chondroitin sulfate (CS), dermatan sulfate (DS), keratan sulfate (KS), and heparan sulfate (HS), or any proteoglycan thereof.

In various aspects, the one or more ECM component may comprise an adhesive glycoprotein. In various aspects, the adhesive glycoprotein is selected from the group consisting of Laminin, Fibronectin, tenascin, and nidogen.

In various aspects, the one the one or more ECM component may comprise a fibrous protein. The fibrous protein may, in some aspects, be selected from the group consisting of collagens and elastin.

In various aspects, the one or more ECM component may comprise a growth factor. Suitable growth factors that may be included in the exosome composition include, but are not limited to EGF, Endothelin, Eotaxin/CCL11, FGF-4, GDF-15, ICAM-1, IGFBP-1, IL-6, PDGF-AA, TGF-beta 3, TIMP-1, TIMP-2, BCAM, Smad 4, CD 163, CD30 Ligand, TNFSF8, and Integrin b1.

In various aspects, the one or more ECM component may be selected from any one of Cysteine-rich Protein 1, PIM2, Cadherin-13, Beta IG-H3, EG-VEGF/PK1, Cyclophilin A, Dkk-3, BMP-3, QDPR, PAM, EDAR, EGF R/ErbB1, ALCAM, CXCR3, SBP-1, BCMA/TNFRSF17, CCL28/VIC, IL-29, HSP47, VE-Cadherin, 1-309, TGF-beta RIII, CCR8, Fractalkine, TCN1, RSU1, uPAR, VEGF-D, PRELP, TGF-beta RII, Thrombopoietin (TPO), Endothelin, S100A6, Angiogenin, TIMP-4, MSP alpha Chain, Activin A, DMGDH, Serpin B8, TRAIL R3/TNFRSF10C, CFHR5, Caspase-14, PRDX 1, FGF-12, CXCR5/BLR-1, Semaphorin 7A, SPINK7, NT-4, TNF RH/TNFRSF1B, 6Ckine, SerRS, Angiostatin, Angiopoietin-like Factor, B7-1/CD80, Protein C, Tcf20, TROY/TNFRSF19, EMAP-II, CSH1, TLR4, RPLPO, ErbB3, RPL11, PGK-1, FGF-16, Plakophilin 1, PRCP, RAGE, Insulin, TSR2, NT-3, USP14, VDAC1/Porin, Proteasome 20S a+b, M-CSF, IL-2, ICAM-1, NEDD8, PRG2, Insulysin/IDE, ICAM-2, MMP-1, Salivary alpha amylase/aAmylase, IL-17F, Galectin-1, Lymphotoxin beta/TNFSF3, TBCA, PREP, VAP-A, Utrophin, YB1, VAP-1, CFHR4, FGF-20, Cyclophilin B, RNASE4, SBSN, FGF R4, FGF-17, PGLS-C-t, Eotaxin-3/CCL26, RREB1, TMEM223, ADAMTS-15, Semenogelin II/SEMG2, C3a, RPL12, GDF8, IGF-II, RPS25, Follistatin-like 1, Smad 5, Notch-2, 1-TAC/CXCL11, TRANCE, MMP-3, uPA, WDR1, UQCRB, DR6/TNFRSF21, BMP-15, PSMA4, ErbB4, Gephyrin, beta-NGF, BMP-2, BMP-6, NAP-2, LECT2, FGF-13 1B, Reg3A, CD14, SHIP, RPL5, VEGF, IL-1 F5/FIL1 delta, RPS28, TUBA6, Endostatin, MMP-9, CK-MB, CapG, IL-11, Ribonuclease A, Eotaxin-2/MPIF-2, GLO-1, TLR3, HGF, Sterol carrier protein 2/SCP2, Visfatin, SHC1, IL-18 R beta/AcPL, SIGLEC14, PRTN3, Contactin-1, CV-2/Crossveinless-2, EDG-1, CXCL14/BRAK, TIMP-3, Serpin A1, Annexin A1, TGM3, CXCR6, PGM1, Osteoprotegerin/TNFRSF11B, Coagulation Factor III/Tissue Factor, M-CSF R, MDC, FAM3B, MMP-11/Stromelysin-3, SCF R/CD117, TGF-beta 5, Titin, sFRP-3, IL-1 beta, HCC-4/CCL16, TRAIL/TNFSF10, Fascin, BNP, ADAMTS-13, PLOD1, FLRG, LDHA, LIF, YY1, NME3, ESAM, RPS19, EpCAM, TAGLN2, CXCL16, BTF3, Hemoglobin subunit beta/HBB, TRADD, Metavinculin, BDNF, Galectin-7, PPP2R4, FACX, PDZD2, IL-26, FGF-9, Fibrinogen-like 2, Plexin B2, Thrombomodulin, Dtk, TRAIL R2/DR5/TNFRSF10B, PNP, ANGPTL8, B7-H3, ACLP, Galectin-3, p73, IL-4, IL-13 R alpha 2, TOB2, Claudin-3, IL-8, VEGF-C, IGF-I SR, Tenascin X(1), Lefty-A, Thrombospondin-1, OSM R beta, SUCLG1, PDGF-AB, IL-6 R, IL-18 BPa, PGAM2, Cripto-1, FGF-23, GSTM1, ICAM-5, RPL10, Ribonuclease Inhibitor, ARTS1, Periostin, UCH-L1, Zyxin, RPL10A, PDLIM5, IL-15 R alpha, FAM3C, Tropomyosin 3, LZTS1, LIGHT/TNFSF14, Osteoadherin(2), SHMT1, CCR9, TWEAK R/TNFRSF12, TPP1, ADAMTS-10, RCL, PCDH7, MIG, SPARC, SH3BGRL, Thrombospondin-4, UFM 1, Prostaglandin D Synthase/PTGDS, GPR-39, SPTBN1, BLVRB, RKIP, 4-1BB, Decorin, CRIM 1, PCSK9, STD, IL-22 BP, VEGF R2 (KDR), Ficolin-2, CXCR4 (fusin), SIGIRR, IFN-beta, Cyclin D1, MIP-1a, RPS11, Alpha 1 AG, BLAME, Cystatin E/M, GM-CSF R alpha, Uteroglobin(1), Trypsinogeb-2, MCP-3, Erythropoietin R, Proteasome subunit alpha type 6/PSMA6, TGF-alpha, Flt-3 Ligand, Nanog, TNF-alpha, Spectrin beta-5, VNN1, BMP-1, FGF-7/KGF, OSM, FGF R5, Transferrin, C5/C5a, ApoA1, TCP1 eta, Galectin-3BP, PTPRZ, TRAIL R1/DR4/TNFRSF10A, Six3, SORD, CNTF, GDNF, BMPR-II, CXCR2/IL-8 RB, FGF-8, RPS5, CRF21, PGDF/PHGDH, FABP1, SLURP1, CEACAM-8/CD66b, UNC45A, Adiponectin/Acrp30, MMP-25/MT6-MMP, SMC4, Ornithine Carbamoyltransferase/OTC, IFN-gamma R1, CCR4, Proteasome beta 1, Talin1&2, Prohibitin, MMP-24/MT5-MMP, SP-D, Nidogen-2, PTPRS, SIRP beta 1/CD172b, APRIL, ACE-2, IL-6, HGFA, E-Selectin, GATA-4, VEGF R3, UBE2D3, BAFF R/TNFRSF13C, Layilin, Cytokeratin 8, Profilin 1, Cathepsin B, Marapsin, Lymphotactin/XCL1, Nidgen-1, MEP1A, MIF, IL-1 F8/FIL1 eta, MMP-14, HB-EGF, Latent TGF-beta bpl, C8B, SMPD4, ADAMTS-18, FGF Basic, IL-12 R beta 2, MINPPL URP2, Glycoprotein V, LRG1, ACPP, AlphaA Crystallin/CRYAA, EDA-A2, SH3BGRL3, Serpin F2, CD40 Ligand/TNFSF5/CD154, CPEB3, A2M, Activin B, SREC-II, EGF, FGF-19, Myoferlin, Endoglin/CD105, RECK, ADAM-9, SSEA-4, DDAH1, P-Cadherin, IL-22 R, Glut1, Symplekin, S100A11, SLITRK1, GCP-2/CXCL6, SDPR, IGF-II R, P4HB, TNF-beta, IL-1 R8, IL-1 alpha, Angiopoietin-4, TCCR/WSX-1, GITR/TNFRF18, ILK, TCEB2, RPL22, DEP-1, FGF-18, TL1A/TNFSF15, EphA6, IL-36RN, Tarc, UROC1, Activin C, FASN, PYGL, Somatostatin, Musk, PLA2G1B, IL-1 R3/IL-1 R AcP, FGF-6, IL-18 R alpha/IL-1 R5, Tie-2, NIT2, PF4/CXCL4, TPM1, GDF11, IGFBP-6, Thymopoietin, FUCA1, CRHBP, C1qR1, STAT3, TPM4, Follistatin, Laminin b2, IL-1 sRI, CCR7, ApoA2, ENA-78, Myosin 18B, Desmoplakin, Neurabin 1, FGF-4, PDGF-BB, PCBP2, P20Sb3, IGF2BP1, Chordin-Like 2, UNC-13 Homolog D, Enolase 2, Angiopoietin-2, TFF2(1), RHOC, SUMO3, DGK, HVEM/TNFRSF14, GRO-a, GALNT2, TECK/CCL25, Notch-1, Cystatin S, IL-2 R alpha, WNK2, eIF5A, TrypsinPan, SCF, CD30/TNFRSF8, IL-1 F6/FIL1 epsilon, CutA, CFL1, TRAIL R4/TNFRSF10D, MBD2, UBE2N/Ubc13, PI 16, DANCE, FABP2, IGFBP-4, NEP, NRG1 Isoform GGF2, IL-2 R gamma, MAC-1, MPO, SerpinE2, GDF1, IL-17, Orexin A, Kremen-1, Smad 4, IL-17B R, GCSF, Annexin V, IL-31, TRAP1, Transketolase/TALDO, pIgR, Brgl, BMX, MAN', Orosomucoid 2, RAP1AB, VEGF-B, SLC38A10, RPS2, RANTES, SerpinB4, Nestin, Complement factor H, MAPRE1, PDGF-AA, RegIA, MUCDHL, SSTR2, IGSF4B, TSG-6, Orexin B, Quiescin Q6, IGFBP-2, IGFBP-rpl/IGFBP-7, Dystroglycan, Alanine Transaminase/ALT, FKBP12, Growth Hormone R (GHR), MCP-1, IL-21, RANK/TNFRSF11A, HRG-beta 1, ACTC1, Ribonuclease T2, B3GNT1, Src(1), PCYOX1, Leptin R, IL-19, CXCR1/IL-8 RA, PTP mu, IL-1 ra, PDGF-D, HEXB, ERp57, PLC-gamma 1, Nesprin2, Frizzled-4, B7-H2, NAGLU, Serpin B5, TNF RI/TNFRSF1A, IL-1 F9/IL-1 H1, Histone H2B K, OX40 Ligand/TNFSF4, Aminoacylase, Transaldolase 1/TALDO1, Glucagon, IFRD1, sFRP-4, IL-22, Kininostatin/kininogen, PRDM13, CCR5, C 1q, AMPKa1, EXTL2, POR, Smad 8, TXNDC5, IL-17RD, TREM-1, SDNSF, FKBP51, Complement Factor B, Cadherin-6, VCAM-1 (CD106), 11b-HSD1, Tie-1, Vimentin B, DISC 1, RPL7A, GDF-15, IL-31 RA, IL-5 R alpha, p16 ARC, EN-RAGE, Biglycan, DSCAM, Aggrecan, DCI, Cathepsin A, HGFR, sFRP-1, IL-4 R, IL-5, FGF R3, Activin RIA/ALK-2, Prdx6, Cathepsin L, Ezrin, TAX1BP3, FGF-BP, AMICA, KMD4B, Artemin, Ax1, Claudin-4, SDF-1/CXCL12, FADD, MAFIA, ABCF1, Annexin A6, G-CSF R/CD 114, TSLP R, BRCA 2, EphA2, Cystatin SN, Fas Ligand, Pappalysin-1, MEL 2B4, Fc RIIB/C, Dkk-4, alpha-Synuclein, Neural Cadherin, ANGPTL3, C 1q S, ATBF1/ZFHX3, IGF-I, IL-3, IL-3 R alpha, Semaphorin 6B, DPPIV, LAMP2, Angiopoietin-like 1, ERAP2, PCDX8, ALKP, TMEFF2, IFN-alpha/beta R2, STOM, HSP20, Ck beta 8-1, IL-2 R beta/CD122, NrCAM, MMRN1, OSCAR, IL-21 R, PTMA, BLMH, PLS3, IL-10, CPM, cIAP-2, Pref-1, GASP-1/WFIKKNRP, FAP, Fibrinogen, PPCS, LFA-1 alpha, Mc1-1, DcR3/TNFRSF6B, Mesothelin, TACI/TNFRSF13B, Chemerin, WISP2, GM-CSF, DLL4, TLS/FUS, AGA, BTC, Chromogranin B, HMGB3, CFVII, Cryptic, CCR6, CrkL, 14-3-3 beta, TGF-beta RI/ALK-5, EphA1, Trypsin 1, Lipocalin-1, Podocalyxin, sgp130, Lipocalin-2, Caspase-3, ITIH4 a, FSH, Ras, PTP kappa, TIMP-1, Calsyntenin-1, MARCKS, ARP19, Fibronectin, Activin RIB/ALK-4, Chitobiase, OSBP1, IL-23, IL-12 R beta 1, GCSH, PLOD2, Nectin-3, GRP75, Soggy-1, MIP-3 alpha, GFR alpha-4, HMGB1, PCK2, LRP-1, MMP-8, HSP70, EPCR, Epiregulin, Gasl, CTLA-4/CD152, IL-27, TGF-beta 1, Attractin, BNIP2, BMP-5, PKLR, CCR3, Histone H2A, PDGF-C, IL-17B, Osteoactivin/GPNMB, CPE, CD40/TNFRSF5, CAL Triosephosphate isomerase/TPIS, ADAMTS-17, EYA2, GFR alpha-1, Amylin, DMP-1, NUP98, SERPING1, CKB, CCR2, pro-MMP13, ApoC1, Glucose 6 Phosphate Dehydrogenase/G6PD, Caldesmon/CALD1, TLR2, NGF R, PSA-Free, COCO, MRP 1, MCAM, GRP78, IL-9, IL-1 R9, NAIP, RBP4, PABP, CEACAM-1, ADAMTS-5, ALPP, GPX1, Cathepsin X/Z/P, ApoB, Contactin-2, LRP-6, MMP-2, MFRP, Survivin, Siglec-1, PD-ECGF, cTnT, Thioredoxin-1, PGD, RPS23, TPX, LAMP, Myotrophin, SSTR5, IP-10, PGRPL, GDF7, FAM20C, ARFBP1, Activin RIIA, Sonic Hedgehog (Shh N-terminal), ApoC2, CFI, Adipsin, C7, ApoM, HRG, Fibulin 3, HINT', GPBB, GDF5, Histone H1.3, RELM beta, glutathione S transferase Omega 1/GST01, Serpin A3, ErbB2, XIAP, IBSP, MICA, Desmocollin-3, Prolactin, Leptin (OB), WISP-1/CCN4, Aldolase B, NPAS3, LOX-1, hnRNP G, PACS1, BIK, Glycerol 3 Phosphate Dehydrogenase, Olfactomedin-2, GFR alpha-2, MSH6, ANGPTL4, Prouroguanylin, PHAP1, FKBP25, BMP-8, CFHR 1, Osteocalcin, HBZ, HOXD11, LEDGF, NeuroD1, RanGAP1, NF-M, SOX17, PYY, IL-20, Cytochrome c, IL-15, CA 15-3, Hemoglobin, DCBLD2, Serpin DLL1, FGF-21, RNASE6, Annexin A7, PCCA, GLIPR2, Desmuslin, C9, Proteasome 20S b7, ARX, LIF R alpha, C1s, Chymase, Prion protein PrP/PRNP, IFN-gamma, CNOT1, UROD, IL-1 R6/IL-1 Rrp2, PER', CFHR2, Thymidine Kinase-1, PTP gamma, LBP, BCAM, NM23-H1/H2, Lysozyme, Frizzled-5, PARC/CCL18, ROR1, Serpin A8, Persephin, IL-13 R alpha 1, IGFBP-3, Neurturin, perilipin 3, PSMB5, PLUNC, Cathepsin G, Siglec-9, MMP-15, Frizzled-7, ARB1, CL-P1, Glypican 3, MFG-E8, GATA-3, Frizzled-6, beta B1 Crystallin/CRYBB1, Siglec-5/CD170, TOPORS, PIN, Hemoglobin Alc, S100A8, EphB4, CLC, Cystatin A, Transthyretin, GSR, GAPDH, Trappin-2, Plastin L, PSMA1, Cathepsin S, IGFBP-5, LILRA3, GITR Ligand/TNFSF18, KRT31, KCTD10, BTD, LYVE-1, ACE, ECM-1, ZNF671, FoxP3, ROBO4, Cystatin C, BIRC6, Vitronectin, beta-Catenin, beta-I Tubulin, E-Cadherin, IL-1 sRII, Plectin, Spinesin, Endorepellin, Glut2, Insulin R, Serpin D1, Azurocidin, RPS10, Catalase, Glut5, HAI-2, FGFR1 alpha, S100A4, ARPC3, Properdin, Glyoxalase II, Netrin-4, FABP3, ZBTB4, LIMPII, Neuritin, BMP-3b/GDF-10, Vasorin, Cortactin, Cystatin D, Smad 1, MCP-4/CCL13, Syndecan-1, Osteopontin, ApoE, APN, IFN-alpha/beta R1, Fas/TNFRSF6, Erythropoietin, ApoB100, Cathepsin H, TWEAK/TNFSF12, Chordin-Like 1, Pentraxin3/TSG-14, AFP, CD61, Cathepsin D, DOT1L, Desmocollin-2, URB, PRSS3, MASP3, ADAMTS-19, Ephrin B1, TGF-beta 3, ApoH, ALDH1A1, Nectin-1, GFAP, KLK-B1, Secretogranin V/SCG5, Peroxiredoxin 3, EphB6, MYHC, NABC1, PSMD1, AgRP, IL-23 R, Galanin, PIK3IP1, IL-1 F10/IL-1HY2, IL-28A, SOX4, ANK, PON1, Uromodulin, PPDX, Histone H4, Metallothionein, FOLR3, Neurokinin-A, Protein p65, IL-33, HDGF, APLP-1, Frizzled-3, PGRP-S, SOD4, SERPINBL Tenascin C, GMF beta, Fyn, HPR, Neuropilin-2, Lamin A+C, ZC3H4-N-t, GSTP1, PON2, DCXR, GRO, Homerin, COX-2, S100A10, 53BP1, PKM2, S-100b, Lamin B1, PZP, Chitotriosidase, Osteocrin, P1GF, LOK, ALBUMIN, SHANK1, TLR1, HADHA, ApoD, PA2G4, KIF3B, Ubiquitin+1, TXNRD2, Eotaxin/CCL11, HCFC1, IL-20 R beta, Pancreastatin, FGF-10/KGF-2, Brevican, CES1, TIMP-2, MMP-10, CD30 Ligand/TNFSF8, GIP, Kallikrein 10, Ficolin-3, HNF-3 alpha/FoxA1, Thyroglobulin, TFPI, ICAM-3 (CD50), RPL14, S100A9, CA2, Hoxb3, Serpin A9, IL-20 R alpha, TFF1, Pro-BDNF, NCAM2, NPTXR, Guanylin, ALP, TMEFF1/Tomoregulin-1, PSA-total, KIAA1468, IL-7 R alpha, HSP10, GASP-2/WFIKKN, SLPI, Neogenin, Cerberus 1, PSMA7, Beta Defensin 4, FIH, CHC17, Semenogelin I/SEMG1, hHR23b, Proteasome 20S alpha, Histone H3.3, SOST, EV15L, Fetuin A, Fetuin B, GULP1/CED-6, WIF-1, GDF3, INSL3, APC, TSLP, ROCK1, TRA-1-60, HOXA10, MYH7, ACLY, EVC2, CTGF/CCN2, TRA-1-81, 14-3-3 sigma, NELL2, Ferritin, Cytochrome C, B3GNT2, Fibrinopeptide A, PISD, SAMSN1, Glut3, HSP40, PD-1, PDGF R beta, SNCG, ROCK2, CRTH-2, MP1, CD200, PDIA6, Grb2, CNTF R alpha, F11, Frizzled-1, BMP-9, ROR2, L-Selectin (CD62L), Clusterin, AKR1C3, NCAM-1/CD56, S100P, COMP, FGFR1, PARK7, Laminin 2 alpha, PI 3-Kinase C2 beta, IRE1, Filamin B, NT5C3, Lumican, FGFR2, AIF, IL-34, Multimerin 2, Latent TGF beta bp2, ADM, Inhibin beta, FOLR1, SET, Progranulin, RELM alpha, Endothelin Receptor A, FABP4, PPP2R5C, ApoE3, MN1, RPS12, MLCK, INSRR, 14-3-3 epsilon, HP1BP3, Perilipin-1, Furin, ABL1, Mannosidase II, IL-17E, Grainyhead-like protein 1 homolog/GRHL1, Neurotrimin, CLIC1, LOXL1, 14-3-3 theta, RhoGDI, ACTH, Afamin, FBPase 1, Plasminogen, Kallikrein 11, Desmoglein-1, Myoglobin, Contactin-4, PECAM-1/CD31, ADH1C, ATPSO, NOV/CCN3, CRTAM, Serpin B3/SCCA1, MBL, CA 125, Smad 7, Growth Hormone (GH), OX40, Serpin A5, TRP-1, PEPSINOGEN II, PEBP4, mTOR, hnRNP L, TACE, 14-3-3 eta, IL-17C, MMP-7, Kallikrein 7, AFG3L2, VEGI/TNFSF15, APP, LAIR1, Ran, Kallikrein 14, HSP90, Nesfatin, p27, TIM-1, Pancreatic Polypeptide, MYO5A, CPNE3, Peroxiredoxin 2, Nebulin, Aldehyde Oxidase 1/AOX1, BAZ2B, Actinin alpha 1, CA3, CCT3, MMR, Progesterone, HMGB2, PDX-1, Gastrokine 1, Factor XIII, TGF-beta 2, MMP-12, Caspase-8, PSMC3, ITM2B, PDLIM1, Plexin B1, H6PD, IL-12 p70, NAP1L1, NPM1, LRP 4, Prostasin, p21, SART1, SEZ6L2, VSIG4, SEMA3A, Hemoglobin subunit gamma 2/HBG2, IL-13, ANGPTL6, NR3C3, PEDF, Livin, ABI3BP, Noelin, HTRA1, FABP5, Kremen-2, SCGF, RPS3, B4GalT1, ACK1, APOA1BP, ADAMTS-1, THOP1, IL-7, TSH, CLIP170-N-t, EphA3, IL-24, Ntnl, Fibrinogen gamma chain/FGG, Rab7a, SIM2, Neuropeptide B, HCR/CRAM-A/B, Serpin A12, OCT3/4, FER, ITIH3, LIN41, Mer, Hepassocin, PSMD9, hnRNP A1, BCHE, Omentin, SF20, IRS2, URB2, GPX3, MMP-16/MT3-MMP, GCLC, Cytokeratin 18, FH, IL-17RC, FGF-5, GFR alpha-3, GDI2, Lamin B2, ELAVL1, UGGT, IL-17R, CTACK/CCL27, DBI, KRTDAP, SAA, MYH2, CRTAC1, HEG1, Annexin A2, P-selectin, PAI-1, Factor XIII B, Advillin-N-t, Destrin, LUZP1, Serpin A10/ZPI, HSP32, Kallikrein 5, 01T3, Dkk-1, KRTHA3B, ENO1+ENO2+ENO3, Endocan, MSHa, AKR1B1, TXK, Pro-Cathepsin B, SOX2, JAM-A, SERTAD2, BMP-7, SPINKL CLIC4, Human Agrin, Aldolase A, UNC5H4, GLP-1, ERRa, EphB2, C5b-9, RNA Polymerase II/POLR2A, ASPH, ANP, Antithrombin III, Cytokeratin 14, PYK2, GRP, AHNAK, hCG alpha, SorLA, EFTUD2, Endorphin Beta, Cytokeratin 17, USP5, Granzyme A, CA 9, QPRT, JARID2, S100A1, ADAMTS-L2, Pleckstrin, RELT/TNFRSF19L, IBP160, nNOS, GADD45A, C-peptide, Moesin, Hepcidin, CCR1, Pro-MMP-7, CLEC3B, Bax, HSP60, PARVB, HAI-1, Fox01, SOD1, APCS, Desmoglein-2, ProSAAS, ALDH9A1, EphA4, C4.4A, Corneodesmosin, MICB, HPD, CAD, HSPA8, RPS20, Serpin A7, TNK1, IDUA, SHP-1, FGF-11, Serpin A11, TWF2, SSEA-1, Proteasome subunit beta type 2/PSB2, FLG2, MIP-1d, p53, Kallikrein 6, SHBG, Hemopexin, GRP, PTN, DEFA6, Talin1, NASP, MIP 2, EIF3S2, VCP, Chem R23, Ceruloplasmin, TFF3, HN1, ITIH2, APJ, HPRT, RYK, EN2, ETL, TRKB, GM2A, KRT82, ERp29, MMP-13, ATPB, Cardiotrophin-1/CT-1, CBP, ZC3H8, Presenilin 2, CALML5, Cystatin B, AR (Amphiregulin), Presenilin 1, SART3, S100A7, Laminin gamma 1, LPS, MANF, ASH2L, GLRX1, NRG3, LH, ENSA, FRY, DDX3Y, GNB1, Proteasome 20S alpha 5, NF1, Proteasome 26S S5, TRPM7, Oxytocin-neurophysin 1/OXT, C1RL, Thymosin b10, BPIFB1, VIP Receptor 2, MFAP4, Fibrillin 1, Desmin, PAK7, CD27/TNFRSF7, Integrin alpha V, HRSP12, 14-3-3 zeta, SAA4a, Syndecan-3, Cezanne, PEPSINOGEN I, PPARg2, LTBP4, GATM-C-terminal, IL-17D, IL-12 p40, TPA, SOD-3, Serpin B6, Legumain, OBCAM, MCP-2, CA 19-9, IL-10 R beta, Procalcitonin, Thrombin, IL-1 F7/FIL1 zeta, EHD3, Gelsolin, Calbindin D, FCGBP, CHORDC1, gamma Catenin, BACE-1, Calreticulin, EphA8, Granzyme M, Thrombospondin-2, Wilms Tumor 1, FOXN3, SPEN, VDUP-1, POMC, Tyk2, C6-N-t, PDE1B, TAB182, IL-16, Rbm15, Cytokeratin 19, SOD2, Eosinophil derived neurotoxin/EDN, Pro-MMP-9, Lubricin, GMNN, 67LR, TRPS1, Dopamine beta Hydroxylase/DBH, ITGB4BP, hnRNP U, IDH1, SynCAM, KIAA1967, CEA, Resistin, Syntaxin 7, NET1, CS, COL19A1, EphB1, EPPK1, C9orf40, LOX, Lymphotoxin beta R/TNFRSF3, Neuropeptide Y, p39, DDT, MCMP2, GNPTG, Angiopoietin-like 2, CIP29, TOP2B, Corticosteroid-binding globulin, non-muscle Myosin IIA/Myosin, BAFF, C2, Plxdc2, FUCA2, Ube2L3, DMRN9, CARHSP1, GDF9, SMAC, MAGP-2, CYTL1, GARNL1, EMSY, BMPR-IB/ALK-6, PCNA, Apexl, LAMP1, Filamin A, pro-Glucagon, VEGF R1, Beta 2M, IL-10 R alpha, ROS, HE4, ZDHHC18, ALK, CLPS, RPL17, Proteasome subunit beta type 4/PSB4, Ubiquitin, LCMT2, Versican isoform V0, hnRNP A2B1, Envoplakin, GPCR GPR116, LTK, Vasopressin, Vitamin D Receptor, SDF4, TRPC1, CA150, COTL1, HMGN2, NAPRT1, hGH, SMA, Glutamyl hydrolase gamma/CGH, CCL14/HCC-1/HCC-3, GRHPR, Prosaposin, COLEC10, TROPONIN I, MDH2, PSP, Ghrelin, MTUS1, Netrin G2, ALS, Notch-2 ICD, FBP 38, FAK, Intergrin a6, DAN, BLC/BCA-1/CXCL13, Troponin C, PF4V1, G3BP, ADAMDEC1, CCDC126, ACACA, EphA5, Hck, NRG2, hnRNP C1+C2, MYL3, Peroxiredoxin 5, Vitamin K-dependent protein S, PTK 7, UQCRH, SYK, CART, Serpin A4, TXNDC4, Apo (a), APM2, ITGB5, 14-3-3 gamma, Dermcidin, AKR7A2, ORP150, VWF, Cytokeratin 4, GPI, CCDC25, MIP-lb, Midkine, DSPG3, AKAP9, BAD, Apolipoprotein L 2, LMW-PTP/ACP1, EFEMP2, HTRA2, Kallikrein 8, KLF4, EMILIN1, XEDAR, Aconitase 1, CHI3L1, hCGb, DARS2, UPB1, ERp72, HIP1R, BD-1, Ctip2, D4 GDI, CCK, PCPE-1, CRP, Cux2, MAGI2, MyBPC3, ARP2/3, EEF2, Kallikrein 2, Tryptophanyl, LTA4H, PGAM1, PSMA2, alpha 1,2 Mannosidase IA/MAN1A1, Cytokeratin 16, SRMS, GDA, C3orf75, FASTKD5, CETP, DPP3, ARFGEF3, Calpain 1, Csk, Cytokeratin 15, DEFA1/3, Nucleobindin 1/NUCB1, Factor XII, ENO1, BRSK1, fast skeletal Myosin, Factor V, ASXL1, mGLUR5, Cytokeratin 10, ESR1, beta III Tubulin/CUBB3, LDHB, TRPC6, Serotonin, p23, CPA1, Ahsp, Kilon, Protein Z, Calpastatin, BIN2, EphB3, MFI2, Cytokeratin 3, EPHX2, Cytokeratin 5, PCAF, ASK1, CLTA, CNDP1, MPCA, Mimecan, HSC70, Fumarylacetoacetate hydrolase/FAH, GHRF, ADH1B, ITIH1, DNER, MBP, Apelin, LYPA1, CACNB4, BPGM, Cadherin 22, HIBADH, VGF, ABAT, G0/Glswitch 2, Ephrin B2, SCG3, ERAB, CHREBP, Hemoglobin subunit delta/HBD, ClqTNF1, Haptoglobin, D-Dimer, Calmodulin, EphA7, alpha Tubulin, PRSS23, Cytokeratin 20, Tec, Coronin 3, TIM-4, CD 163, MGP, Aspartate Aminotransferase/AST, MYH6, Karyopherin beta 1, DR3/TNFRSF25, CECR1, ACTBL2, CNN2, BMPR-IA/ALK-3, BMP-4, GDI1, TYRO10, TAF4, hnRNP M1-M4, ZAP70, Stathmin 1, HLA-C, Argininosuccinate Lyase/ASL, Integrin beta 6, TRF 2, Chromogranin C, CLEC14A, ENPP2, Itk, MCM, Bcl-w, PI 3Kinase p85 beta, PTPRD, LEKTI/SPINK5, Lyn, Fen 1, Factor IX, CRMP2, EPB41, MINA, PCBP1, Lck, KHSRP, DAK, IL-1 R4/ST2, Histone H2A.Z, ESD, CO4A2, ZAG, CBG, HABP2, Histone H1.2, ACAA2, Cytokeratin 13, Bassoon, Alpha 1 Microglobulin, COL9A3, BAF57, PTH, ART3, ADAMTS-4, EEF1G, Androgen Receptor, MATK, KCC3, Eps 15, Non-muscle Actin/Actin, Chromogranin A, GST, FBP2, BID, MMP-19, MDH1, Selenoprotein P, Arp2, KMT2B, CPS1, Calretinin, Apolipoprotein F, ACAA1, HSP27, CEP57, IGFBP-1, PCMT1, BPIL1, eIF4A1-N-t, Alpha Lactalbumin, PDGF R alpha, CENPF, Creatine Kinase MM/CKMM, Asialoglycoprotein Receptor 2/ASGR2, Phosphoserine Aminotransferase/PSAT1, Gastrin, Aldolase C, CAPZA1, IDH3A, Keratin 38, GOT2, Alpha Fodrin, GLUD1, D6, GBE1, Krt73, E1 Ubiquitin Activating Enzyme/UBA1, BCOR, CPN1, PTEN, Cathelicidin, GPLD1, MCMS, NQO2, GCDFP 15, RET, A1BG, HEXA, Acetyl-CoA acetyltransferase/ACAA, Glucosidase 2 subunit beta/PRKCSH, KRT72, KIFSB, PPP2R1B, gamma-Thrombin, Alcohol Dehydrogenase/ADH, EHD1, COPSE, FRK, IGF2BP2, alpha Glucosidase II, KSR1, CPN2, LAG-3, AK2, PEPD, ADAS, Creatinine, COL4A3, LMAN2, RIP1, Cytokeratin 9, SPARCL1, Filamin C, MIP-3 beta, KRT85-N-terminal, LAD, GOLPH4, Cytochrome b5, ADH4, ARPC2, LYRIC, Angiopoietin-1, FDPS, Apolipoprotein L 1, DPEP2, Vitamin D-BP, Ankrd26, APA, ArgRS, Fibrinopeptide B, LAP3, Ihh, ALDH16A1, IQ GAP1, LAS P1, Integrin b1, DPPI, TRAP220, Glutathione Synthetase/GSS, BASP1, Btk, ATPSA, Keratin 36, ECHS1, Desmocollin 1, DRILL LTF, GART, Contactin-3, S100 A8/A9, Arp3, GOLPH2, ISOC2, alpha Actinin 4, GREMLIN, Frizzled 8, LAM b1, PTHLP, LAF4, and/or MMP-20.

In various aspects, at least one component isolated from the extracellular matrix (an "ECM component") may be present in the exosome composition at a concentration at least at least 5 times, 10 times, at least 20 times, at least 30 times, at least 40 times, or at least 50 times the concentration of the ECM component in a comparable exosome preparation, as defined below.

In various aspects, the exosome composition may comprise at least one ECM component at a concentration at least 5 times the concentration of the ECM component in a comparable exosome preparation (e.g., one prepared using ultra-centrifugation). For example, the exosome composition may comprise one or more of the following ECM components at a concentration that is at least 5 times the concentration of the ECM component in a comparative exosome preparation (e.g., prepared using ultra-centrifugation): Cysteine-rich Protein 1, PIM2, Cadherin-13, Beta IG-H3, EG-VEGF/PK1, Cyclophilin A, Dkk-3, BMP-3, QDPR, PAM, EDAR, EGF R/ErbB 1, ALCAM, CXCR3, SBP-1, BCMA/TNFRSF17, CCL28/VIC, IL-29, HSP47, VE-Cadherin, 1-309, TGF-beta RIII, CCR8, Fractalkine, TCN1, RSU1, uPAR, VEGF-D, PRELP, TGF-beta RII, Thrombopoietin (TPO), Endothelin, S100A6, Angiogenin, TIMP-4, MSP alpha Chain, Activin A, DMGDH, Serpin B8, TRAIL R3/TNFRSF10C, CFHR5, Caspase-14, PRDX 1, FGF-12, CXCR5/BLR-1, Semaphorin 7A, SPINK7, NT-4, TNF RII/TNFRSF1B, 6Ckine, SerRS, Angiostatin, Angiopoietin-like Factor, B7-1/CD80, Protein C, Tcf20, TROY/TNFRSF19, EMAP-II, CSH1, TLR4, RPLPO, ErbB3, RPL11, PGK-1, FGF-16, Plakophilin 1, PRCP, RAGE, Insulin, TSR2, NT-3, USP14, VDAC1/Porin, Proteasome 20S a+b, M-CSF, IL-2, ICAM-1, NEDD8, PRG2, Insulysin/IDE, ICAM-2, MMP-1, Salivary alpha amylase/aAmylase, IL-17F, Galectin-1, Lymphotoxin beta/TNFSF3, TBCA, PREP, VAP-A, Utrophin, YB1, VAP-1, CFHR4, FGF-20, Cyclophilin B, RNASE4, SBSN, FGF R4, FGF-17, PGLS-C-t, Eotaxin-3/CCL26, RREB1, TMEM223, ADAMTS-15, Semenogelin II/SEMG2, C3a, RPL12, GDF8, IGF-II, RPS25, Follistatin-like 1, Smad 5, Notch-2, I-TAC/CXCL11, TRANCE, MMP-3, uPA, WDR1, UQCRB, DR6/TNFRSF21, BMP-15, PSMA4, ErbB4, Gephyrin, beta-NGF, BMP-2, BMP-6, NAP-2, LECT2, FGF-13 1B, Reg3A, CD14, SHIP, RPL5, VEGF, IL-1 F5/FILldelta, RPS28, TUBA6, Endostatin, MMP-9, CK-MB, CapG, IL-11, Ribonuclease A, Eotaxin-2/MPIF-2, GLO-1, TLR3, HGF, Sterol carrier protein 2/SCP2, Visfatin, SHC1, IL-18 R beta/AcPL, SIGLEC14, PRTN3, Contactin-1, CV-2/Crossveinless-2, EDG-1, CXCL14/BRAK, TIMP-3, Serpin A1, Annexin A1, TGM3, CXCR6, PGM1, Osteoprotegerin/TNFRSF11B, Coagulation Factor III/Tissue Factor, M-CSF R, MDC, FAM3B, MMP-11/Stromelysin-3, SCF R/CD117, TGF-beta 5, Titin, sFRP-3, IL-1 beta, HCC-4/CCL16, TRAIL/TNFSF10, Fascin, BNP, ADAMTS-13, PLOD1, FLRG, LDHA, LIF, YY1, NME3, ESAM, RPS19, EpCAM, TAGLN2, CXCL16, BTF3, Hemoglobin subunit beta/HBB, TRADD, Metavinculin, BDNF, Galectin-7, PPP2R4, FACX, PDZD2, IL-26, FGF-9, Fibrinogen-like 2, Plexin B2, Thrombomodulin, Dtk, TRAIL R2/DR5/TNFRSF10B, PNP, ANGPTL8, B7-H3, ACLP, Galectin-3, p73, IL-4, IL-13 R alpha 2, TOB2, Claudin-3, IL-8, VEGF-C, IGF-I SR, Tenascin X(1), Lefty-A, Thrombospondin-1, OSM R beta, SUCLG1, PDGF-AB, IL-6 R, IL-18 BPa, PGAM2, Cripto-1, FGF-23, GSTM1, ICAM-5, RPL10, Ribonuclease Inhibitor, ARTS1, Periostin, UCH-L1, Zyxin, RPL10A, PDLIM5, IL-15 R alpha, FAM3C, Tropomyosin 3, LZTS1, LIGHT/TNFSF14, Osteoadherin(2), SHMT1, CCR9, TWEAK R/TNFRSF12, TPP1, ADAMTS-10, RCL, PCDH7, MIG, SPARC, SH3BGRL, Thrombospondin-4, UFM 1, Prostaglandin D Synthase/PTGDS, GPR-39, SPTBN1, BLVRB, RKIP, 4-1BB, Decorin, CRIM 1, PCSK9, STII, IL-22 BP, VEGF R2 (KDR), Ficolin-2, CXCR4 (fusin), SIGIRR, IFN-beta, Cyclin D1, MIP-1a, RPS11, Alpha 1 AG, BLAME, Cystatin E/M, GM-CSF R alpha, Uteroglobin(1), Trypsinogeb-2, MCP-3, Erythropoietin R, Proteasome subunit alpha type 6/PSMA6, TGF-alpha, Flt-3 Ligand, Nanog, TNF-alpha, Spectrin beta-5, VNN1, BMP-1, FGF-7/KGF, OSM, FGF R5, Transferrin, C5/C5a, ApoA1, TCP1 eta, Galectin-3BP, PTPRZ, TRAIL R1/DR4/TNFRSF10A, Six3, SORD, CNTF, GDNF, BMPR-II, CXCR2/IL-8 RB, FGF-8, RPS5, CRF21, PGDF/PHGDH, FABP1, SLURP1, CEACAM-8/CD66b, UNC45A, Adiponectin/Acrp30, MMP-25/MT6-MMP, SMC4, Ornithine Carbamoyltransferase/OTC, IFN-gamma R1, CCR4, Proteasome beta 1, Talin1 &2, Prohibitin, MMP-24/MT5-MMP, SP-D, Nidogen-2, PTPRS, SIRP beta 1/CD172b, APRIL, ACE-2, IL-6, HGFA, E-Selectin, GATA-4, VEGF R3, UBE2D3, BAFF R/TNFRSF13C, Layilin, Cytokeratin 8, Profilin 1, Cathepsin B, Marapsin, Lymphotactin/XCL1, Nidgen-1, MEP1A, MIF, IL-1 F8/FIL1 eta, MMP-14, HB-EGF, Latent TGF-beta bpl, C8B, SMPD4, ADAMTS-18, FGF Basic, IL-12 R beta 2, MINPPL URP2, Glycoprotein V, LRG1, ACPP, AlphaA Crystallin/CRYAA, EDA-A2, SH3BGRL3, Serpin F2, CD40 Ligand/TNFSF5/CD154, CPEB3, A2M, Activin B, SREC-II, EGF, FGF-19, Myoferlin, Endoglin/CD105, RECK, ADAM-9, SSEA-4, DDAH1, P-Cadherin, IL-22 R, Glut1, Symplekin, S100A11, SLITRK1, GCP-2/CXCL6, SDPR, IGF-II R, P4HB, TNF-beta, IL-1 R8, IL-1 alpha, Angiopoietin-4, TCCR/WSX-1, GITR/TNFRF18, ILK, TCEB2, RPL22, DEP-1, FGF-18, TL1A/TNFSF15, EphA6, IL-36RN, Tarc, UROC1, Activin C, FASN, PYGL, Somatostatin, Musk, PLA2G1B, IL-1 R3/IL-1 RAcP, FGF-6, IL-18 R alpha/IL-1 R5, Tie-2, NIT2, PF4/CXCL4, TPM1, GDF11, IGFBP-6, Thymopoietin, FUCA1, CRHBP, C1qR1, STAT3, TPM4, Follistatin, Laminin b2, IL-1 sRI, CCR7, ApoA2, ENA-78, Myosin 18B, Desmoplakin, Neurabin 1, FGF-4, PDGF-BB, PCBP2, P20Sb3, IGF2BP1, Chordin-Like 2, UNC-13 Homolog D, Enolase 2, Angiopoietin-2, TFF2(1), RHOC, SUMO3, DGK, HVEM/TNFRSF14, GRO-a, GALNT2, TECK/CCL25, Notch-1, Cystatin S, IL-2 R alpha, WNK2, eIF5A, TrypsinPan, SCF, CD30/TNFRSF8, IL-1 F6/FIL1 epsilon, CutA, CFL1, TRAIL R4/TNFRSF10D, MBD2, UBE2N/Ubc13, PI 16, DANCE, FABP2, IGFBP-4, NEP, NRG1 Isoform GGF2, IL-2 R gamma, MAC-1, MPO, SerpinE2, GDF1, IL-17, Orexin A, Kremen-1, Smad 4, IL-17B R, GCSF, Annexin V, IL-31, TRAP1, Transketolase/TALDO, pIgR, Brgl, BMX, MAN1, Orosomucoid 2, RAP1AB, VEGF-B, SLC38A10, RPS2, RANTES, SerpinB4, Nestin, Complement factor H, MAPRE1, PDGF-AA, ReglA, MUCDHL, SSTR2, IGSF4B, TSG-6, Orexin B, Quiescin Q6, IGFBP-2, IGFBP-rpl/IGFBP-7, Dystroglycan, Alanine Transaminase/ALT, FKBP12, Growth Hormone R (GHR), MCP-1, IL-21, RANK/TNFRSF11A, HRG-beta 1, ACTC1, Ribonuclease T2, B3GNT1, Src(1), PCYOX1, Leptin R, IL-19, CXCR1/IL-8 RA, PTP mu, IL-1 ra, PDGF-D, HEXB, ERp57, PLC-gamma 1, Nesprin2, Frizzled-4, B7-H2, NAGLU, Serpin B5, TNF RI/TNFRSF1A, IL-1 F9/IL-1 H1, Histone H2B K, OX40 Ligand/TNFSF4, Aminoacylase, Transaldolase 1/TALDO1, Glucagon, IFRD1, sFRP-4, IL-22, Kininostatin/kininogen, PRDM13, CCR5, C 1q, AMPKa1, EXTL2, POR, Smad 8, TXNDC5, IL-17RD, TREM-1, SDNSF, FKBP51, Complement Factor B, Cadherin-6, VCAM-1 (CD106), 11b-HSD1, Tie-1, Vimentin B, DISC 1, RPL7A, GDF-15, IL-31 RA, IL-5 R alpha, p16 ARC, EN-RAGE, Biglycan, DSCAM, Aggrecan, DCI, Cathepsin A, HGFR, sFRP-1, IL-4 R, IL-5, FGF R3, Activin RIA/ALK-2, Prdx6, Cathepsin L, Ezrin, TAXIBP3, FGF-BP, AMICA, KMD4B, Artemin, Ax1, Claudin-4, SDF-1/CXCL12, FADD, MAP1A, ABCF1, Annexin A6, G-CSF R/CD 114, TSLP R, BRCA 2, EphA2, Cystatin SN, Fas Ligand, Pappalysin-1, MEi, 2B4, Fc RIIB/C, Dkk-4, alpha-Synuclein, Neural Cadherin, ANGPTL3, C 1q S, ATBF1/ZFHX3, IGF-I, IL-3, IL-3 R alpha, Semaphorin 6B, DPPIV, LAMP2, Angiopoietin-like 1, ERAP2, PCDX8, ALKP, TMEFF2, IFN-alpha/beta R2, STOM, HSP20, Ck beta 8-1, IL-2 R beta/CD122, NrCAM, MMRN1, OSCAR, IL-21 R, PTMA, BLMH, PLS3, IL-10, CPM, cIAP-2, Pref-1, GASP-1/WFIKKNRP, FAP, Fibrinogen, PPCS, LFA-1 alpha, Mcl-1, DcR3/TNFRSF6B, Mesothelin, TACI/TNFRSF13B, Chemerin, WISP2, GM-CSF, DLL4, TLS/FUS, AGA, BTC, Chromogranin B, HMGB3, CFVII, Cryptic, CCR6, CrkL, 14-3-3 beta, TGF-beta RI/ALK-5, EphA1, Trypsin 1, Lipocalin-1, Podocalyxin, sgp130, Lipocalin-2, Caspase-3, ITIH4 a, FSH, Ras, PTP kappa, TIMP-1, Calsyntenin-1, MARCKS, ARP19, Fibronectin, Activin RIB/ALK-4, Chitobiase, OSBP1, IL-23, IL-12 R beta 1, GCSH, PLOD2, Nectin-3, GRP75, Soggy-1, MIP-3 alpha, GFR alpha-4, HMGB1, Gasi, PCK2, LRP-1, MMP-8, HSP70, EPCR, Epiregulin, Gasi, CTLA-4/CD152, IL-27, TGF-beta 1, Attractin, BNIP2, BMP-5, PKLR, CCR3, Histone H2A, PDGF-C, IL-17B, Osteoactivin/GPNMB, CPE, CD40/TNFRSF5, CA1, Triosephosphate isomerase/TPIS, ADAMTS-17, EYA2, GFR alpha-1, Amylin, DMP-1, NUP98, SERPING1, CKB, CCR2, pro-MMP13, ApoC1, Glucose 6 Phosphate Dehydrogenase/G6PD, Caldesmon/CALD1, TLR2, NGF R, PSA-Free, COCO, MRP 1, MCAM, GRP78, IL-9, IL-1 R9, NAIP, RBP4, PABP, CEACAM-1, ADAMTS-5, ALPP, GPX1, Cathepsin X/Z/P, ApoB, Contactin-2, LRP-6, MMP-2, MFRP, Survivin, Siglec-1, PD-ECGF, cTnT, Thioredoxin-1, PGD, RPS23, TPX, LAMP, Myotrophin, SSTR5, IP-10, PGRPL, GDF7, FAM20C, ARFBP1, Activin RIIA, Sonic Hedgehog (Shh N-terminal), ApoC2, CFI, Adipsin, C7, ApoM, HRG, Fibulin 3, HINT1, GPBB, GDF5, Histone H1.3, RELM beta, glutathione S transferase Omega 1/GSTO1, Serpin A3, ErbB2, XIAP, IBSP, MICA, Desmocollin-3, Prolactin, Leptin (OB), WISP-1/CCN4, Aldolase B, NPAS3, LOX-1, hnRNP G, PACS1, BIK, Glycerol 3 Phosphate Dehydrogenase, Olfactomedin-2, GFR alpha-2, MSH6, ANGPTL4, Prouroguanylin, PHAP1, FKBP25, BMP-8, CFHR 1, Osteocalcin, HBZ, HOXD11, LEDGF, NeuroD1, RanGAP1, NF-M, SOX17, PYY, IL-20, Cytochrome c, IL-15, CA 15-3, Hemoglobin, DCBLD2, Serpin I1, DLL1, FGF-21, RNASE6, Annexin A7, PCCA, GLIPR2, Desmuslin, C9, Proteasome 20S b7, ARX, LIF R alpha, CIs, Chymase, Prion protein PrP/PRNP, IFN-gamma, CNOT1, UROD, IL-1 R6/IL-1 Rrp2, PER1, CFHR2, Thymidine Kinase-1, PTP gamma, LBP, BCAM, NM23-H1/H2, Lysozyme, Frizzled-5, PARC/CCL18, ROR1, Serpin A8, Persephin, IL-13 R alpha 1, IGFBP-3, Neurturin, perilipin 3, PSMB5, PLUNC, Cathepsin G, Siglec-9, MMP-15, Frizzled-7, ARB1, CL-P1, Glypican 3, MFG-E8, GATA-3, Frizzled-6, betaB1 Crystallin/CRYBB1, Siglec-5/CD170, TOPORS, PIN, Hemoglobin Alc, S100A8, EphB4, CLC, Cystatin A, Transthyretin, GSR, GAPDH, Trappin-2, Plastin L, PSMA1, Cathepsin S, IGFBP-5, LILRA3, GITR Ligand/TNFSF18, KRT31, KCTD10, BTD, LYVE-1, ACE, ECM-1, ZNF671, FoxP3, ROBO4, Cystatin C, BIRC6, Vitronectin, beta-Catenin, beta-I Tubulin, E-Cadherin, IL-1 sRII, Plectin, Spinesin, Endorepellin, Glut2, Insulin R, Serpin D1, Azurocidin, RPS10, Catalase, Glut5, HAI-2, FGFR1 alpha, S100A4, ARPC3, Properdin, Glyoxalase II, Netrin-4, FABP3, ZBTB4, LIMPII, Neuritin, BMP-3b/GDF-10, Vasorin, Cortactin, Cystatin D, Smad 1, MCP-4/CCL13, Syndecan-1, Osteopontin, ApoE, APN, IFN-alpha/beta RI, Fas/TNFRSF6, Erythropoietin, ApoB100, Cathepsin H, TWEAK/TNFSF12, Chordin-Like 1, Pentraxin3/TSG-14, AFP, CD61, Cathepsin D, DOT1L, Desmocollin-2, URB, PRSS3, MASP3, ADAMTS-19, Ephrin B1, TGF-beta 3, ApoH, ALDH1A1, Nectin-1, GFAP, KLK-B1, Secretogranin V/SCG5, Peroxiredoxin 3, EphB6, MYHC, NABC1, PSMD1, AgRP, IL-23 R, Galanin, PIK3IP1, IL-1 F10/IL-1HY2, IL-28A, SOX4, ANK, PON1, Uromodulin, PPOX, Histone H4, Metallothionein, FOLR3, Neurokinin-A, Protein p65, IL-33, HDGF, APLP-1, Frizzled-3, PGRP-S, SOD4, SERPINBI, Tenascin C, GMF beta, Fyn, HPR, Neuropilin-2, Lamin A+C, ZC3H4-N-t, GSTP1, PON2, DCXR, GRO, Hornerin, COX-2, S100A10, 53BP1, PKM2, S-100b, Lamin B1, PZP, Chitotriosidase, Osteocrin, P1GF, LOK, ALBUMIN, SHANK1, TLR1, HADHA, ApoD, PA2G4, KIF3B, Ubiquitin+1, TXNRD2, Eotaxin/CCL11, HCFC1, IL-20 R beta, Pancreastatin, FGF-10/KGF-2, Brevican, CES1, TIMP-2, MMP-10, CD30 Ligand/TNFSF8, GIP, Kallikrein 10, Ficolin-3, HNF-3 alpha/FoxA1, Thyroglobulin, TFPI, ICAM-3 (CD50), RPL14, S100A9, CA2, Hoxb3, Serpin A9, IL-20 R alpha, TFF1, Pro-BDNF, NCAM2, NPTXR, Guanylin, ALP, TMEFF1/Tomoregulin-1, PSA-total, KIAA1468, IL-7 R alpha, HSP10, GASP-2/WFIKKN, SLPI, Neogenin, Cerberus 1, PSMA7, Beta Defensin 4, FIH, CHC17, Semenogelin I/SEMG1, hHR23b, Proteasome 20S alpha, Histone H3.3, SOST, EV15L, Fetuin A, Fetuin B, GULP1/CED-6, WIF-1, GDF3, INSL3, APC, TSLP, ROCK1, TRA-1-60, HOXA10, MYH7, ACLY, EVC2, CTGF/CCN2, TRA-1-81, 14-3-3 sigma, NELL2, Ferritin, Cytochrome C, B3GNT2, Fibrinopeptide A, PISD, SAMSN1, Glut3, HSP40, PD-1, PDGF R beta, SNCG, ROCK2, CRTH-2, MP1, CD200, PDIA6, Grb2, CNTF R alpha, F11, Frizzled-1, BMP-9, ROR2, L-Selectin (CD62L), Clusterin, AKR1C3, NCAM-1/CD56, S100P, COMP, FGFR1, PARK7, Laminin 2 alpha, PI 3-Kinase C2 beta, IRE1, Filamin B, NT5C3, Lumican, FGFR2, AIF, IL-34, Multimerin 2, Latent TGF beta bp2, ADM, Inhibin beta, FOLR1, SET, Progranulin, RELM alpha, Endothelin Receptor A, FABP4, PPP2R5C, ApoE3, MN1, RPS12, MLCK, INSRR, 14-3-3 epsilon, HP1BP3, Perilipin-1, Furin, ABL1, Mannosidase II, IL-17E, Grainyhead-like protein 1 homolog/GRHL1, Neurotrimin, CLIC1, LOXL1, 14-3-3 theta, RhoGDI, ACTH, Afamin, FBPase 1, Plasminogen, Kallikrein 11, Desmoglein-1, Myoglobin, Contactin-4, PECAM-1/CD31, ADH1C, ATP50, NOV/CCN3, CRTAM, Serpin B3/SCCA1, MBL, CA 125, Smad 7, Growth Hormone (GH), OX40, Serpin A5, TRP-1, PEPSINOGEN II, PEBP4, mTOR, hnRNP L, TACE, 14-3-3 eta, IL-17C, MMP-7, Kallikrein 7, AFG3L2, VEGI/TNFSF15, APP, LAIR1, Ran, Kallikrein 14, HSP90, Nesfatin, p27, TIM-1, Pancreatic Polypeptide, MYO5A, CPNE3, Peroxiredoxin 2, Nebulin, Aldehyde Oxidase 1/AOX1, BAZ2B, Actinin alpha 1, CA3, CCT3, MMR, Progesterone, HMGB2, PDX-1, Gastrokine 1, Factor XIII, TGF-beta 2, MMP-12, Caspase-8, PSMC3, ITM2B, PDLIM1, Plexin B1, H6PD, IL-12 p70, NAP1L1, NPM1, LRP 4, Prostasin, p21, SART1, SEZ6L2, VSIG4, SEMA3A, Hemoglobin subunit gamma 2/HBG2, IL-13, ANGPTL6, NR3C3, PEDF, Livin, ABI3BP, Noelin, HTRA1, FABP5, Kremen-2, SCGF, RPS3, B4GalT1, ACK1, APOAIBP, ADAMTS-1, THOP1, IL-7, TSH, CLIP170-N-t, EphA3, IL-24, Ntni, Fibrinogen gamma chain/FGG, Rab7a, SIM2, Neuropeptide B, HCR/CRAMA/B, Serpin A12, OCT3/4, FER, ITIH3, LIN41, Mer, Hepassocin, PSMD9, hnRNP A1, BCHE, Omentin, SF20, IRS2, URB2, GPX3, MMP-16/MT3-MMP, GCLC, Cytokeratin 18, FH, IL-17RC, FGF-5, GFR alpha-3, GDI2, Lamin B2, ELAVL1, UGGT, IL-17R, CTACK/CCL27, DBI, KRTDAP, SAA, MYH2, CRTAC1, HEG1, Annexin A2, P-selectin, PAI-1, Factor XIII B, Advillin-N-t, Destrin, LUZP1, Serpin A10/ZPI, HSP32, Kallikrein 5, OIT3, Dkk-1, KRTHA3B, ENO1+ENO2+ENO3, Endocan, MSHa, AKR1B1, TXK, Pro-Cathepsin B, SOX2, JAM-A, SERTAD2, BMP-7, SPINKI, CLIC4, Human Agrin, Aldolase A, UNC5H4, GLP-1, ERRa, EphB2, C5b-9, RNA Polymerase II/POLR2A, ASPH, ANP, Antithrombin III, Cytokeratin 14, PYK2, GRP, AHNAK, hCG alpha, SorLA, EFTUD2, Endorphin Beta, Cytokeratin 17, USP5, Granzyme A, CA 9, QPRT, JARID2, S100A1, ADAMTS-L2, Pleckstrin, RELT/TNFRSF19L, IBP160, nNOS, GADD45A, C-peptide, Moesin, Hepcidin, CCR1, Pro-MMP-7, CLEC3B, Bax, HSP60, PARVB, HAI-1, Fox01, SOD1, APCS, Desmoglein-2, ProSAAS, ALDH9A1, EphA4, C4.4A, Corneodesmosin, MICB, HPD, CAD, HSPA8, RPS20, Serpin A7, TNK1, IDUA, SHP-1, FGF-11, Serpin A11, TWF2, SSEA-1, Proteasome subunit beta type 2/PSB2, FLG2, MIP-1d, p53, Kallikrein 6, SHBG, Hemopexin, GRP, PTN, DEFA6, Talin1, NASP, MIP 2, EIF3S2, VCP, Chem R23, Ceruloplasmin, TFF3, HN1, ITIH2, APJ, HPRT, RYK, EN2, ETL, TRKB, GM2A, KRT82, ERp29, MMP-13, ATPB, Cardiotrophin-1/CT-1, CBP, ZC3H8, Presenilin 2, CALML5, Cystatin B, AR (Amphiregulin), Presenilin 1, SART3, S100A7, Laminin gamma 1, LPS, MANF, ASH2L, GLRX1, NRG3, LH, ENSA, FRY, DDX3Y, GNB1, Proteasome 20S alpha 5, NF1, Proteasome 26S S5, TRPM7, Oxytocin-neurophysin 1/OXT, C1RL, Thymosin b10, BPIFB1, VIP Receptor 2, MFAP4, Fibrillin 1, Desmin, PAK7, CD27/TNFRSF7, Integrin alpha V, HRSP12, 14-3-3 zeta, SAA4a, Syndecan-3, Cezanne, PEPSINOGEN I, PPARg2, LTBP4, GATM-C-terminal, IL-17D, IL-12 p40, TPA, SOD-3, Serpin B6, Legumain, OBCAM, MCP-2, CA 19-9, IL-10 R beta, Procalcitonin, Thrombin, IL-1 F7/FIL1 zeta, EHD3, Gelsolin, Calbindin D, FCGBP, CHORDC1, gamma Catenin, BACE-1, Calreticulin, EphA8, Granzyme M, Thrombospondin-2, Wilms Tumor 1, FOXN3, SPEN, VDUP-1, POMC, Tyk2, C6-N-t, PDE1B, TAB182, IL-16, Rbm15, Cytokeratin 19, SOD2, Eosinophil derived neurotoxin/EDN, Pro-MMP-9, Lubricin, GMNN, 67LR, TRPS1, Dopamine beta Hydroxylase/DBH, ITGB4BP, hnRNP U, IDH1, SynCAM, KIAA1967, CEA, Resistin, Syntaxin 7, NET1, CS, COL19A1, EphB1, EPPK1, C9orf40, LOX, Lymphotoxin beta R/TNFRSF3, Neuropeptide Y, p39, DDT, MCMP2, GNPTG, Angiopoietin-like 2, CIP29, TOP2B, Corticoster-oid-binding globulin, non-muscle Myosin IIA/Myosin, BAFF, C2, Plxdc2, FUCA2, Ube2L3, DMRN9, CARHSP1, GDF9, SMAC, MAGP-2, CYTL1, GARNL1, EMSY, BMPR-IB/ALK-6, PCNA, Apexi, LAMP1, Filamin A, pro-Glucagon, VEGF R1, Beta 2M, IL-10 R alpha, ROS, HE4, ZDHHC18, ALK, CLPS, RPL17, Proteasome subunit beta type 4/PSB4, Ubiquitin, LCMT2, Versican isoform V0, hnRNP A2B1, Envoplakin, GPCR GPR116, LTK, Vasopressin, Vitamin D Receptor, SDF4, TRPC1, CA150, COTL1, HMGN2, NAPRT1, hGH, SMA, Glutamyl hydrolase gamma/CGH, CCL14/HCC-1/HCC-3, GRHPR, Prosaposin, COLEC10, TROPONIN I, MDH2, PSP, Ghrelin, MTUS1, Netrin G2, ALS, Notch-2 ICD, FBP 38, FAK, Intergrin a6, DAN, BLC/BCA-1/CXCL13, Troponin C, PF4V1, G3BP, ADAMDEC1, CCDC126, ACACA, EphA5, Hck, NRG2, hnRNP C1+C2, MYL3, Peroxiredoxin 5, Vitamin K-dependent protein S, PTK 7, UQCRH, SYK, CART, Serpin A4, TXNDC4, Apo (a), APM2, ITGB5, 14-3-3 gamma, Dermcidin, AKR7A2, ORP150, VWF, Cytokeratin 4, GPI, CCDC25, MIP-lb, Midkine, DSPG3, AKAP9, BAD, Apolipoprotein L 2, LMW-PTP/ACP1, EFEMP2, HTRA2, Kallikrein 8, KLF4, EMILIN1, XEDAR, Aconitase 1, CHI3L1, hCGb, DARS2, UPB1, ERp72, HIP1R, BD-1, Ctip2, D4 GDI, CCK, PCPE-1, CRP, Cux2, MAGI2, MyBPC3, ARP2/3, EEF2, Kallikrein 2, Tryptophanyl, LTA4H, PGAM1, PSMA2, alpha 1,2 Mannosidase IA/MAN1A1, Cytokeratin 16, SRMS, GDA, C3orf75, FASTKD5, CETP, DPP3, ARFGEF3, Calpain 1, Csk, Cytokeratin 15, DEFA1/3, Nucleobindin 1/NUCB1, Factor XII, ENO1, BRSK1, fast skeletal Myosin, Factor V, ASXL1, mGLUR5, Cytokeratin 10, ESR1, beta III Tubulin/CUBB3, LDHB, TRPC6, Serotonin, p23, CPA1, Ahsp, Kilon, Protein Z, Calpastatin, BIN2, EphB3, MFI2, Cytokeratin 3, EPHX2, Cytokeratin 5, PCAF, ASK1, CLTA, CNDP1, MPCA, Mimecan, HSC70, Fumarylacetoacetate hydrolase/FAH, GHRF, ADH1B, ITIH1, DNER, MBP, Apelin, LYPA1, and CACNB4.

In some aspects, the at least one ECM component is present at a concentration at least 5× and preferably at least 10× the concentration of the ECM component in a comparable exosome preparation (e.g., prepared via ultra-centrifugation). For example, the exosome composition may comprise one or more of the following ECM components at a concentration at least 20× that of a concentration of the ECM component in a comparable exosome preparation (e.g., prepared via ultra-centrifugation): Cysteine-rich Protein 1, PIM2, Cadherin-13, Beta IG-H3, EG-VEGF/PK1, Cyclophilin A, Dkk-3, BMP-3, QDPR, PAM, EDAR, EGF R/ErbB1, ALCAM, CXCR3, SBP-1, BCMA/TNFRSF17, CCL28/VIC, IL-29, HSP47, VE-Cadherin, I-309, TGF-beta RIII, CCR8, Fractalkine, TCN1, RSU1, uPAR, VEGF-D, PRELP, TGF-beta RII, Thrombopoietin (TPO), Endothelin, S100A6, Angiogenin, TIMP-4, MSP alpha Chain, Activin A, DMGDH, Serpin B8, TRAIL R3/TNFRSF10C, CFHR5, Caspase-14, PRDX 1, FGF-12, CXCR5/BLR-1, Semaphorin 7A, SPINK7, NT-4, TNF RII/TNFRSF1B, 6Ckine, SerRS, Angiostatin, Angiopoietin-like Factor, B7-1/CD80, Protein C, Tcf20, TROY/TNFRSF19, EMAP-II, CSH1, TLR4, RPLPO, ErbB3, RPL11, PGK-1, FGF-16, Plakophilin 1, PRCP, RAGE, Insulin, TSR2, NT-3, USP14, VDAC1/Porin, Proteasome 20S a+b, M-CSF, IL-2, ICAM-1, NEDD8, PRG2, Insulysin/IDE, ICAM-2, MMP-1, Salivary alpha amylase/aAmylase, IL-17F, Galectin-1, Lymphotoxin beta/TNFSF3, TBCA, PREP, VAP-A, Utrophin, YB1, VAP-1, CFHR4, FGF-20, Cyclophilin B, RNASE4, SBSN, FGF R4, FGF-17, PGLS-C-t, Eotaxin-3/CCL26, RREB1, TMEM223, ADAMTS-15, Semenogelin II/SEMG2, C3a, RPL12, GDF8, IGF-II, RPS25, Follistatin-like 1, Smad 5, Notch-2, I-TAC/CXCL11, TRANCE, MMP-3, uPA, WDR1, UQCRB, DR6/TNFRSF21, BMP-15, PSMA4, ErbB4, Gephyrin, beta-NGF, BMP-2, BMP-6, NAP-2, LECT2, FGF-13 1B, Reg3A, CD14, SHIP, RPL5, VEGF, IL-1 F5/FILldelta, RPS28, TUBA6, Endostatin, MMP-9, CK-MB, CapG, IL-11, Ribonuclease A, Eotaxin-2/MPIF-2, GLO-1, TLR3, HGF, Sterol carrier protein 2/SCP2, Visfatin, SHC1, IL-18 R beta/AcPL, SIGLEC14, PRTN3, Contactin-1, CV-2/Crossveinless-2, EDG-1, CXCL14/BRAK, TIMP-3, Serpin A1, Annexin A1, TGM3, CXCR6, PGM1, Osteoprotegerin/TNFRSF11B, Coagulation Factor III/Tissue Factor, M-CSF R, MDC, FAM3B, MMP-11/Stromelysin-3, SCF R/CD117, TGF-beta 5, Titin, sFRP-3, IL-1 beta, HCC-4/CCL16, TRAIL/TNFSF10, Fascin, BNP, ADAMTS-13, PLOD1, FLRG, LDHA, LIF, YY1, NME3, ESAM, RPS19, EpCAM, TAGLN2, CXCL16, BTF3, Hemoglobin subunit beta/HBB, TRADD, Metavinculin, BDNF, Galectin-7, PPP2R4, FACX, PDZD2, IL-26, FGF-9, Fibrinogen-like 2, Plexin B2, Thrombomodulin, Dtk, TRAIL R2/DR5/TNFRSF10B, PNP, ANGPTL8, B7-H3, ACLP, Galectin-3, p73, IL-4, IL-13 R alpha 2, TOB2, Claudin-3, IL-8, VEGF-C, IGF-I SR, Tenascin X(1), Lefty-A, Thrombospondin-1, OSM R beta, SUCLG1, PDGF-AB, IL-6 R, IL-18 BPa, PGAM2, Cripto-1, FGF-23, GSTM1, ICAM-5, RPL10, Ribonuclease Inhibitor, ARTS1, Periostin, UCH-L1, Zyxin, RPL10A, PDLIM5, IL-15 R alpha, FAM3C, Tropomyosin 3, LZTS1, LIGHT/TNFSF14, Osteoadherin(2), SHMT1, CCR9, TWEAK R/TNFRSF12, TPP1, ADAMTS-10, RCL, PCDH7, MIG, SPARC, SH3BGRL, Thrombospondin-4, UFM 1, Prostaglandin D Synthase/PTGDS, GPR-39, SPTBN1, BLVRB, RKIP, 4-1BB, Decorin, CRIM 1, PCSK9, STI1, IL-22 BP, VEGF R2 (KDR), Ficolin-2, CXCR4 (fusin), SIGIRR, IFN-beta, Cyclin D1, MIP-1a, RPS11, Alpha 1 AG, BLAME, Cystatin E/M, GM-CSF R alpha, Uteroglobin(l), Trypsinogeb-2, MCP-3, Erythropoietin R, Proteasome subunit alpha type 6/PSMA6, TGF-alpha, Flt-3 Ligand, Nanog, TNF-alpha, Spectrin beta-5, VNN1, BMP-1, FGF-7/KGF, OSM, FGF R5, Transferrin, C5/C5a, ApoA1, TCP1 eta, Galectin-3BP, PTPRZ, TRAIL R1/DR4/TNFRSF10A, Six3, SORD, CNTF, GDNF, BMPR-II, CXCR2/IL-8 RB, FGF-8, RPS5, CRF21, PGDF/PHGDH, FABP1, SLURP1, CEACAM-8/CD66b, UNC45A, Adiponectin/Acrp30, MMP-25/MT6-MMP, SMC4, Ornithine Carbamoyltransferase/OTC, IFN-gamma RI, CCR4, Proteasome beta 1, Talin1&2, Prohibitin, MMP-24/MT5-MMP, SP-D, Nidogen-2, PTPRS, SIRP beta 1/CD172b, APRIL, ACE-2, IL-6, HGFA, E-Selectin, GATA-4, VEGF R3, UBE2D3, BAFF R/TNFRSF13C, Layilin, Cytokeratin 8, Profilin 1, Cathepsin B, Marapsin, Lymphotactin/XCL1, Nidgen-1, MEP1A, MIF, IL-1 F8/FIL1 eta, MMP-14, HB-EGF, Latent TGF-beta bp1, C8B, SMPD4, ADAMTS-18, FGF Basic, IL-12 R beta 2, MINPP1, URP2, Glycoprotein V, LRG1, ACPP, AlphaA Crystallin/CRYAA, EDA-A2, SH3BGRL3, Serpin F2, CD40 Ligand/TNFSF5/CD154, CPEB3, A2M, Activin B, SREC-II, EGF, FGF-19, Myoferlin, Endoglin/CD105, RECK, ADAM-9, SSEA-4, DDAH1, P-Cadherin, IL-22 R, Glut1, Symplekin, S100A11, SLITRK1, GCP-2/CXCL6, SDPR, IGF-II R, P4HB, TNF-beta, IL-1 R8, IL-1 alpha, Angiopoietin-4, TCCR/WSX-1, GITR/TNFRF18, ILK, TCEB2, RPL22, DEP-1, FGF-18, TL1A/TNFSF15, EphA6, IL-36RN, Tarc, UROC1, Activin C, FASN, PYGL, Somatostatin, Musk, PLA2G1B, IL-1 R3/IL-1 R AcP, FGF-6, IL-18 R alpha/IL-1 R5, Tie-2, NIT2, PF4/CXCL4, TPM1, GDF11, IGFBP-6, Thymopoietin, FUCA1, CRHBP, C1qR1, STAT3, TPM4, Follistatin, Laminin b2, IL-1 sRI, CCR7, ApoA2, ENA-78, Myosin 18B, Desmoplakin, Neurabin 1, FGF-4, PDGF-BB, PCBP2, P20Sb3, IGF2BP1, Chordin-Like 2, UNC-13 Homolog D, Enolase 2, Angiopoietin-2, TFF2(1), RHOC, SUMO3, DGK, HVEM/TNFRSF14, GRO-a, GALNT2, TECK/CCL25, Notch-1, Cystatin S, IL-2 R alpha, WNK2, eIF5A, TrypsinPan, SCF, CD30/TNFRSF8, IL-1 F6/FIL1 epsilon, CutA, CFL1, TRAIL R4/TNFRSF10D, MBD2, UBE2N/Ubc13, PI 16, DANCE, FABP2, IGFBP-4, NEP, NRG1 Isoform GGF2, IL-2 R gamma, MAC-1, MPO, SerpinE2, GDF1, IL-17, Orexin A, Kremen-1, Smad 4, IL-17B R, GCSF, Annexin V, IL-31, TRAP1, Transketolase/TALDO, pIgR, Brgi, BMX, MAN1, Orosomucoid 2, RAPIAB, VEGF-B, SLC38A10, RPS2, RANTES, SerpinB4, Nestin, Complement factor H, MAPRE1, PDGF-AA, RegIA, MUCDHL, SSTR2, IGSF4B, TSG-6, Orexin B, Quiescin Q6, IGFBP-2, IGFBP-rpi/IGFBP-7, Dystroglycan, Alanine Transaminase/ALT, FKBP12, Growth Hormone R (GHR), MCP-1, IL-21, RANK/TNFRSFIIA, HRG-beta 1, ACTC1, Ribonuclease T2, B3GNT1, Src(1), PCYOX1, Leptin R, IL-19, CXCR1/IL-8 RA, PTP mu, IL-1 ra, PDGF-D, HEXB, ERp57, PLC-gamma 1, Nesprin2, Frizzled-4, B7-H2, NAGLU, Serpin B5, TNF RI/TNFRSF1A, IL-1 F9/IL-1 H1, Histone H2B K, OX40 Ligand/TNFSF4, Aminoacylase, Transaldolase 1/TALDO1, Glucagon, IFRD1, sFRP-4, IL-22, Kininostatin/kininogen, PRDM13, CCR5, C 1q, AMPKa1, EXTL2, POR, Smad 8, TXNDC5, IL-17RD, TREM-1, SDNSF, FKBP51, Complement Factor B, Cadherin-6, VCAM-1 (CD106), 11b-HSD1, Tie-1, Vimentin B, DISC 1, RPL7A, GDF-15, IL-31 RA, IL-5 R alpha, p16 ARC, EN-RAGE, Biglycan, DSCAM, Aggrecan, DCI, Cathepsin A, HGFR, sFRP-1, IL-4 R, IL-5, FGF R3, Activin RIA/ALK-2, Prdx6, Cathepsin L, Ezrin, TAXIBP3, FGF-BP, AMICA, KMD4B, Artemin, Ax1, Claudin-4, SDF-1/CXCL12, FADD, MAP1A, ABCF1, Annexin A6, G-CSF R/CD 114, TSLP R, BRCA 2, EphA2, Cystatin SN, Fas Ligand, Pappalysin-1, MEi, 2B4, Fc RIIB/C, Dkk-4, alpha-Synuclein, Neural Cadherin, ANGPTL3, C 1q S, ATBF1/ZFHX3, IGF-I, IL-3, IL-3 R alpha, Semaphorin 6B, DPPIV, LAMP2, Angiopoietin-like 1, ERAP2, PCDX8, ALKP, TMEFF2, IFN-alpha/beta R2, STOM, HSP20, Ck beta 8-1, IL-2 R beta/CD122, NrCAM, MMRN1, OSCAR, IL-21 R, PTMA, BLMH, PLS3, IL-10, CPM, cIAP-2, Pref-1, GASP-1/WFIKKNRP, FAP, Fibrinogen, PPCS, LFA-1 alpha, Mcl-1, DcR3/TNFRSF6B, Mesothelin, TACI/TNFRSF13B, Chemerin, WISP2, GM-CSF, DLL4, TLS/FUS, AGA, BTC, Chromogranin B, HMGB3, CFVII, Cryptic, CCR6, CrkL, 14-3-3 beta, TGF-beta RI/ALK-5, EphA1, Trypsin 1, Lipocalin-1, Podocalyxin, sgp130, Lipocalin-2, Caspase-3, ITIH4 a, FSH, Ras, PTP kappa, TIMP-1, Calsyntenin-1, MARCKS, ARP19, Fibronectin, Activin RIB/ALK-4, Chitobiase, OSBP1, IL-23, IL-12 R beta 1, GCSH, PLOD2, Nectin-3, GRP75, Soggy-1, MIP-3 alpha, GFR alpha-4, HMGB1, PCK2, LRP-1, MMP-8, HSP70, EPCR, Epiregulin, Gasi, CTLA-4/CD152, IL-27, TGF-beta 1, Attractin, BNIP2, BMP-5, PKLR, CCR3, Histone H2A, PDGF-C, IL-17B, Osteoactivin/GPNMB, CPE, CD40/TNFRSF5, CA1, Triosephosphate isomerase/TPIS, ADAMTS-17, EYA2, GFR alpha-1, Amylin, DMP-1, NUP98, SERPING1, CKB, CCR2, pro-MMP13, ApoC1, Glucose 6 Phosphate Dehydrogenase/G6PD, Caldesmon/CALD1, TLR2, NGF R, PSA-Free, COCO, MRP 1, MCAM, GRP78, IL-9, IL-1 R9, NAIP, RBP4, PABP, CEACAM-1, ADAMTS-5, ALPP, GPX1, Cathepsin X/Z/P, ApoB, Contactin-2, LRP-6, MMP-2, MFRP, Survivin, Siglec-1, PD-ECGF, cTnT, Thioredoxin-1, PGD, RPS23, TPX, LAMP, Myotrophin, SSTR5, IP-10, PGRPL, GDF7, FAM20C, ARFBP1, Activin RIIA, Sonic Hedgehog (Shh N-terminal), ApoC2, CFI, Adipsin, C7, ApoM, HRG, Fibulin 3, HINT1, GPBB, GDF5, Histone H1.3, RELM beta, glutathione S transferase Omega 1/GSTO1, Serpin A3, ErbB2, XIAP, IBSP, MICA, Desmocollin-3, Prolactin, Leptin (OB), WISP-1/CCN4, Aldolase B, NPAS3, LOX-1, hnRNP G, PACS1, BIK, Glycerol 3 Phosphate Dehydrogenase, Olfactomedin-2, GFR alpha-2, MSH6, ANGPTL4, Prouroguanylin, PHAP1, FKBP25, BMP-8, CFHR 1, Osteocalcin, HBZ, HOXD11, LEDGF, NeuroD1, RanGAP1, NF-M, SOX17, PYY, IL-20, Cytochrome c, IL-15, CA 15-3, Hemoglobin, DCBLD2, Serpin I1, DLL1, FGF-21, RNASE6, Annexin A7, PCCA, GLIPR2, Desmuslin, C9, Proteasome 20S b7, ARX, LIF R alpha, C1s, Chymase, Prion protein PrP/PRNP, IFN-gamma, CNOT1, UROD, IL-1 R6/IL-1 Rrp2, PER1, CFHR2, Thymidine Kinase-1, PTP gamma, LBP, BCAM, NM23-H1/H2, Lysozyme, Frizzled-5, PARC/CCL18, ROR1, Serpin A8, Persephin, IL-13 R alpha 1, IGFBP-3, Neurturin, perilipin 3, PSMB5, PLUNC, Cathepsin G, Siglec-9, MMP-15, Frizzled-7, ARB1, CL-P1, Glypican 3, MFG-E8, GATA-3, Frizzled-6, beta B1 Crystallin/CRYBB1, Siglec-5/CD170, TOPORS, PIN, Hemoglobin A1c, S100A8, EphB4, CLC, Cystatin A, Transthyretin, GSR, GAPDH, Trappin-2, Plastin L, PSMA1, Cathepsin S, IGFBP-5, LILRA3, GITR Ligand/TNFSF18, KRT31, KCTD10, BTD, LYVE-1, ACE, ECM-1, ZNF671, FoxP3, ROBO4, Cystatin C, BIRC6, Vitronectin, beta-Catenin, beta-I Tubulin, E-Cadherin, IL-1 sRII, Plectin, Spinesin, Endorepellin, Glut2, Insulin R, Serpin D1, Azurocidin, RPS10, Catalase, Glut5, HAI-2, FGFR1 alpha, S100A4, ARPC3, Properdin, Glyoxalase II, Netrin-4, FABP3, ZBTB4, LIMPII, Neuritin, BMP-3b/GDF-10, Vasorin, Cortactin, Cystatin D, Smad 1, MCP-4/CCL13, Syndecan-1, Osteopontin, ApoE, APN, IFN-alpha/beta R1, Fas/TNFRSF6, Erythropoietin, ApoB100, Cathepsin H, TWEAK/TNFSFi2, Chordin-Like 1, Pentraxin3/TSG-14, AFP, CD61, Cathepsin D, DOT1L, Desmocollin-2, URB, PRSS3, MASP3, ADAMTS-19, Ephrin B1, TGF-beta 3, ApoH, ALDHIAI, Nectin-1, GFAP, KLK-B1, Secretogranin V/SCG5, Peroxiredoxin 3, EphB6, MYHC, NABC1, PSMD1, AgRP, IL-23 R, Galanin, PIK3IP1, IL-1 F10/IL-1HY2, IL-28A, SOX4, ANK, PON1, Uromodulin, PPOX, Histone H4, Metallothionein, FOLR3, Neurokinin-A, Protein p65, IL-33, HDGF, APLP-1, Frizzled-3, PGRP-S, SOD4, SERPINBI, Tenascin C, GMF beta, Fyn, HPR, Neuropilin-2, Lamin A+C, ZC3H4-N-t, GSTP1, PON2, DCXR, GRO, Homerin, COX-2, S100A10, 53BP1, PKM2, 5-100b, Lamin B1, PZP, Chitotriosidase, Osteocrin, PlGF, LOK, ALBUMIN, SHANK1, TLR1, HADHA, ApoD, PA2G4, KIF3B, Ubiquitin+1, TXNRD2, Eotaxin/CCL11, HCFC1, IL-20 R beta, Pancreastatin, FGF-10/KGF-2, Brevican, CES1, TIMP-2, MMP-10, CD30 Ligand/TNFSF8, GIP, Kallikrein 10, Ficolin-3, HNF-3 alpha/FoxA1, Thyroglobulin, TFPI, ICAM-3 (CD50), RPL14, S100A9, CA2, Hoxb3, Serpin A9, IL-20 R alpha, TFF1, Pro-BDNF, NCAM2, NPTXR, Guanylin, ALP, TMEFF1/Tomoregulin-1, PSA-total, KIAA1468, IL-7 R alpha, HSP10, GASP-2/WFIKKN, SLPI, Neogenin, Cerberus 1, PSMA7, Beta Defensin 4, FIH, CHC17, Semenogelin I/SEMG1, hHR23b, Proteasome 20S alpha, Histone H3.3, SOST, EV15L, Fetuin A, Fetuin B, GULP1/CED-6, WIF-1, GDF3, INSL3, APC, TSLP, ROCK1, TRA-1-60, HOXA10, MYH7, ACLY, EVC2, CTGF/CCN2, TRA-1-81, 14-3-3 sigma, NELL2, Ferritin, Cytochrome C, B3GNT2, Fibrinopeptide A, PISD, SAMSN1, Glut3, HSP40, PD-1, PDGF R beta, SNCG, ROCK2, CRTH-2, MP1, CD200, PDIA6, Grb2, CNTF R alpha, F11, Frizzled-1, BMP-9, ROR2, L-Selectin (CD62L), Clusterin, AKR1C3, NCAM-1/CD56, S100P, COMP, FGFR1, PARK7, Laminin 2 alpha, PI 3-Kinase C2 beta, IRE1, Filamin B, NT5C3, Lumican, FGFR2, AIF, IL-34, Multimerin 2, Latent TGF beta bp2, ADM, Inhibin beta, FOLR1, SET, Progranulin, RELM alpha, Endothelin Receptor A, FABP4, PPP2R5C, ApoE3, MN1, RPS12, MLCK, INSRR, 14-3-3 epsilon, HP1BP3, Perilipin-1, Furin, ABL1, Mannosidase II, IL-17E, Grainyhead-like protein 1 homolog/GRHL1, Neurotrimin, CLIC1, LOXL1, 14-3-3 theta, RhoGDI, ACTH, Afamin, FBPase 1, Plasminogen, Kallikrein 11, Desmoglein-1, Myoglobin, Contactin-4, PECAM-1/CD31, ADH1C, ATP50, and any combination thereof.

In still further aspects, the at least one ECM component is present at a concentration at least about 5 times, preferably at least about 20 times the concentration of the ECM component in a comparable exosome preparation (e.g., prepared via ultra-centrifugation). For example, the exosome composition may comprise one or more of the following components at a concentration at least 20× that of a concentration of the ECM component in a comparable exosome preparation (e.g., prepared via ultra-centrifugation): Cysteine-rich Protein 1, PIM2, Cadherin-13, Beta IG-H3, EG-VEGF/PK1, Cyclophilin A, Dkk-3, BMP-3, QDPR, PAM, EDAR, EGF R/ErbB1, ALCAM, CXCR3, SBP-1, BCMA/TNFRSF17, CCL28/VIC, IL-29, HSP47, VE-Cadherin, 1-309, TGF-beta RIII, CCR8, Fractalkine, TCN1, RSU1, uPAR, VEGF-D, PRELP, TGF-beta RII, Thrombopoietin (TPO), Endothelin, S100A6, Angiogenin, TIMP-4, MSP alpha Chain, Activin A, DMGDH, Serpin B8, TRAIL R3/TNFRSF10C, CFHR5, Caspase-14, PRDX 1, FGF-12, CXCR5/BLR-1, Semaphorin 7A, SPINK7, NT-4, TNF RII/TNFRSF1B, 6Ckine, SerRS, Angiostatin, Angiopoietin-like Factor, B7-1/CD80, Protein C, Tcf20, TROY/TNFRSF19, EMAP-II, CSH1, TLR4, RPLPO, ErbB3, RPL11, PGK-1, FGF-16, Plakophilin 1, PRCP, RAGE, Insulin, TSR2, NT-3, USP14, VDAC1/Porin, Proteasome 20S a+b, M-CSF, IL-2, ICAM-1, NEDD8, PRG2, Insulysin/IDE, ICAM-2, MMP-1, Salivary alpha amylase/aAmylase, IL-17F, Galectin-1, Lymphotoxin beta/TNFSF3, TBCA, PREP, VAP-A, Utrophin, YB1, VAP-1, CFHR4, FGF-20, Cyclophilin B, RNASE4, SBSN, FGF R4, FGF-17, PGLS-C-t, Eotaxin-3/CCL26, RREB1, TMEM223, ADAMTS-15, Semenogelin II/SEMG2, C3a, RPL12, GDF8, IGF-II, RPS25, Follistatin-like 1, Smad 5, Notch-2, I-TAC/CXCL11, TRANCE, MMP-3, uPA, WDR1, UQCRB, DR6/TNFRSF21, BMP-15, PSMA4, ErbB4, Gephyrin, beta-NGF, BMP-2, BMP-6, NAP-2, LECT2, FGF-13 1B, Reg3A, CD14, SHIP, RPL5, VEGF, IL-1 F5/FILldelta, RPS28, TUBA6, Endostatin, MMP-9, CK-MB, CapG, IL-11, Ribonuclease A, Eotaxin-2/MPIF-2, GLO-1, TLR3, HGF, Sterol carrier protein 2/SCP2, Visfatin, SHC1, IL-18 R beta/AcPL, SIGLEC14, PRTN3, Contactin-1, CV-2/Crossveinless-2, EDG-1, CXCL14/BRAK, TIMP-3, Serpin A1, Annexin A1, TGM3, CXCR6, PGM1, Osteoprotegerin/TNFRSF1 IB, Coagulation Factor III/Tissue Factor, M-CSF R, MDC, FAM3B, MMP-11/Stromelysin-3, SCF R/CD117, TGF-beta 5, Titin, sFRP-3, IL-1 beta, HCC-4/CCL16, TRAIL/TNFSF10, Fascin, BNP, ADAMTS-13, PLOD1, FLRG, LDHA, LIF, YY1, NME3, ESAM, RPS19, EpCAM, TAGLN2, CXCL16, BTF3, Hemoglobin subunit beta/HBB, TRADD, Metavinculin, BDNF, Galectin-7, PPP2R4, FACX, PDZD2, IL-26, FGF-9, Fibrinogen-like 2, Plexin B2, Thrombomodulin, Dtk, TRAIL R2/DR5/TNFRSF10B, PNP, ANGPTL8, B7-H3, ACLP, Galectin-3, p73, IL-4, IL-13 R alpha 2, TOB2, Claudin-3, IL-8, VEGF-C, IGF-I SR, Tenascin X(1), Lefty-A, Thrombospondin-1, OSM R beta, SUCLG1, PDGF-AB, IL-6 R, IL-18 BPa, PGAM2, Cripto-1, FGF-23, GSTM1, ICAM-5, RPL10, Ribonuclease Inhibitor, ARTS1, Periostin, UCH-L1, Zyxin, RPL10A, PDLIM5, IL-15 R alpha, FAM3C, Tropomyosin 3, LZTS1, LIGHT/TNFSF14, Osteoadherin(2), SHMT1, CCR9, TWEAK R/TNFRSF12, TPP1, ADAMTS-10, RCL, PCDH7, MIG, SPARC, SH3BGRL, Thrombospondin-4, UFM 1, Prostaglandin D Synthase/PTGDS, GPR-39, SPTBN1, BLVRB, RKIP, 4-1BB, Decorin, CRIM 1, PCSK9, STI1, IL-22 BP, VEGF R2 (KDR), Ficolin-2, CXCR4 (fusin), SIGIRR, IFN-beta, Cyclin D1, MIP-1a, RPS11, Alpha 1 AG, BLAME, Cystatin E/M, GM-CSF R alpha, Uteroglobin(1), Trypsinogeb-2, MCP-3, Erythropoietin R, Proteasome subunit alpha type 6/PSMA6, TGF-alpha, Flt-3 Ligand, Nanog, TNF-alpha, Spectrin beta-5, VNN1, BMP-1, FGF-7/KGF, OSM, FGF R5, and Transferrin.

In still further aspects, the exosome composition may comprise ECM component at a concentration at least 5× and preferably at least 30× the concentration of the ECM component in a comparable exosome preparation(e.g., prepared via ultra-centrifugation). For example, the exosome composition may comprise one or more of the following ECM components at a concentration at least 30× the concentration of the ECM component in a comparable exosome preparation (e.g., prepared via ultra-centrifugation): Cysteine-rich Protein 1, PIM2, Cadherin-13, Beta IG-H3, EG-VEGF/PK1, Cyclophilin A, Dkk-3, BMP-3, QDPR, PAM, EDAR, EGF R/ErbB1, ALCAM, CXCR3, SBP-1, BCMA/TNFRSF17, CCL28/VIC, IL-29, HSP47, VE-Cadherin, 1-309, TGF-beta RIII, CCR8, Fractalkine, TCN1, RSU1, uPAR, VEGF-D, PRELP, TGF-beta RII, Thrombopoietin (TPO), Endothelin, S100A6, Angiogenin, TIMP-4, MSP alpha Chain, Activin A, DMGDH, Serpin B8, TRAIL R3/TNFRSF10C, CFHR5, Caspase-14, PRDX 1, FGF-12, CXCR5/BLR-1, Semaphorin 7A, SPINK7, NT-4, TNF RII/TNFRSF1B, 6Ckine, SerRS, Angiostatin, Angiopoietin-like Factor, and B7-1/CD80.

In still further aspects, the exosome composition may comprise one or more ECM component at a concentration at least 5× and preferably at least 40× a concentration of the ECM component in a comparable exosome preparation (e.g., prepared via ultra-centrifugation). For example, the exosome composition may comprise one or more of the following ECM components at a concentration at least 40× the concentration of the ECM component in a comparable exosome preparation (e.g., prepared via ultra-centrifugation): Cysteine-rich Protein 1, PIM2, Cadherin-13, Beta IG-H3, EG-VEGF/PK1, Cyclophilin A, Dkk-3, BMP-3, QDPR, PAM, EDAR, EGF R/ErbB1, ALCAM, CXCR3, and SBP-1.

In still further aspects, the exosome composition may comprise one or more ECM component at a concentration at least 5× and preferably at least 50× a concentration of the ECM component in a comparable exosome preparation (e.g., prepared via ultra-centrifugation). For example, the exosome composition may comprise one or more of the following ECM components at a concentration at least 50× the concentration of the ECM compound in a comparable exosome preparation (e.g., prepared via ultra-centrifugation): Cysteine-rich Protein 1, PIM2, Cadherin-13, Beta IG-H3, EG-VEGF/PK1, and Cyclophilin A.

The concentration of any of the previous factors may be determined by one of skill in the art using standard techniques. For example, any of the factors listed above may be analyzed and quantified using standard proteomics (e.g., using mass spectrometry or other suitable analytical methods).

In any of the compositions provided herein, concentrations of one or more components may be compared to a "comparable exosome preparation". As used herein a "comparable exosome preparation" refers to a purified exosome composition prepared using standard methods. Standard or traditional methods for purifying exosomes usually involves several centrifugation steps, each with increasing force. For example, one protocol to purify exosomes from a low viscosity mixture (e.g., urine or conditioned medium) is described in Dismuke et al., ("Current Methods to Purify and Characterize Exosomes" *Mesenchymal Stem Cell Derived Exosomes: The Potential for Translational Medicine*: Chapter 4. Edited by Yaoliang Tang and Buddhadeb Dawn. Academic Press, 2015) which is incorporated herein by reference in its entirety. As described, a multi-step process is followed where first a low-speed centrifugation step is applied to remove nonadherent cells, dead cells, and cellular debris followed by a high-speed centrifugation step to pellet exosomes. The initial exosomal pellet fraction may then undergo subsequent rounds of centrifugation to continue to purify the exosome composition. This sequential centrifugation process is also known as "ultra-centrifugation". In contrast, the methods provided herein do not involve centrifugation. In certain aspects, the comparable exosome preparation may comprise a commercially available preparation (e.g., AMNIOSOMES as manufactured by Thrivell).

The exosome compositions provided herein may be provided in one or more unit dosages each comprising a concentration of exosomes that may be administered to a subject in order to treat a disease or disorder.

In various aspects, a unit dosage of the exosome composition may comprise about 500 million to about 500 billion exosomes. For example, the unit dosage may comprise about 500 million to about 5 billion exosomes, about 500 million to about 4.5 billion, about 500 million to about 4 billion, about 500 million to about 3.5 billion, about 500 million to about 3 billion, about 500 million to about 2.5 billion, about 500 million to about 2 billion, about 500 million to about 1.5 billion, about or about 500 million to about 1 billion. In other aspects, the unit dosage may comprise about 1 billion to about 5 billion, about 1 billion to about 4.5 billion, about 1 billion to about 4 billion, about 1 billion to about 3.5 billion, about 1 billion to about 3 billion, about 1 billion to about 2.5 billion, about 1 billion to about 2 billion exosomes. In further aspects, the unit dosage may comprise about 2 billion to about 5 billion, about 2 billion to about 4.5 billion, or about 2 billion to about 3 billion exosomes. In still other aspects, the unit dosage may comprise about 3 billion to about 4 billion exosomes, from about 3 billion to about 4.5 billion, or about 3 billion to about 5 billion exosomes. In some aspects, the unit dosage may comprise about 4 to 5 billion exosomes.

In further aspects, the unit dosage of the exosome composition may comprise about 15 billion to about 25 billion exosomes. For example, the unit dosage may comprise about 15 billion to about 25 billion, about 15 billion to about 20 billion, about 15 billion to about 18 billion, about 20 billion to about 25 billion, about 23 billion to about 25 billion. In still further aspects, the unit dosage may comprise about 75 billion to about 500 billion exosomes. For example, the unit dosage may comprise about 75 billion to about 450 billion, about 75 billion to about 400 billion, about 75 billion to about 350 billion, about 75 billion to about 300 billion, about 75 billion to about 250 billion, about 75 billion to about 200 billion, about 75 billion to about 150 billion, or about 75 billion to about 100 billion exosomes. In some aspects, the unit dosage may comprise about 100 billion to about 500 billion, about 150 billion to about 500 billion, about 200 billion to about 500 billion, about 250 billion to about 500 billion, about 300 billion to about 500 billion or about 450 billion to about 500 billion exosomes.

In certain aspects, a unit dosage of exosome composition may comprise about 300 billion to about 500 billion exosomes.

In still other aspects, a unit dosage of the exosome composition may comprise about 3 billion exosomes. In some aspects, a unit dosage of the exosome composition may comprise about 10 billion exosomes. In some aspects, a unit dosage of the exosome composition may comprise about 15 billion exosomes.

In some aspects, a unit dosage of the exosome composition may comprise about 100 billion exosomes. In some aspects, a unit dosage of the exosome composition may comprise about 200 billion exosomes. In some aspects, a unit dosage of the exosome composition may comprise about 300 billion exosomes. In some aspects, a unit dosage of the exosome composition may comprise about 400 billion exosomes. In some aspects, a unit dosage of the exosome composition may comprise about 500 billion exosomes.

Also provided herein are MSC compositions comprising one or more mesenchymal stem cells. The MSC compositions provided herein are products of the same method used to derive the exosome compositions as described below. Further the MSC compositions may be provided in one or more unit-dosages each comprising a defined number of mesenchymal stem cells suitable for administration to treat a disease, disorder or condition in a subject in need thereof.

Any compositions described herein (e.g., exosome composition or MSC composition) and any unit dosage of the composition may comprise at least one excipient. Suitable excipients include pharmaceutically acceptable excipients, such as diluents, binders, fillers, buffering agents, pH modifying agents, disintegrants, dispersants, preservatives, lubricants, taste-masking agents, flavoring agents, coloring agents, or combinations thereof. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, or saccharides.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts or crystalloid medias (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative or cryo-preservative. Non-limiting examples of suitable preservatives or cryo-preservatives include antioxidants, such as BHA, BHT, vitamin A, vitamin C, vitamin E, or retinyl palmitate, citric acid, sodium citrate; chelators such as EDTA or EGTA; Cryo preservatives; such as Dimethyl sulfoxide (DMSO), sugars for preservatives or cryo-preservatives; such as Trehalose, heta-starch, sucrose, and antimicrobials; such as parabens, chlorobutanol, or phenol.

In further aspects, any composition provided herein (e.g., the exosome composition or the MSC composition) may be further processed (e.g., as a powder) using lyophilization. Suitable methods of preparing lyophilized compositions are known in the art. Suitable excipients that may be used to prepare lyophilized compositions may include cryo-preservatives such as Trehalose, beta-starch, and sucralose.

In various aspects, the exosome compositions and the MSC compositions provided herein may be prepared by a method comprising sequentially isolating exosomes and at least one component isolated from an extracellular matrix from a wildtype tissue sample or cell culture comprising mesenchymal stem cells using a tandem tangential flow filtration system. Suitable tandem tangential flow filtration systems and methods of using them are provided below.

II. Methods of Making

Isolation Method

The present method provides substantially undamaged and pure exosomes isolated from a liquid culture of human mesenchymal stem cells. One simplified example of this method is summarized in FIG. 1. It is understood that this simplified flow chart may not explicitly list every step useful for obtaining an exosome product.

The MSC culture may be derived from explants of adult and embryonic tissues, such as adipose tissue, muscle, peripheral blood, lung, heart, corneal stroma, dental pulp, placenta, umbilical cord, endometrium, amniotic membrane, and Wharton's jelly, by any method known in the art. For example, MSCs can be obtained from explants of human placental or umbilical cord tissue according to the method of Wu et al. (Scientific Reports (2018) 8:5014). Some exemplary useful MSC tissue sources include umbilical cord, as MSCs from this tissue have similar immune phenotype and multilineage differentiation, but higher expansion potential relative to bone marrow MSCs and adipose-derived MSCs, and Wharton's jelly. Wharton's jelly (substantia gelatinea-funiculi umbilicalis), a gelatinous substance within the umbilical cord, derived from extra-embryonic mesoderm, can be commercially obtained, and MSCs can be isolated from it via e.g., the enzymatic, enzymatic-explant, and explant methods (see, e.g., Vara I (2019) Iran J. Med. Sci. 44(6):437-448).

Liquid MSC cultures of any size can be produced by expanding the original MSC source in a growth medium to any volume which will provide a useful number of exosomes.

The MSCs are removed from the liquid culture by any method known in the art, such as, but not limited to, by centrifugation, gravity filtration, density filtration, syringe filtration, vacuum filtration, column filtration, column chromatography, etc.

For example, the MSCs can be removed from the culture medium by gravity filtration through a prefilter having a pore size of at least 0.4 µm, e.g., about 0.4 µm to about 10 µm. The prefilter can be in the form of a module comprising one or more individual prefilters. For example, the MSC culture medium can be subjected to filtration through a gravity prefilter module comprising a prefilter having a pore size of about 100 µm, followed by a series of prefilters with decreasing pore size, such as a prefilter having a pore size of at least about 0.4 µm, such as about 8.0 µm, about 0.8 µm, and/or about 0.45 µm. These prefilters can be made of any commercially available or other material with the desired pore size, and which does not have any attractive or repulsive characteristics. One nonlimiting, useful prefilter material comprises polypropylene.

The cell-free medium is then processed by tangential flow filtration to obtain the exosomes produced and secreted in the culture medium by the MSCs before the cells are removed from the liquid culture medium. Exosome collection is accomplished by filtering the cell-free culture medium through a commercially obtainable first hollow fiber filter having a pore size of about 0.1 µm to about 1.0 µm to obtain a permeate. For example, the hollow fiber filter maybe a hollow fiber filter having a pore size of about 0.1 µm, about 0.1 µm, about 0.2 µm, about 0.3 µm, about 0.4 µm, about 0.5 µm, about 0.6 µm, about 0.65 µm, about 0.7 µm, about 0.8 µm, about 0.9 µm, or 1.0 µm.

The permeate of the first hollow fiber filter is then subjected to diafiltration through a hollow fiber filter having a pore size of about 30 kD to about 600 kD, about 60 kD to about 600 kD, about 40 kD to about 150 kD, about 60 kD to about 150 kD to obtain a retentate which contains the exosomes. For example, the permeate may be subjected to diafiltration through a second hollow fiber filter tube having a pore size of about 30 kD, about 40 kD, about 50 kD, about 60 kD, about 70 kD, about 80 kD, about 90 kD, about 100 kD, about 110 kD, about 120 kD, about 130 kD, about 140 kD, about 150 kD, about 200 kD, about 250 kD, about 300 kD, about 350 kD, about 400 kD, about 450 kD, about 500 kD, or about 600 kD.

Optionally, the permeate from the first hollow fiber filter may be filtered through an intermediate hollow fiber filter tube have a pore size of about 0.45 µm to about 2.0 µm, about 0.5 µm, about 0.6 µm, about 0.70 µm, about 0.8 µm, about 0.9 µm, about 1.0 µm, about 1.1 µm, about 1.2 µm, about 1.3 µm, about 1.4 µm, about 1.5 µm, about 1.6 µm, about 1.70 µm, about 1.8 µm, about 1.9 µm, or about 2.0 µm to obtain a second permeate which is then subjected to diafiltration through the second hollow fiber filter.

These hollow fiber filters may be in any form, such as, but not limited to, a tube or cassette. These filters comprise polysulfane, polysulfone, and/or "modified" polysulfone, such as, but not limited to, polyethersulfone (see, e.g., (Repligen, Waltham, MA) or the addition of amine and/or sulfonyl groups. The final retentate from the second hollow fiber filter comprises or consists substantially of, the collected exosomes.

The amount or yield of exosomes in the retentate can be estimated as follows: A single MSC produces about 1,000 to about 2,200 exosomes per day in a typical MSC growth medium Thus about $3 \times 10^9$ can be obtained from a 15 liter bioreactor MSC culture. For commercial purposes, a useful amount of MSCs are grown to provide a sufficient number of exosome from which a therapeutic product can be made. The present method provides a yield of about 32 trillion to about 50 trillion exosomes from a culture of about 7 billion to about 10 billion mesenchymal stem cells. For example, about 42 trillion exosomes can be expected to be secreted and harvested from about $9 \times 10^9$ MSCs. In another example, from about $10 \times 10^6$ MSCs from an umbilical cord sample, expanded to about $9 \times 10^6$ MSCs secrete into the cell medium of the bioreactor about $42 \times 10^{12}$ exosomes before the isolation procedure is initiated.

A dissected sample of the umbilical cord tissue which will be used to obtain MSC exosomes was examined by flow cytometry to see what type of cells were in the sample. This method validates the identity of the cells by detecting the expression of certain expected enzymatic and other antigenic markers on the MSC surface. The dissected tissue sample was then cultured and expanded in a growth medium. A sample of the expanded cell culture medium was then subjected to flow cytometry and examined for the expression of certain MSC surface markers to determine the identity of the cells in the culture. It was found that the expanded cells are MSCs. An exosomal sample from the retentate obtained from this MSC sample was also examined to determined is the exosomes from these MSCs expressed certain expected MSC markers (CD20, CD34, CD45, CD73, CD90, CD105, CD166, and HLA-DR). It was determined that the exosomes do express these markers and thus are viable.

That the MSC exosomes isolated by the present method and system are substantially undamaged and pure can be determined by any exosomal characterization method known in the art, e.g., nanoparticle tracking analysis, exosomal surface marker-based characterization by flow cytometry, fluorescence-activated cell sorting (FACS), Western blotting, enzyme-linked immunosorbent assay (ELISA), MA-based characterization, Tunable Resistance Pulse Sensing (TRPS) characterization. At least some of these methods track the presence of the markers such as CD20, CD34, CD45, CD73, CD90, CD105, CD166, and HLA-DR expected to be on viable exosomes.

Exosome yield can be determined from a sample of the retentate by any method known in the art (see, Koritzinsky (2017) J. Cell Physiol. 232(7):1587-1590), e.g., by particle counting systems such as Izon qEV and TRPS systems, Nanosight's Nanoparticle's Nanoparticle Tracking Analysis, Tunable Resistive Pulse Sensing, by vesicle flow cytometry, Surface Plasmon resonance, or by electron microscopy.

Exosomal Isolation System

The present disclosure also provides a system for obtaining a plurality of exosomes from a source of cell-free MSC culture medium. As disclosed herein, exosomes can be obtained from a cell-free liquid MSC culture by the method and using the system of the present disclosure.

In general, the system may comprise a first tangential flow filter (TFF) in communication with the source of cell-free culture medium. The first TFF generates a retentate and a permeate. The system may further comprise a second TFF. The input of the second TFF is in direct or indirect fluid communication with the permeate of the first TFF. The second TFF also generates a retentate and a permeate, the latter comprising the plurality of exosomes.

Optionally, the presently disclosed system may additionally comprise an intermediate TFF. An input of the intermediate TFF may be in direct or indirect fluid communication with a permeate output of the first TFF and a retentate output of the intermediate TFF may be in direct or indirect fluid communication with the input of the second TFF.

The source of cell-free culture medium may take a variety of forms, including that of a system for prefiltration. Without limitation, the presently disclosed system may or may not include such a system for prefiltration. If employed, the prefiltration system is in communication with the MSC liquid culture and provides the cell-free culture medium.

In addition, the presently disclosed system is not limited by the equipment required or process practiced to achieve the MSC liquid culture.

Various elements useful in implementing the presently disclosed system are also shown and described in illustrative embodiments. For example, feed vessels may be employed for providing fluid input to the first and second TFFs. Various pumps may also be employed to propel fluid throughout portions of the presently disclosed system. Further, a diafiltration reservoir may provide a source of diafiltration buffer with respect to the second TFF.

An optional and illustrative system for obtaining a cell-free mesenchymal stem cell (MSC) liquid culture is described. Human placental and/or umbilical cord tissue is processed according to known techniques in order to isolate MSCs, which are then plated. The cell culture is then harvested prior to introduction into a suitable bioreactor. Cell culture expansion may be repeated as desired or required.

Cell culture expansion occurs in growth medium within the bioreactor for a period of time. In an exemplary embodiment, this time period is five to six days. The cell culture may then be introduced into a subsequent bioreactor containing collection medium for a period of time which, in an illustrative embodiment is three to four days. The MSC culture medium is then collected and processed for cell removal.

An optional and illustrative system for prefiltration of MSCs for cell removal is disclosed, though it is emphasized that a variety of prefiltration equipment may be utilized to achieve satisfactory cell removal results.

The culture introduced to an optional gravity filter which, in one exemplary embodiment, contains a filtered media. Suitable pore sizes may be utilized, and other preliminary filtration techniques may also be practiced, as desired or as necessary.

Next, the MSC culture medium may be passed through a prefilter module. In various aspects, the prefilter module may comprise sequence of discrete prefilters, each having a successively smaller filter pore size. The filtrate of an upstream prefilter is introduced into the subsequent prefilter in order to achieve an ultimate filtrate that is cell-free. Three prefilters are shown, though a different number may be utilized. Alternatively, the illustrated prefilters may be replaced with one or more additional gravity filters or with one or more centrifuge systems.

These prefilters may in one embodiment have filter media formed of polypropylene, and of polypropylene fleece, in particular.

One or more pumps in association the prefilter module may be used due to the small pore size required for cell removal. Thus, in the illustrated embodiment, there is one pump for pumping cell culture into each of the discrete prefilters. These pumps may be, for example, peristaltic pumps.

The cell-free filtered MSC medium is then introduced into a feed vessel. The feed vessel may be provided as a large container having a capacity of, for example, 15 liters. Alternatively, a smaller feed vessel may be employed along with an auxiliary vessel, such as the illustrated bleed vessel. In the illustrated embodiment, the cell-free filtered MSC medium is distributed between these two vessels.

A pump associated with the first feed vessel is then utilized to initially pump the filtered cell-free MSC medium to the input of a first tangential flow filter (TFF). In the illustrated embodiment, the first TFF is a hollow-fiber filter tube (HFT) TFF though other hollow fiber filter formats may be employed as with respect to the first TFF, other hollow fiber filter formats may be employed.

The permeate of the first TFF is accumulated into a collection vessel to form a source of concentrated product. An auxiliary pump may be employed to accumulate the permeate of the first TFF.

Meanwhile, the retentate from the first TFF is recycled into the first feed vessel. If an auxiliary feed vessel is employed for collecting the filtered, cell-free MSC medium, the retentate may be mixed with additional filtered medium. The process of filtering the retentate or combination of retentate and filtered medium continues until a sufficient concentration of permeate has been collected in the collection vessel.

The concentrated product from the permeate of the first TFF may then provided to the input of a second TFF via a second feed vessel. The collection vessel and the second feed vessel may in one embodiment be discrete containers. The collection vessel and the second feed vessel may in one embodiment be the same vessel. The second TFF may beanother HFT TFF A pump may be utilized for the purpose of providing the concentrated product from the second feed vessel to the input of the second TFF. This pump, as well as the pump associated with the first feed vessel, may be a peristaltic pump in one non-limiting embodiment The permeate of the second TFF is directed to a waste container as the product in the retentate is again flowed through the second TFF via the second feed vessel.

A diafiltration reservoir is in fluid communication with the second feed vessel for enabling diafiltration through the second TFF. Diafiltration buffer, such as saline, selectively flows from the diafiltration reservoir into the second feed vessel, replacing the fluid that exits the second TFF as permeate. An auxiliary pump may be utilized to selectively convey the diafiltration buffer into the second feed vessel. Such an auxiliary pump may be a peristaltic pump, for example, though other pump types may be employed.

In an embodiment, the diafiltration reservoir volume is sufficient to retain a volume of diafiltration buffer that is five to ten times the volume of the accumulated, concentrated permeate from the first TFF. Thus, in this embodiment, the second TFF retentate may be washed through five to ten diafiltration volumes (DVs). Other quantities of diafiltration buffer may be employed, however.

Once diafiltration is complete, the second TFF retentate is again recycled to the second feed vessel then back to the input of the second TFF until a desired degree of concentration of the desired exosome product has been achieved. The final product comprising concentrated exosomes is then collected in the second feed vessel. Fluid valves may be utilized to redirect unwanted fluid into a suitable waste container for collection. Another auxiliary pump may be provided for the purpose of waste collection.

Optionally, a third TFF, which may be referred to as an intermediate TFF, may be disposed in fluid communication intermediate the second feed vessel and associated second pump and the second TFF. The intermediate TFF may be an HFT TFF. The output from the second feed vessel is in fluid communication with the input of the intermediate TFF, if used, via the respective pump. The permeate from the intermediate TFF is directed to a waste stream as the product in the retentate of the intermediate TFF is provided to the input of the second TFF, in this alternative embodiment. Diafiltration and concentration, as previously described, thus takes place within the intermediate TFF as well, if used.

The hollow fiber filter tubes of one or more of the first, second, and intermediate TFFs may be provided as polysulfane, polysulfone, and/or modified polysulfone.

A simplified flow chart of the steps involved in utilizing a system described above is provided in FIG. 1. It is understood that this simplified flow chart may not explicitly list every step useful for obtaining an exosome product. For example, the simplified chart does not address use of an intermediate HFT TFF, as discussed above.

In a first step 100, human placental and/or umbilical cord tissue is processed in order to isolate mesenchymal stem cells (MSCs). The MSCs are then cultured and expanded 102, and a cell-free MSC culture medium is obtained therefrom 104, such as through the use of a prefilter module as previously described.

The filtered cell-free culture medium is then concentrated 106 in the permeate of an about 0.1 μm to about 1.0 μm first hollow-fiber filter tube (HFT) tangential flow filter (TFF). This permeate is the conveyed to an about 30 kD to about 600 kD or an about 60 kD to about 150 kD second HFT TFF, where a source of diafiltration buffer enables, for example, a 5 DV to 10 DV diafiltration process 108. Subsequently, the retentate of the second TFF is concentrated to a desired degree and the concentrated retentate is then collected 110 as the final exosome product.

Additional Methods of Preparing Exosome Composition and MSC Compositions

In further aspects of the disclosure, a method of making a composition is provided. As noted, the compositions herein comprise at least one mesenchymal stem cell, at least one exosome isolated from a mesenchymal stem cell, and at least one component isolated from an extracellular matrix. As noted above, the components included in the composition are present at levels much higher than normal (e.g., 5×-100× a concentration found in a comparative exosome preparation, such as one prepared by ultra-centrifugation). Further, none of the cells used in the composition are genetically edited or cultured in any stressful conditions.

In general, methods of preparing the compositions provided herein comprise isolating each component (e.g., mesenchymal stem cell, proteins, lipids, nucleic acids, exosome, and ECM component) separately, using tangential flow filtration, and then recombining to form the final composition.

Accordingly, in one aspect of the present disclosure, a method of preparing an exosome composition and an MSC composition is provided. The method comprises (a) culturing mesenchymal stem cells isolated from a tissue sample in an exosome collection media, (b) collecting the exosome collection media as a first fraction and the mesenchymal stem cells as a second fraction, the second fraction further comprising exosomes and extracellular matrix colonies and fragments thereof, (c) filtering the second fraction through a first section of a tangential flow filtration system to obtain a retentate comprising mesenchymal stem cells and a first filtrate comprising exosomes and the extracellular matrix colonies and fragments thereof, (d) collecting the retentate comprising mesenchymal stem cells as a MSC composition, filtering the first filtrate through a second section of the tangential flow filtration system to form a second retentate comprising the intact and/or partially intact extracellular matrix and a second filtrate comprising exosomes and at least one component from the extracellular matrix, (e) combining the second filtrate with the first fraction to form a third fraction, and (f) collecting the third fraction as the exosome composition.

In various aspects, the method may further comprise filtering the third fraction through a third section of the tangential flow filtration system to form a third filtrate and collecting the third filtrate as the exosome composition. In some aspects, the third filtrate comprises at least one component from the extracellular matrix colonies (e.g., an ECM component), wherein the ECM component is present at a higher concentration in the third filtrate than in the second filtrate.

In still further aspects, the method may further comprise filtering the third filtrate through a fourth section of the tangential flow filtration system to form a fourth filtrate and collecting the fourth filtrate as the exosome composition. In some aspects, the fourth filtrate comprises at least one ECM component present at a higher concentration as compared to the concentration of the component in the third filtrate.

Optionally, the method may further comprise additional steps, where a filtrate obtained in the previous step is filtered through an additional section of the tangential flow filtration system.

In various aspects, the methods may comprise filtering a filtrate through a first section, a second section, a third section, and/or a fourth section of a tangential flow filtration system. In various aspects, the first section comprises a filter having a pore size of about 50 kD to about 100 microns. For example, in some aspects the first section may comprise a filter or cassette comprising a pore size of about 0.1 to 10 microns. In some aspects, the first section may comprise a filter or cassette comprising a pore size of about 0.5 to 1 microns (e.g., about 0.5, 0.6, 0.7, 0.8, 0.9, or 1.0 microns). In some aspects, the second section comprises a filter having a pore size of about 50 kD to about 100 microns. In some aspects, the second section comprises a filter or cassette comprising a pore size of about 50 kD to about 500 kD (e.g., about 100 kD). In further aspects, the third section may comprise a filter having a pore size of about 50 kD to about 100 microns. In some aspects, the third section comprises a filter or cassette comprising a pore size of about 200 to 800 kD (e.g., about 500 kD). In still further aspects, the fourth section may comprise a filter having a pore size of about 50 kD to about 100 microns. Suitable pore sizes that may be used in any of the sections are described further below.

In various aspects, the first section, second section, third section, and/or fourth section, and additional sections/filtration steps as needed, of the tangential flow filtration system may independently comprise a hollow fiber filter or cassette. The hollow fiber filter or cassette may comprise a pore size correlating to the size of the retentate isolated at each section. In some aspects, the pore size is from about 50 kD to about 100 microns. In some aspects, the pore size is about 50 kD to about 1 micron, about 60 kD to about 1 micron, about 40 kD to about 150 kD, about 60 kD to about 150 kD. In some aspects, the hollow fiber filters may have a pore size of about 50 kD, about 60 kD, about 70 kD, about 80 kD, about 90 kD, about 100 kD, about 110 kD, about 120 kD, about 130 kD, about 140 kD, about 150 kD, about 200 kD, about 250 kD, about 300 kD, about 350 kD, about 400 kD, about 450 kD, about 500 kD, or about 600 kD In further aspects and so on, the pore size may be about 700 kD to about 1 micron. In some aspects, the pore size may be about 700 kD, about 750 kD, about 800 kD, about 850 kD, about 900 kD, about 950 kD or about 1 micron. In further aspects, the pore size may be about 1 micron to about 100 microns. For example, the pore size may be about 1 to 2 microns (e.g., about 1.0 micron about 1.1 micron, about 1.2 micron, about 1.3 micron, about 1.4 micron, about 1.5 micron, about 1.6 micron, about 1.7 micron, about 1.8 micron, about 1.9 micron, or about 2.0 micron), about 2-3 micron (e.g., about 2.0 micron, about 2.1 micron, about 2.3 micron, about 2.4 micron, about 2.5 micron, about 2.6 micron, about 2.7 micron, about 2.8 micron, about 2.9 micron, or about 3.0 micron), or about 3-4 micron (e.g., about 3.0 micron, about 3.1 micron, about 3.2 micron, about 3.3 micron, about 3.4 micron, about 3.5 micron, about 3.5 micron, about 3.6 micron, about 3.7 micron, about 3.8 micron, about 3.9 micron or about 4.0 micron) As another example, the pore size may be about 4-5 microns (e.g., about 4.0 micron, about 4.1 micron, about 4.2 micron, about 4.3 micron, about 4.4 micron, about 4.5 micron, about 4.6 micron, about 4.7 micron, about 4.8 micron, about 4.9 micron or about 5.0 micron). In another example, the pore size may be about 5-6 microns (e.g., about 5.0 micron, about 5.1 micron, about 5.2 micron, about 5.3 micron, about 5.4 micron, about 5.5, micron, about 5.6 micron, about 5.7 micron, about 5.8 micron, about 5.9 micron or about 6.0 micron). In still another example, the pore size may be about 6-7 microns (e.g., about 6.0 microns, about 6.1 microns, about 6.2 microns, about 6.3 microns, about 6.4 microns, about 6.5 microns, about 6.6, microns, about 6.7 microns, about 6.8 microns, about 6.9 microns, or about 7.0 microns). As another example, the pore size may be about 7 to 8 microns (e.g., about 7.1 microns, about 7.2 microns, about 7.3 microns, about 7.4 microns, about 7.5 microns, about 7.6 microns, about 7.7 microns, about 7.8 microns, about 7.9 microns or about 8.0 microns and so on). Various other pore sizes (e.g., smaller than 50 kD or larger than 100 microns) may be also contemplated.

Each section of the tangential flow filtration system (e.g., the first section, the second section, the third section and the fourth section or additional sections/filtration steps) may comprise a hollow fiber filter having a pore size specific for that section.

In various aspects, the tissue sample may comprise or may be obtained from umbilical cord blood, placental tissue, umbilical cord tissue, adipose tissue, bone marrow, skin, occular tissue, or teeth. For example, in some aspects, the tissue sample may comprise human placental and/or umbilical cord tissue.

It should also be understood that, unless clearly indicated to the contrary, in any methods claimed herein that include more than one step or act, the order of the steps or acts of the method is not necessarily limited to the order in which the steps or acts of the method are recited.

III. Kits

Various aspects of the present disclosure are directed to kits comprising one or more of the pharmaceutical compositions provided herein. In some aspects, a kit is provided comprising an exosome composition comprising an exosome and at least one component isolated from an extracellular matrix. In some aspects, a kit is provided comprising an MSC composition comprising one or more mesenchymal stem cells. In other aspects, a kit is provided comprising (a) an exosome composition comprising an exosome and at least one component isolated from an extracellular matrix and (b) an MSC composition comprising mesenchymal stem cells.

In any of the kits described herein, the exosome composition may comprise one or more exosomes and one or more components isolated from an extracellular matrix, as described herein. The exosome composition may further comprise a carrier or excipient. In some aspects, the exosome composition may comprise a saline based carrier or excipient. In some aspects, the kit may comprise one or more unit dosages of the exosome composition as provided herein.

In any of the kits described herein, the MSC composition may comprise one or more mesenchymal stem cells. In various aspects, the MSC composition may further comprise a carrier or excipient, as described above. In further aspects, the MSC composition may comprise a saline-based carrier or excipient. In some aspects, the kit may comprise one or more unit dosages of the MSC composition as provided herein.

In various embodiments, the MSC composition may comprise mesenchymal stem cells that are isolated from the same tissue sample used to prepare the exosome composition . . . .

In various aspects, the exosome composition and the MSC composition are provided in a manner to allow for them to be combined prior to administration to a subject.

The kits of this invention are in suitable packaging. Suitable packaging includes preservation and packaging as liquids or powders, but is not limited to, vials, bottles, jars, sheets, flexible packaging (e.g., sealed Mylar or plastic bags), and the like. A kit may have a sterile access port (e.g., the container may be a vial having a stopper pierceable by a hypodermic injection needle).

Kits may optionally provide additional components such as buffers and interpretive information. Normally, the kit comprises a container and a label or package insert(s) on or associated with the container. In some embodiments, the invention provides articles of manufacture comprising contents of the kits described above.

IV. Methods of Use

Further aspects of the present disclosure are directed to methods of treating a subject in need thereof with the compositions provided herein. In various aspects, the methods may comprise administering a first composition comprising at least one exosome and at least one component isolated from an extracellular matrix and a second composition comprising mesenchymal stem cells to a subject. In various aspects, the first composition and the second composition may be prepared and isolated from a single tissue source according to the methods provided above.

In various aspects, the subject may be an individual having or at risk of having any of the following conditions: respiratory and pulmonary diseases or disorders; such as but not limited to cystic fibrosis, pulmonary fibrosis, Chronic Obstructive Pulmonary Disease (COPD), COVID-19 and post COVID-19 symptoms, Arthritis, Avulsions, Plantar Fasciitis, traumatic brain injury or neurological conditions, ophthalmological conditions, Female or Male Reproductive Conditions such as; Polycystic Ovary Syndrome (PCOS) or Primary Ovarian Insfficiency (POI) or Azoospermia or Erectile Dysfunction, Alopecia, Muscular Dystrophy, Autism, cancer, gastrointestinal disorders and diseases, wounds, kidney disease, heart disorders and diseases.

In any of the methods of treatment described herein, the exosome composition and/or the MSC composition may be formulated as pharmaceutical compositions suitable for administration via a route optimal for delivery to a region of the subject affected by the disease or disorder. For example, in various aspects, the pharmaceutical compositions may be administered via injection (e.g., via joint or intramuscular injection) or soft tissue injections. In other aspects, the pharmaceutical compositions may be administered orally or parenterally (e.g., intravenously, subcutaneously, or via infusion). In some aspects, the pharmaceutical compositions may be administered via inhalation.

V. Terminology

The phraseology and terminology employed herein are for the purpose of description and should not be regarded as limiting. For example, the use of a singular term, such as, "a" is not intended as limiting of the number of items. Also, the use of relational terms such as, but not limited to, "top," "bottom," "left," "right," "upper," "lower," "down," "up," and "side," are used in the description for clarity in specific reference to the figures and are not intended to limit the scope of the present inventive concept or the appended claims.

Further, as the present inventive concept is susceptible to embodiments of many different forms, it is intended that the present disclosure be considered as an example of the principles of the present inventive concept and not intended to limit the present inventive concept to the specific embodiments shown and described. Any one of the features of the present inventive concept may be used separately or in combination with any other feature. References to the terms "embodiment," "embodiments," and/or the like in the description mean that the feature and/or features being referred to are included in, at least, one aspect of the description. Separate references to the terms "embodiment," "embodiments," and/or the like in the description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments but is not necessarily included. Thus, the present inventive concept may include a variety of combinations and/or integrations of the embodiments described herein. Additionally, all aspects of the present disclosure, as described herein, are not essential for its practice. Likewise, other systems, methods, features, and advantages of the present inventive concept will be, or become, apparent to one with skill in the art upon examination of the figures and the description. It is intended that all such additional systems, methods, features, and advantages be included within this description, be within the scope of the present inventive concept, and be encompassed by the claims.

As used herein, the term "about," can mean relative to the recited value, e.g., amount, dose, temperature, time, percentage, etc., ±10%, ±9%, ±8%, ±7%, ±6%, ±5%, ±4%, ±3%, ±2%, or 1%.

The terms "comprising," "including," "encompassing" and "having" are used interchangeably in this disclosure. The terms "comprising," "including," "encompassing" and "having" mean to include, but not necessarily be limited to the things so described.

The terms "or" and "and/or," as used herein, are to be interpreted as inclusive or meaning any one or any combination. Therefore, "A, B or C" or "A, B and/or C" mean any of the following: "A," "B" or "C"; "A and B"; "A and C"; "B and C"; "A, B and C." An exception to this definition will occur only when a combination of elements, functions, steps or acts are in some way inherently mutually exclusive.

The term "treat," "treated," "treating," or "treatment" includes the diminishment or alleviation of at least one symptom associated or caused by the state, disorder or disease being treated. In certain embodiments, the treatment comprises binging into contact with an infection an effective amount of an anti-infective formulation of the disclosure for conditions related to infections.

As used herein, the term "patient," "individual" or "subject" refers to a human or a non-human mammal. Non-human mammals include—but are not limited to, livestock and pets, such as ovine, bovine, porcine, canine, feline, lupine, murine, and marine mammals.

As used herein, the terms "effective amount," "pharmaceutically effective amount," and "therapeutically effective amount" refer to a nontoxic but sufficient amount of the purine, purine precursor, purine analog, pyrimidine, pyrimidine precursor, and/or pyrimidine analog to provide the desired biological result. That result may be reduction or alleviation of the signs, symptoms, or causes of a disease, e.g., cancer, or any other desired alteration of a biological system. An appropriate therapeutic amount in any individual case may be determined by one of ordinary skill in the art using routine experimentation.

The terms "culture", "culture medium", "cell culture", and "MSC culture" as used herein refer to a mesenchymal stem cell population that is suspended in a medium under conditions suitable to survival and/or growth of the cell population. These terms as used herein refer to the combination comprising the MSC population and the medium in which the population is suspended.

The terms "medium", "media", "culture medium", and "growth medium" as used herein refer to a substance containing components to support living cells, e.g., nutrients which nourish growing MSCs (i.e., a growth medium), and/or which supports the collection of cells from their expansion or maintenance container (e.g., a collection medium). Typically, these media provide essential and nonessential amino acids, vitamins, energy sources, lipids, and trace elements required by the cell for minimal growth and/or survival. A growth medium can also contain components that enhance growth and/or survival above the minimal rate, including hormones and growth factors. Media are formulated to a pH and salt concentration optimal for cell survival and proliferation. The medium may take any form, such as a solid (as in a petri dish), or liquid.

As used herein, the term "filtrate" refers to the solution and its contents that have passed through a filter.

As used herein, the term "permeate" refers to the solution and its contents that have passed through a membrane filter.

As used herein, the term "retentate" encompasses the components of a solution that have not passed through, and thus are retained by, a membrane filter.

The term "hollow fiber filter (or HFF) as used herein refers to tubes, cassettes, packs, and any container known in the art to contain and comprise hollow fiber filters.

The term "diafiltration" as used herein encompasses a dilution process that involves removal or separation of permeable components ("permeates") from a solution based on their molecular size with micro-molecule permeable filters in order to obtain a more pure solution. For example, to effectively remove permeate components from solution, fresh solvent may be added to the feed to replace the permeate volume, at the same rate as the permeate flow rate, such that the volume in the system remains constant.

"Tangential flow filtration" (TFF) is a type of filtration in which the majority of the feed flow travels tangentially across the surface of a filter, rather than into the filter. This type of filtration is useful for feeds containing a high proportion of small particle size solids (where the permeate is the product) because solid material can quickly block (blind) the filter surface with dead-end filtration. The term "TFF" also encompasses the filtration device which can be a tube, cassette or any container that comprises one or more hollow fiber filter(s).

The term "prefilter" as used herein is a preliminary filtering element, module, device, or process step or steps used upstream of a membrane filter in order to remove relatively large particulates and to reduce the pressure drop when filtering through one or more downstream membrane filters. The size of the housing needed for downstream membrane filters may thus be reduced.

As used herein, the term "free of" means lacking any or without any.

It should also be understood that, unless clearly indicated to the contrary, in any methods claimed herein that include more than one step or act, the order of the steps or acts of the method is not necessarily limited to the order in which the steps or acts of the method are recited.

Having described several embodiments, it will be recognized by those skilled in the art that various modifications, alternative constructions, and equivalents may be used without departing from the spirit of the present inventive concept. Additionally, a number of well-known processes and elements have not been described in order to avoid unnecessarily obscuring the present inventive concept. Accordingly, this description should not be taken as limiting the scope of the present inventive concept.

Those skilled in the art will appreciate that the presently disclosed embodiments teach by way of example and not by limitation. Therefore, the matter contained in this description or shown in the accompanying drawings should be interpreted as illustrative and not in a limiting sense. The following claims are intended to cover all generic and specific features described herein, as well as all statements of the scope of the method and assemblies, which, as a matter of language, might be said to fall there between.

EXAMPLES

The following examples are included to demonstrate preferred embodiments of the disclosure. It should be appreciated by those of skill in the art that the techniques disclosed in the examples that follow represent techniques discovered by the inventor to function well in the practice of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

Example 1

An umbilical cord was obtained, dissected into tissue samples, washed and stored in PBS in a petri dish. In one experiment, the umbilical cord tissue pieces were placed in a conical tube and colleganase IV was added. The mixture was incubated at 37° C. for 25-36 minutes, which freed the mesenchymal stem cells, allowing for them to be plated in a single cell stack.

In another experiment, the umbilical cord tissue pieces were pulverized using a 40-micron filter which allowed for MSC release into PBS before being placed on a single cell stack.

After MSCs were isolated in a single cell stack, a standard MSC cell expansion media and MSC expansion techniques were used to expand the cells from a single layer cell stack to 10-layer cell stack to 15 liter bio reactor. Then traditional 15-liter bio reactor techniques with media exchange were used until 85% confluency of microcarriers was reached, at which point the media was switched to an exosome collection media for 3 days. After 3 days the exosome collection media was drained and stored, and a lysing technique was used to collect MSCs and their extracellular matrix colonies and materials. Throughout this time, healthy cells were monitored.

The collected mixture (containing MSCs and extracellular matrix colonies and materials) was set aside as one mixture and the exosome collection media (containing exosomes) was set aside as a second mixture. The first mixture (containing MSCs and extracellular matrix colonies and materials) was then applied through a filtration process using a down-stream filter chain and then into a first section of a tangential flow filtration system outfitted with a 0.63-micron hollow fiber filter tube and two peristaltic pumps (one at the feed and one at the permeate). Mesenchymal stem cells were collected in the retentate, and the extracellular matrixes components and exosomes were collected in the permeate. The collected mesenchymal stem cells were stored using cryopreservation medias and freezing techniques for 90-97% viability.

The permeate collected in the first step was then run through a second tangential flow filtration using a 100 kD hollow fiber filter tube which broke up the ECM materials into smaller components and help remove debris. The permeate from this filtration was then combined with the collected exosome media (second mixture) and run through a third tangential flow filtration system using a 500 kD hollow fiber filter tube. The permeate from this last filtration was then run through 500 kD Run 7 diafiltrations exchanging the media for phosphate buffer saline (PBS) before concentrating the material for preparation of pharmaceutical compositions.

Example 2

The exosome composition in Example 1 was analyzed and compared to a commercially available exosome preparation (e.g., AMNIOSOME). Both compositions were analyzed by conventional proteomic techniques. It was found that levels of over 1900 compounds/growth factors/or other components found in extracellular matrix were elevated in the composition of Example 1 compared to levels in the commercially available preparation. (Table 1). Specifically, the following components were found to be elevated at least 30-fold in the pharmaceutical composition relative to the amniosome preparation: Cysteine-rich Protein 1, PIM2, Cadherin-13, Beta IG-H3, EG-VEGF/PK1, Cyclophilin A, Dkk-3, BMP-3, QDPR, PAM, EDAR, EGF R/ErbB1, ALCAM, CXCR3, SBP-1, BCMA/TNFRSF17, CCL28/VIC, IL-29, HSP47, VE-Cadherin, I-309, TGF-beta RIII, CCR8, Fractalkine, TCN1, RSU1, uPAR, VEGF-D, PRELP, TGF-beta RII, Thrombopoietin (TPO), Endothelin, S100A6, Angiogenin, TIMP-4, MSP alpha Chain, Activin A, DMGDH, Serpin B8, TRAIL R3/TNFRSF10C, CFHR5, Caspase-14, PRDX 1, FGF-12, CXCR5/BLR-1, Semaphorin 7A, SPINK7, NT-4, TNF RII/TNFRSF1B, 6Ckine, SerRS, Angiostatin, Angiopoietin-like Factor, B7-1/CD80, Protein C, Tcf20, TROY/TNFRSF19, EMAP-II, CSH1, TLR4, RPLPO, and ErbB3. The following components were found to be elevated at least 40-fold relative to the amniosome preparation: Cysteine-rich Protein 1, PIM2, Cadherin-13, Beta IG-H3, EG-VEGF/PK1, Cyclophilin A, Dkk-3, BMP-3, QDPR, PAM, EDAR, EGF R/ErbB1, ALCAM, CXCR3, and SBP-1. The following components were found to be elevated at least 50-fold relative to the amnosome preparation: Cysteine-rich Protein 1, PIM2, Cadherin-13, Beta IG-H3, EG-VEGF/PK1, and Cyclophilin A.

TABLE 1

| | Composition (Ex. 1) | Comparative Product X | Fold Change |
|---|---|---|---|
| Cysteine-rich Protein 1 | 149,203 | 1,104 | 135 |
| PIM2 | 115,964 | 1,187 | 98 |
| Cadherin-13 | 73,139 | 1,091 | 67 |
| Beta IG-H3 | 80,636 | 1,254 | 64 |
| EG-VEGF/PK1 | 68,881 | 1,210 | 57 |
| Cyclophilin A | 45,737 | 846 | 54 |
| Dkk-3 | 38,287 | 784 | 49 |
| BMP-3 | 88,015 | 1,843 | 48 |
| QDPR | 37,451 | 811 | 46 |
| PAM | 33,225 | 731 | 45 |
| EDAR | 42,662 | 958 | 45 |
| EGF R/ErbB1 | 41,416 | 933 | 44 |
| ALCAM | 61,608 | 1,467 | 42 |
| CXCR3 | 66,674 | 1,645 | 41 |
| SBP-1 | 32,293 | 806 | 40 |
| BCMA/TNFRSF17 | 37,102 | 976 | 38 |
| CCL28/VIC | 78,792 | 2,078 | 38 |
| IL-29 | 42,551 | 1,127 | 38 |
| HSP47 | 20,436 | 546 | 37 |
| VE-Cadherin | 26,081 | 708 | 37 |
| I-309 | 34,480 | 938 | 37 |
| TGF-beta RIII | 24,023 | 661 | 36 |
| CCR8 | 52,976 | 1,464 | 36 |
| Fractalkine | 29,902 | 843 | 35 |
| TCN1 | 37,005 | 1,052 | 35 |
| RSU1 | 32,106 | 921 | 35 |
| uPAR | 22,952 | 663 | 35 |
| VEGF-D | 23,224 | 687 | 34 |
| PRELP | 36,022 | 1,074 | 34 |
| TGF-beta RII | 21,509 | 642 | 33 |
| Thrombopoietin (TPO) | 21,818 | 652 | 33 |
| Endothelin | 27,732 | 830 | 33 |
| S100A6 | 40,864 | 1,224 | 33 |
| Angiogenin | 47,702 | 1,435 | 33 |
| TIMP-4 | 20,307 | 611 | 33 |
| MSP alpha Chain | 38,530 | 1,163 | 33 |
| Activin A | 54,561 | 1,665 | 33 |
| DMGDH | 134,640 | 4,139 | 33 |
| Serpin B8 | 27,810 | 865 | 32 |
| TRAIL R3/TNFRSF10C | 20,997 | 657 | 32 |
| CFHR5 | 34,102 | 1,068 | 32 |
| Caspase-14 | 39,469 | 1,251 | 32 |
| PRDX 1 | 42,240 | 1,349 | 31 |
| FGF-12 | 34,839 | 1,120 | 31 |
| CXCR5/BLR-1 | 58,132 | 1,878 | 31 |
| Semaphorin 7A | 24,942 | 807 | 31 |
| SPINK7 | 21,269 | 691 | 31 |
| NT-4 | 31,028 | 1,011 | 31 |
| TNF RII/TNFRSF1B | 19,548 | 638 | 31 |
| 6Ckine | 52,082 | 1,700 | 31 |
| SerRS | 34,859 | 1,145 | 30 |
| Angiostatin | 48,636 | 1,602 | 30 |
| Angiopoietin-like Factor | 18,397 | 608 | 30 |
| B7-1/CD80 | 32,128 | 1,068 | 30 |
| Protein C | 35,349 | 1,184 | 30 |
| Tcf20 | 29,604 | 992 | 30 |
| TROY/TNFRSF19 | 17,905 | 600 | 30 |
| EMAP-II | 39,423 | 1,324 | 30 |
| CSH1 | 30,240 | 1,018 | 30 |
| TLR4 | 18,946 | 639 | 30 |
| RPLP0 | 29,025 | 983 | 30 |
| ErbB3 | 39,907 | 1,352 | 30 |
| RPL11 | 23,521 | 800 | 29 |
| PGK-1 | 30,469 | 1,036 | 29 |
| FGF-16 | 51,205 | 1,742 | 29 |
| Plakophilin 1 | 27,751 | 949 | 29 |
| PRCP | 35,799 | 1,224 | 29 |
| RAGE | 26,777 | 919 | 29 |
| Insulin | 18,388 | 632 | 29 |
| TSR2 | 21,530 | 740 | 29 |
| NT-3 | 31,941 | 1,106 | 29 |
| USP14 | 19,830 | 689 | 29 |
| VDAC1/Porin | 22,828 | 797 | 29 |
| Proteasome 20S a + b | 34,141 | 1,198 | 28 |
| M-CSF | 33,014 | 1,162 | 28 |
| IL-2 | 39,782 | 1,401 | 28 |
| ICAM-1 | 33,591 | 1,185 | 28 |
| NEDD8 | 40,984 | 1,450 | 28 |
| PRG2 | 25,365 | 904 | 28 |
| Insulysin/IDE | 25,461 | 908 | 28 |
| ICAM-2 | 24,504 | 883 | 28 |
| MMP-1 | 24,507 | 884 | 28 |
| Salivary alpha amylase/aAmylase | 25,763 | 933 | 28 |
| IL-17F | 29,785 | 1,085 | 27 |
| Galectin-1 | 24,936 | 912 | 27 |
| Lymphotoxin beta/TNFSF3 | 40,746 | 1,492 | 27 |
| TBCA | 29,394 | 1,079 | 27 |
| PREP | 30,057 | 1,108 | 27 |
| VAP-A | 20,295 | 750 | 27 |
| Utrophin | 18,967 | 701 | 27 |
| YB1 | 18,400 | 684 | 27 |
| VAP-1 | 22,983 | 858 | 27 |
| CFHR4 | 46,661 | 1,745 | 27 |
| FGF-20 | 22,187 | 831 | 27 |
| Cyclophilin B | 48,270 | 1,811 | 27 |
| RNASE4 | 29,155 | 1,095 | 27 |
| SBSN | 29,412 | 1,105 | 27 |
| FGF R4 | 44,618 | 1,677 | 27 |
| FGF-17 | 30,774 | 1,167 | 26 |
| PGLS-C-t | 31,449 | 1,201 | 26 |
| Eotaxin-3/CCL26 | 37,851 | 1,450 | 26 |
| RREB1 | 19,521 | 749 | 26 |
| TMEM223 | 19,299 | 742 | 26 |
| ADAMTS-15 | 17,976 | 696 | 26 |
| Semenogelin II/SEMG2 | 29,002 | 1,127 | 26 |
| C3a | 40,536 | 1,589 | 26 |
| RPL12 | 21,195 | 831 | 25 |
| GDF8 | 29,382 | 1,155 | 25 |
| IGF-II | 25,799 | 1,017 | 25 |
| RPS25 | 20,252 | 799 | 25 |
| Follistatin-like 1 | 28,349 | 1,121 | 25 |
| Smad 5 | 16,806 | 665 | 25 |
| Notch-2 | 33,545 | 1,327 | 25 |

TABLE 1-continued

| | Composition (Ex. 1) | Comparative Product X | Fold Change |
|---|---|---|---|
| I-TAC/CXCL11 | 32,382 | 1,282 | 25 |
| TRANCE | 22,237 | 882 | 25 |
| MMP-3 | 23,176 | 920 | 25 |
| uPA | 18,676 | 742 | 25 |
| WDR1 | 20,309 | 807 | 25 |
| UQCRB | 18,808 | 755 | 25 |
| DR6/TNFRSF21 | 25,103 | 1,014 | 25 |
| BMP-15 | 30,067 | 1,214 | 25 |
| PSMA4 | 32,129 | 1,298 | 25 |
| ErbB4 | 42,960 | 1,737 | 25 |
| Gephyrin | 39,752 | 1,615 | 25 |
| beta-NGF | 48,014 | 1,952 | 25 |
| BMP-2 | 42,980 | 1,749 | 25 |
| BMP-6 | 28,712 | 1,169 | 25 |
| NAP-2 | 23,985 | 978 | 25 |
| LECT2 | 23,752 | 974 | 24 |
| FGF-13 1B | 27,960 | 1,153 | 24 |
| Reg3A | 25,684 | 1,061 | 24 |
| CD14 | 37,782 | 1,561 | 24 |
| SHIP | 24,658 | 1,020 | 24 |
| RPL5 | 20,382 | 844 | 24 |
| VEGF | 16,527 | 687 | 24 |
| IL-1 F5/FIL1delta | 32,327 | 1,344 | 24 |
| RPS28 | 23,823 | 991 | 24 |
| TUBA6 | 20,864 | 868 | 24 |
| Endostatin | 33,106 | 1,378 | 24 |
| MMP-9 | 34,631 | 1,443 | 24 |
| CK-MB | 30,019 | 1,255 | 24 |
| CapG | 47,296 | 1,982 | 24 |
| IL-11 | 30,940 | 1,298 | 24 |
| Ribonuclease A | 30,250 | 1,272 | 24 |
| Eotaxin-2/MPIF-2 | 28,293 | 1,191 | 24 |
| GLO-1 | 17,986 | 758 | 24 |
| TLR3 | 14,894 | 628 | 24 |
| HGF | 32,924 | 1,390 | 24 |
| Sterol carrier protein 2/SCP2 | 24,330 | 1,027 | 24 |
| Visfatin | 21,155 | 900 | 24 |
| SHC1 | 29,841 | 1,279 | 23 |
| IL-18 R beta/AcPL | 35,493 | 1,522 | 23 |
| SIGLEC14 | 17,357 | 745 | 23 |
| PRTN3 | 29,438 | 1,263 | 23 |
| Contactin-1 | 22,064 | 947 | 23 |
| CV-2/Crossveinless-2 | 27,932 | 1,200 | 23 |
| EDG-1 | 60,140 | 2,592 | 23 |
| CXCL14/BRAK | 44,202 | 1,905 | 23 |
| TIMP-3 | 18,709 | 807 | 23 |
| Serpin A1 | 26,893 | 1,162 | 23 |
| Annexin A1 | 36,102 | 1,561 | 23 |
| TGM3 | 21,623 | 936 | 23 |
| CXCR6 | 40,642 | 1,759 | 23 |
| PGM1 | 30,176 | 1,307 | 23 |
| Osteoprotegerin/TNFRSF11B | 31,132 | 1,354 | 23 |
| Coagulation Factor III/Tissue Factor | 24,385 | 1,061 | 23 |
| M-CSF R | 27,715 | 1,208 | 23 |
| MDC | 19,302 | 849 | 23 |
| FAM3B | 27,761 | 1,221 | 23 |
| MMP-11/Stromelysin-3 | 28,775 | 1,267 | 23 |
| SCF R/CD117 | 30,514 | 1,344 | 23 |
| TGF-beta 5 | 33,193 | 1,467 | 23 |
| Titin | 19,113 | 845 | 23 |
| sFRP-3 | 14,536 | 643 | 23 |
| IL-1 beta | 31,067 | 1,382 | 22 |
| HCC-4/CCL16 | 31,885 | 1,420 | 22 |
| TRAIL/TNFSF10 | 15,890 | 708 | 22 |
| Fascin | 29,829 | 1,330 | 22 |
| BNP | 56,464 | 2,518 | 22 |
| ADAMTS-13 | 16,762 | 751 | 22 |
| PLOD1 | 22,859 | 1,024 | 22 |
| FLRG | 23,149 | 1,039 | 22 |
| LDHA | 33,197 | 1,492 | 22 |
| LIF | 22,784 | 1,024 | 22 |
| YY1 | 23,334 | 1,051 | 22 |
| NME3 | 29,412 | 1,326 | 22 |
| ESAM | 23,809 | 1,075 | 22 |
| RPS19 | 22,292 | 1,007 | 22 |
| EpCAM | 26,880 | 1,215 | 22 |
| TAGLN2 | 20,278 | 917 | 22 |
| CXCL16 | 25,046 | 1,133 | 22 |
| BTF3 | 29,870 | 1,352 | 22 |
| Hemoglobin subunit beta/HBB | 32,091 | 1,453 | 22 |
| TRADD | 22,568 | 1,022 | 22 |
| Metavinculin | 24,036 | 1,090 | 22 |
| BDNF | 38,489 | 1,752 | 22 |
| Galectin-7 | 23,599 | 1,075 | 22 |
| PPP2R4 | 29,134 | 1,328 | 22 |
| FACX | 26,222 | 1,198 | 22 |
| PDZD2 | 25,371 | 1,160 | 22 |
| IL-26 | 30,655 | 1,402 | 22 |
| FGF-9 | 29,601 | 1,354 | 22 |
| Fibrinogen-like 2 | 26,901 | 1,231 | 22 |
| Plexin B2 | 33,435 | 1,533 | 22 |
| Thrombomodulin | 26,841 | 1,234 | 22 |
| Dtk | 31,635 | 1,455 | 22 |
| TRAIL R2/DR5/TNFRSF10B | 21,922 | 1,009 | 22 |
| PNP | 34,355 | 1,581 | 22 |
| ANGPTL8 | 32,467 | 1,497 | 22 |
| B7-H3 | 46,713 | 2,154 | 22 |
| ACLP | 50,429 | 2,328 | 22 |
| Galectin-3 | 24,906 | 1,150 | 22 |
| p73 | 27,714 | 1,280 | 22 |
| IL-4 | 35,063 | 1,620 | 22 |
| IL-13 R alpha 2 | 26,900 | 1,243 | 22 |
| TOB2 | 27,179 | 1,257 | 22 |
| Claudin-3 | 27,121 | 1,256 | 22 |
| IL-8 | 29,634 | 1,374 | 22 |
| VEGF-C | 18,712 | 868 | 22 |
| IGF-I SR | 30,199 | 1,406 | 21 |
| Tenascin X(1) | 24,673 | 1,150 | 21 |
| Lefty - A | 24,434 | 1,141 | 21 |
| Thrombospondin-1 | 37,063 | 1,732 | 21 |
| OSM R beta | 29,453 | 1,376 | 21 |
| SUCLG1 | 21,081 | 986 | 21 |
| PDGF-AB | 25,932 | 1,214 | 21 |
| IL-6 R | 29,897 | 1,406 | 21 |
| IL-18 BPa | 31,825 | 1,497 | 21 |
| PGAM2 | 27,086 | 1,276 | 21 |
| Cripto-1 | 28,401 | 1,338 | 21 |
| FGF-23 | 27,823 | 1,311 | 21 |
| GSTM1 | 32,803 | 1,549 | 21 |
| ICAM-5 | 29,071 | 1,374 | 21 |
| RPL10 | 17,000 | 804 | 21 |
| Ribonuclease Inhibitor | 30,183 | 1,430 | 21 |
| ARTS1 | 50,156 | 2,381 | 21 |
| Periostin | 26,741 | 1,274 | 21 |
| UCH-L1 | 19,573 | 933 | 21 |
| Zyxin | 8,465 | 404 | 21 |
| RPL10A | 20,817 | 995 | 21 |
| PDLIM5 | 22,539 | 1,078 | 21 |
| IL-15 R alpha | 27,140 | 1,302 | 21 |
| FAM3C | 34,874 | 1,679 | 21 |
| Tropomyosin 3 | 21,960 | 1,058 | 21 |
| LZTS1 | 21,074 | 1,016 | 21 |
| LIGHT/TNFSF14 | 29,147 | 1,406 | 21 |
| Osteoadherin(2) | 25,234 | 1,219 | 21 |
| SHMT1 | 20,473 | 990 | 21 |
| CCR9 | 37,245 | 1,809 | 21 |
| TWEAK R/TNFRSF12 | 14,437 | 702 | 21 |
| TPP1 | 22,445 | 1,098 | 20 |
| ADAMTS-10 | 17,984 | 881 | 20 |
| RCL | 18,903 | 926 | 20 |
| PCDH7 | 20,445 | 1,004 | 20 |
| MIG | 21,444 | 1,053 | 20 |
| SPARC | 24,373 | 1,197 | 20 |
| SH3BGRL | 25,017 | 1,230 | 20 |
| Thrombospondin-4 | 21,067 | 1,036 | 20 |
| UFM 1 | 22,515 | 1,107 | 20 |
| Prostaglandin D Synthase/PTGDS | 39,363 | 1,938 | 20 |
| GPR-39 | 23,460 | 1,158 | 20 |
| SPTBN1 | 27,815 | 1,375 | 20 |
| BLVRB | 26,728 | 1,322 | 20 |
| RKIP | 21,651 | 1,072 | 20 |

TABLE 1-continued

| | Composition (Ex. 1) | Comparative Product X | Fold Change |
|---|---|---|---|
| 4-1BB | 14,926 | 739 | 20 |
| Decorin | 34,993 | 1,734 | 20 |
| CRIM 1 | 34,092 | 1,692 | 20 |
| PCSK9 | 19,231 | 955 | 20 |
| STI1 | 17,991 | 893 | 20 |
| IL-22 BP | 26,510 | 1,317 | 20 |
| VEGF R2 (KDR) | 14,133 | 702 | 20 |
| Ficolin-2 | 26,276 | 1,306 | 20 |
| CXCR4 (fusin) | 33,542 | 1,667 | 20 |
| SIGIRR | 30,497 | 1,518 | 20 |
| IFN-beta | 33,101 | 1,649 | 20 |
| Cyclin D1 | 25,037 | 1,248 | 20 |
| MIP-1a | 31,294 | 1,561 | 20 |
| RPS11 | 24,126 | 1,203 | 20 |
| Alpha 1 AG | 25,755 | 1,285 | 20 |
| BLAME | 25,805 | 1,290 | 20 |
| Cystatin E/M | 41,616 | 2,083 | 20 |
| GM-CSF R alpha | 35,942 | 1,807 | 20 |
| Uteroglobin(1) | 28,383 | 1,428 | 20 |
| Trypsinogeb-2 | 20,582 | 1,039 | 20 |
| MCP-3 | 25,066 | 1,269 | 20 |
| Erythropoietin R | 17,635 | 893 | 20 |
| Proteasome subunit alpha type 6/PSMA6 | 30,603 | 1,551 | 20 |
| TGF-alpha | 13,668 | 693 | 20 |
| Flt-3 Ligand | 35,206 | 1,785 | 20 |
| Nanog | 17,758 | 901 | 20 |
| TNF-alpha | 22,873 | 1,160 | 20 |
| Spectrin beta-5 | 14,067 | 716 | 20 |
| VNN1 | 16,972 | 866 | 20 |
| BMP-1 | 43,662 | 2,229 | 20 |
| FGF-7/KGF | 35,563 | 1,816 | 20 |
| OSM | 25,688 | 1,312 | 20 |
| FGF R5 | 29,164 | 1,490 | 20 |
| Transferrin | 26,482 | 1,355 | 20 |
| C5/C5a | 38,410 | 1,973 | 19 |
| ApoA1 | 41,149 | 2,114 | 19 |
| TCP1 eta | 25,301 | 1,300 | 19 |
| Galectin-3BP | 21,938 | 1,128 | 19 |
| PTPRZ | 24,708 | 1,271 | 19 |
| TRAIL R1/DR4/TNFRSF10A | 24,139 | 1,242 | 19 |
| Six3 | 22,081 | 1,136 | 19 |
| SORD | 16,563 | 852 | 19 |
| CNTF | 39,429 | 2,031 | 19 |
| GDNF | 25,969 | 1,338 | 19 |
| BMPR-II | 38,836 | 2,001 | 19 |
| CXCR2/IL-8 RB | 35,362 | 1,826 | 19 |
| FGF-8 | 26,215 | 1,354 | 19 |
| RPS5 | 23,251 | 1,201 | 19 |
| CRF21 | 39,007 | 2,017 | 19 |
| PGDF/PHGDH | 29,041 | 1,508 | 19 |
| FABP1 | 19,541 | 1,016 | 19 |
| SLURP1 | 19,488 | 1,014 | 19 |
| CEACAM-8/CD66b | 29,257 | 1,522 | 19 |
| UNC45A | 21,825 | 1,136 | 19 |
| Adiponectin/Acrp30 | 35,677 | 1,858 | 19 |
| MMP-25/MT6-MMP | 25,009 | 1,303 | 19 |
| SMC4 | 24,657 | 1,285 | 19 |
| Ornithine Carbamoyltransferase/OTC | 24,463 | 1,276 | 19 |
| IFN-gamma R1 | 26,894 | 1,403 | 19 |
| CCR4 | 30,115 | 1,572 | 19 |
| Proteasome beta 1 | 21,271 | 1,110 | 19 |
| Talin1&2 | 16,845 | 880 | 19 |
| Prohibitin | 24,124 | 1,263 | 19 |
| MMP-24/MT5-MMP | 16,935 | 887 | 19 |
| SP-D | 18,470 | 968 | 19 |
| Nidogen-2 | 18,104 | 949 | 19 |
| PTPRS | 21,753 | 1,140 | 19 |
| SIRP beta 1/CD172b | 25,241 | 1,324 | 19 |
| APRIL | 32,749 | 1,718 | 19 |
| ACE-2 | 15,239 | 800 | 19 |
| IL-6 | 27,278 | 1,432 | 19 |
| HGFA | 22,952 | 1,205 | 19 |
| E-Selectin | 36,240 | 1,904 | 19 |
| GATA-4 | 13,311 | 700 | 19 |
| VEGF R3 | 12,540 | 659 | 19 |
| UBE2D3 | 17,721 | 932 | 19 |
| BAFF R/TNFRSF13C | 18,757 | 988 | 19 |
| Layilin | 24,229 | 1,276 | 19 |
| Cytokeratin 8 | 24,133 | 1,272 | 19 |
| Profilin 1 | 24,560 | 1,295 | 19 |
| Cathepsin B | 19,271 | 1,017 | 19 |
| Marapsin | 22,510 | 1,192 | 19 |
| Lymphotactin/XCL1 | 24,415 | 1,295 | 19 |
| Nidgen-1 | 19,502 | 1,034 | 19 |
| MEP1A | 28,519 | 1,517 | 19 |
| MIF | 26,873 | 1,431 | 19 |
| IL-1 F8/FIL1 eta | 27,935 | 1,489 | 19 |
| MMP-14 | 30,203 | 1,612 | 19 |
| HB-EGF | 18,456 | 985 | 19 |
| Latent TGF-beta bp1 | 28,019 | 1,496 | 19 |
| C8B | 20,017 | 1,069 | 19 |
| SMPD4 | 31,555 | 1,686 | 19 |
| ADAMTS-18 | 15,184 | 812 | 19 |
| FGF Basic | 28,278 | 1,513 | 19 |
| IL-12 R beta 2 | 17,252 | 924 | 19 |
| MINPP1 | 27,616 | 1,482 | 19 |
| URP2 | 22,612 | 1,215 | 19 |
| Glycoprotein V | 16,534 | 889 | 19 |
| LRG1 | 31,287 | 1,682 | 19 |
| ACPP | 16,111 | 867 | 19 |
| AlphaA Crystallin/CRYAA | 24,080 | 1,296 | 19 |
| EDA-A2 | 24,511 | 1,322 | 19 |
| SH3BGRL3 | 22,561 | 1,218 | 19 |
| Serpin F2 | 17,117 | 924 | 19 |
| CD40 Ligand/TNFSF5/CD154 | 35,727 | 1,930 | 19 |
| CPEB3 | 46,158 | 2,494 | 19 |
| A2M | 18,901 | 1,023 | 18 |
| Activin B | 26,203 | 1,419 | 18 |
| SREC-II | 18,431 | 999 | 18 |
| EGF | 31,100 | 1,690 | 18 |
| FGF-19 | 18,449 | 1,003 | 18 |
| Myoferlin | 30,277 | 1,650 | 18 |
| Endoglin/CD105 | 29,311 | 1,600 | 18 |
| RECK | 18,747 | 1,024 | 18 |
| ADAM-9 | 16,548 | 906 | 18 |
| SSEA-4 | 25,424 | 1,394 | 18 |
| DDAH1 | 33,804 | 1,855 | 18 |
| P-Cadherin | 21,295 | 1,169 | 18 |
| IL-22 R | 20,435 | 1,122 | 18 |
| Glut1 | 19,737 | 1,084 | 18 |
| Symplekin | 23,473 | 1,290 | 18 |
| S100A11 | 21,413 | 1,179 | 18 |
| SLITRK1 | 18,859 | 1,038 | 18 |
| GCP-2/CXCL6 | 24,874 | 1,370 | 18 |
| SDPR | 22,304 | 1,229 | 18 |
| IGF-II R | 19,162 | 1,056 | 18 |
| P4HB | 16,222 | 894 | 18 |
| TNF-beta | 22,047 | 1,216 | 18 |
| IL-1 R8 | 16,408 | 905 | 18 |
| IL-1 alpha | 29,639 | 1,635 | 18 |
| Angiopoietin-4 | 20,410 | 1,127 | 18 |
| TCCR/WSX-1 | 14,285 | 790 | 18 |
| GITR/TNFRF18 | 30,793 | 1,707 | 18 |
| ILK | 35,633 | 1,977 | 18 |
| TCEB2 | 25,563 | 1,418 | 18 |
| RPL22 | 17,962 | 997 | 18 |
| DEP-1 | 34,996 | 1,943 | 18 |
| FGF-18 | 26,774 | 1,487 | 18 |
| TL1A/TNFSF15 | 10,943 | 608 | 18 |
| EphA6 | 14,218 | 792 | 18 |
| IL-36RN | 18,076 | 1,007 | 18 |
| Tarc | 17,311 | 964 | 18 |
| UROC1 | 27,121 | 1,513 | 18 |
| Activin C | 31,896 | 1,781 | 18 |
| FASN | 29,363 | 1,640 | 18 |
| PYGL | 20,205 | 1,129 | 18 |
| Somatostatin | 16,925 | 947 | 18 |
| Musk | 30,581 | 1,714 | 18 |
| PLA2G1B | 17,499 | 983 | 18 |
| IL-1 R3/IL-1 R AcP | 14,778 | 831 | 18 |

TABLE 1-continued

| | Composition (Ex. 1) | Comparative Product X | Fold Change |
|---|---|---|---|
| FGF-6 | 32,671 | 1,838 | 18 |
| IL-18 R alpha/IL-1 R5 | 32,067 | 1,809 | 18 |
| Tie-2 | 11,507 | 650 | 18 |
| NIT2 | 20,309 | 1,147 | 18 |
| PF4/CXCL4 | 33,866 | 1,912 | 18 |
| TPM1 | 14,914 | 843 | 18 |
| GDF11 | 28,943 | 1,637 | 18 |
| IGFBP-6 | 19,742 | 1,119 | 18 |
| Thymopoietin | 21,289 | 1,207 | 18 |
| FUCA1 | 17,656 | 1,002 | 18 |
| CRHBP | 40,876 | 2,322 | 18 |
| C1qR1 | 37,195 | 2,115 | 18 |
| STAT3 | 16,077 | 914 | 18 |
| TPM4 | 39,149 | 2,227 | 18 |
| Follistatin | 36,797 | 2,093 | 18 |
| Laminin b2 | 27,191 | 1,548 | 18 |
| IL-1 sRI | 26,575 | 1,515 | 18 |
| CCR7 | 32,601 | 1,862 | 18 |
| ApoA2 | 48,654 | 2,789 | 17 |
| ENA-78 | 34,130 | 1,958 | 17 |
| Myosin 18B | 32,665 | 1,878 | 17 |
| Desmoplakin | 16,073 | 924 | 17 |
| Neurabin 1 | 26,374 | 1,521 | 17 |
| FGF-4 | 28,997 | 1,676 | 17 |
| PDGF-BB | 18,974 | 1,097 | 17 |
| PCBP2 | 26,143 | 1,513 | 17 |
| P20Sb3 | 36,319 | 2,104 | 17 |
| IGF2BP1 | 19,793 | 1,149 | 17 |
| Chardin-Like 2 | 21,410 | 1,243 | 17 |
| UNC-13 Homolog D | 13,832 | 803 | 17 |
| Enolase 2 | 21,979 | 1,279 | 17 |
| Angiopoietin-2 | 45,909 | 2,675 | 17 |
| TFF2(1) | 17,923 | 1,046 | 17 |
| RHOC | 24,067 | 1,405 | 17 |
| SUMO3 | 20,328 | 1,187 | 17 |
| DGK | 34,594 | 2,022 | 17 |
| HVEM/TNFRSF14 | 25,243 | 1,478 | 17 |
| GRO-a | 28,801 | 1,687 | 17 |
| GALNT2 | 19,977 | 1,170 | 17 |
| TECK/CCL25 | 10,167 | 596 | 17 |
| Notch-1 | 20,356 | 1,194 | 17 |
| Cystatin S | 42,547 | 2,496 | 17 |
| IL-2 R alpha | 25,984 | 1,528 | 17 |
| WNK2 | 19,530 | 1,149 | 17 |
| eIF5A | 23,678 | 1,393 | 17 |
| TrypsinPan | 15,201 | 895 | 17 |
| SCF | 15,181 | 894 | 17 |
| CD30/TNFRSF8 | 30,200 | 1,783 | 17 |
| IL-1 F6/FIL1 epsilon | 21,801 | 1,288 | 17 |
| CutA | 16,929 | 1,001 | 17 |
| CFL1 | 53,170 | 3,147 | 17 |
| TRAIL R4/TNFRSF10D | 12,702 | 752 | 17 |
| MBD2 | 27,960 | 1,656 | 17 |
| UBE2N/Ubc13 | 13,689 | 812 | 17 |
| PI 16 | 25,837 | 1,535 | 17 |
| DANCE | 18,184 | 1,081 | 17 |
| FABP2 | 17,989 | 1,070 | 17 |
| IGFBP-4 | 39,803 | 2,369 | 17 |
| NEP | 17,317 | 1,032 | 17 |
| NRG1 Isoform GGF2 | 14,516 | 865 | 17 |
| IL-2 R gamma | 31,605 | 1,887 | 17 |
| MAC-1 | 25,526 | 1,527 | 17 |
| MPO | 22,503 | 1,348 | 17 |
| SerpinE2 | 16,518 | 989 | 17 |
| GDF1 | 16,860 | 1,010 | 17 |
| IL-17 | 21,768 | 1,305 | 17 |
| Orexin A | 10,971 | 658 | 17 |
| Kremen-1 | 18,568 | 1,116 | 17 |
| Smad 4 | 15,672 | 943 | 17 |
| IL-17B R | 34,269 | 2,062 | 17 |
| GCSF | 21,209 | 1,278 | 17 |
| Annexin V | 20,977 | 1,265 | 17 |
| IL-31 | 11,753 | 709 | 17 |
| TRAP1 | 15,849 | 956 | 17 |
| Transketolase/TALDO | 32,472 | 1,961 | 17 |
| pIgR | 19,122 | 1,156 | 17 |
| Brg1 | 22,575 | 1,368 | 17 |
| BMX | 24,657 | 1,494 | 17 |
| MAN1 | 22,070 | 1,338 | 17 |
| Orosomucoid 2 | 19,532 | 1,184 | 16 |
| RAP1AB | 19,947 | 1,211 | 16 |
| VEGF-B | 10,517 | 638 | 16 |
| SLC38A10 | 19,397 | 1,178 | 16 |
| RPS2 | 37,085 | 2,255 | 16 |
| RANTES | 16,051 | 977 | 16 |
| SerpinB4 | 22,437 | 1,368 | 16 |
| Nestin | 18,097 | 1,104 | 16 |
| Complement factor H | 18,375 | 1,121 | 16 |
| MAPRE1 | 21,932 | 1,342 | 16 |
| PDGF-AA | 13,401 | 820 | 16 |
| Reg1A | 19,797 | 1,212 | 16 |
| MUCDHL | 26,042 | 1,598 | 16 |
| SSTR2 | 18,703 | 1,148 | 16 |
| IGSF4B | 27,949 | 1,715 | 16 |
| TSG-6 | 17,133 | 1,052 | 16 |
| Orexin B | 20,216 | 1,241 | 16 |
| Quiescin Q6 | 16,451 | 1,011 | 16 |
| IGFBP-2 | 26,798 | 1,650 | 16 |
| IGFBP-rp1/IGFBP-7 | 24,778 | 1,526 | 16 |
| Dystroglycan | 13,218 | 815 | 16 |
| Alanine Transaminase/ALT | 25,516 | 1,574 | 16 |
| FKBP12 | 25,229 | 1,557 | 16 |
| Growth Hormone R (GHR) | 25,979 | 1,605 | 16 |
| MCP-1 | 19,729 | 1,219 | 16 |
| IL-21 | 28,485 | 1,761 | 16 |
| RANK/TNFRSF11A | 19,561 | 1,209 | 16 |
| HRG-beta 1 | 15,425 | 956 | 16 |
| ACTC1 | 25,104 | 1,556 | 16 |
| Ribonuclease T2 | 27,410 | 1,704 | 16 |
| B3GNT1 | 19,695 | 1,227 | 16 |
| Src(1) | 17,973 | 1,120 | 16 |
| PCYOX1 | 24,219 | 1,510 | 16 |
| Leptin R | 18,188 | 1,135 | 16 |
| IL-19 | 27,739 | 1,731 | 16 |
| CXCR1/IL-8 RA | 30,943 | 1,934 | 16 |
| PTP mu | 19,280 | 1,205 | 16 |
| IL-1 ra | 26,190 | 1,638 | 16 |
| PDGF-D | 12,237 | 766 | 16 |
| HEXB | 28,675 | 1,797 | 16 |
| ERp57 | 10,408 | 652 | 16 |
| PLC-gamma 1 | 28,243 | 1,771 | 16 |
| Nesprin2 | 24,670 | 1,549 | 16 |
| Frizzled-4 | 13,223 | 831 | 16 |
| B7-H2 | 32,439 | 2,040 | 16 |
| NAGLU | 25,670 | 1,615 | 16 |
| Serpin B5 | 17,301 | 1,089 | 16 |
| TNF RI/TNFRSF1A | 11,769 | 741 | 16 |
| IL-1 F9/IL-1 H1 | 25,411 | 1,601 | 16 |
| Histone H2B K | 28,635 | 1,806 | 16 |
| OX40 Ligand/TNFSF4 | 23,345 | 1,472 | 16 |
| Aminoacylase | 21,552 | 1,359 | 16 |
| Transaldolase 1/TALDO1 | 16,347 | 1,031 | 16 |
| Glucagon | 18,450 | 1,165 | 16 |
| IFRD1 | 22,022 | 1,391 | 16 |
| sFRP-4 | 14,350 | 908 | 16 |
| IL-22 | 21,050 | 1,336 | 16 |
| Kininostatin/kininogen | 15,823 | 1,005 | 16 |
| PRDM13 | 17,370 | 1,103 | 16 |
| CCR5 | 25,092 | 1,595 | 16 |
| C 1q | 39,845 | 2,534 | 16 |
| AMPKa1 | 16,149 | 1,027 | 16 |
| EXTL2 | 44,559 | 2,837 | 16 |
| POR | 19,330 | 1,232 | 16 |
| Smad 8 | 11,139 | 710 | 16 |
| TXNDC5 | 14,242 | 908 | 16 |
| IL-17RD | 15,672 | 999 | 16 |
| TREM-1 | 12,193 | 778 | 16 |
| SDNSF | 14,563 | 930 | 16 |
| FKBP51 | 30,620 | 1,956 | 16 |
| Complement Factor B | 24,127 | 1,543 | 16 |
| Cadherin-6 | 26,023 | 1,665 | 16 |
| VCAM-1 (CD106) | 15,111 | 967 | 16 |

TABLE 1-continued

| | Composition (Ex. 1) | Comparative Product X | Fold Change |
|---|---|---|---|
| 11b-HSD1 | 11,665 | 747 | 16 |
| Tie-1 | 13,154 | 844 | 16 |
| Vimentin B | 11,807 | 758 | 16 |
| DISC 1 | 33,237 | 2,133 | 16 |
| RPL7A | 24,850 | 1,601 | 16 |
| GDF-15 | 20,531 | 1,327 | 15 |
| IL-31 RA | 11,224 | 726 | 15 |
| IL-5 R alpha | 25,954 | 1,678 | 15 |
| p16 ARC | 24,766 | 1,602 | 15 |
| EN-RAGE | 17,256 | 1,117 | 15 |
| Biglycan | 15,120 | 979 | 15 |
| DSCAM | 22,416 | 1,452 | 15 |
| Aggrecan | 32,132 | 2,082 | 15 |
| DCI | 26,785 | 1,736 | 15 |
| Cathepsin A | 23,000 | 1,491 | 15 |
| HGFR | 17,385 | 1,128 | 15 |
| sFRP-1 | 12,564 | 816 | 15 |
| IL-4 R | 20,838 | 1,354 | 15 |
| IL-5 | 26,138 | 1,699 | 15 |
| FGF R3 | 31,561 | 2,052 | 15 |
| Activin RIA/ALK-2 | 28,753 | 1,871 | 15 |
| Prdx6 | 17,676 | 1,150 | 15 |
| Cathepsin L | 13,724 | 894 | 15 |
| Ezrin | 26,184 | 1,706 | 15 |
| TAX1BP3 | 69,739 | 4,554 | 15 |
| FGF-BP | 31,586 | 2,066 | 15 |
| AMICA | 12,793 | 838 | 15 |
| KMD4B | 21,577 | 1,414 | 15 |
| Artemin | 19,573 | 1,283 | 15 |
| Axl | 29,155 | 1,912 | 15 |
| Claudin-4 | 17,268 | 1,135 | 15 |
| SDF-1/CXCL12 | 26,062 | 1,715 | 15 |
| FADD | 15,311 | 1,008 | 15 |
| MAP1A | 24,358 | 1,604 | 15 |
| ABCF1 | 28,594 | 1,891 | 15 |
| Annexin A6 | 33,758 | 2,234 | 15 |
| G-CSF R/CD 114 | 24,480 | 1,622 | 15 |
| TSLP R | 8,816 | 584 | 15 |
| BRCA 2 | 24,901 | 1,653 | 15 |
| EphA2 | 18,638 | 1,241 | 15 |
| Cystatin SN | 32,506 | 2,164 | 15 |
| Fas Ligand | 24,013 | 1,600 | 15 |
| Pappalysin-1 | 15,261 | 1,018 | 15 |
| ME1 | 28,283 | 1,887 | 15 |
| 2B4 | 11,020 | 735 | 15 |
| Fe RIIB/C | 16,687 | 1,117 | 15 |
| Dkk-4 | 28,306 | 1,895 | 15 |
| alpha-Synuclein | 28,760 | 1,927 | 15 |
| Neural Cadherin | 33,750 | 2,265 | 15 |
| ANGPTL3 | 22,632 | 1,520 | 15 |
| C 1q S | 33,191 | 2,232 | 15 |
| ATBF1/ZFHX3 | 31,056 | 2,089 | 15 |
| IGF-I | 20,986 | 1,412 | 15 |
| IL-3 | 19,203 | 1,292 | 15 |
| IL-3 R alpha | 23,009 | 1,549 | 15 |
| Semaphorin 6B | 22,347 | 1,504 | 15 |
| DPPIV | 16,714 | 1,126 | 15 |
| LAMP2 | 32,187 | 2,169 | 15 |
| Angiopoietin-like 1 | 32,815 | 2,211 | 15 |
| ERAP2 | 19,198 | 1,294 | 15 |
| PCDX8 | 20,443 | 1,378 | 15 |
| ALKP | 19,849 | 1,339 | 15 |
| TMEFF2 | 9,761 | 659 | 15 |
| IFN-alpha/beta R2 | 14,863 | 1,003 | 15 |
| STOM | 35,805 | 2,418 | 15 |
| HSP20 | 17,410 | 1,176 | 15 |
| Ck beta 8-1 | 13,926 | 941 | 15 |
| IL-2 R beta/CD122 | 26,777 | 1,809 | 15 |
| NrCAM | 24,989 | 1,690 | 15 |
| MMRN1 | 17,082 | 1,157 | 15 |
| OSCAR | 25,990 | 1,761 | 15 |
| IL-21 R | 16,314 | 1,106 | 15 |
| PTMA | 26,420 | 1,792 | 15 |
| BLMH | 20,162 | 1,368 | 15 |
| PLS3 | 28,956 | 1,965 | 15 |
| IL-10 | 21,240 | 1,442 | 15 |
| CPM | 32,328 | 2,197 | 15 |
| cIAP-2 | 11,722 | 797 | 15 |
| Pref-1 | 22,136 | 1,508 | 15 |
| GASP-1/WFIKKNRP | 25,644 | 1,747 | 15 |
| FAP | 16,380 | 1,118 | 15 |
| Fibrinogen | 42,805 | 2,922 | 15 |
| PPCS | 18,634 | 1,272 | 15 |
| LFA-1 alpha | 16,196 | 1,106 | 15 |
| Mcl-1 | 27,582 | 1,887 | 15 |
| DcR3/TNFRSF6B | 26,742 | 1,830 | 15 |
| Mesothelin | 15,354 | 1,052 | 15 |
| TACI/TNFRSF13B | 28,735 | 1,973 | 15 |
| Chemerin | 17,506 | 1,202 | 15 |
| WISP2 | 23,342 | 1,607 | 15 |
| GM-CSF | 18,296 | 1,261 | 15 |
| DLL4 | 14,364 | 991 | 14 |
| TLS/FUS | 14,659 | 1,012 | 14 |
| AGA | 17,036 | 1,177 | 14 |
| BTC | 30,096 | 2,080 | 14 |
| Chromogranin B | 20,797 | 1,439 | 14 |
| HMGB3 | 19,679 | 1,362 | 14 |
| CFVII | 29,061 | 2,017 | 14 |
| Cryptic | 28,697 | 1,993 | 14 |
| CCR6 | 24,127 | 1,676 | 14 |
| CrkL | 20,032 | 1,393 | 14 |
| 14-3-3 beta | 16,975 | 1,182 | 14 |
| TGF-beta RI/ALK-5 | 8,778 | 612 | 14 |
| EphA1 | 24,362 | 1,699 | 14 |
| Trypsin 1 | 18,179 | 1,268 | 14 |
| Lipocalin-1 | 22,281 | 1,557 | 14 |
| Podocalyxin | 19,415 | 1,357 | 14 |
| sgp130 | 21,215 | 1,484 | 14 |
| Lipocalin-2 | 18,380 | 1,286 | 14 |
| Caspase-3 | 11,632 | 815 | 14 |
| ITIH4 a | 18,698 | 1,310 | 14 |
| FSH | 16,769 | 1,175 | 14 |
| Ras | 12,226 | 857 | 14 |
| PTP kappa | 17,441 | 1,227 | 14 |
| TIMP-1 | 11,955 | 843 | 14 |
| Calsyntenin-1 | 14,735 | 1,040 | 14 |
| MARCKS | 23,174 | 1,636 | 14 |
| ARP19 | 17,822 | 1,261 | 14 |
| Fibronectin | 21,800 | 1,544 | 14 |
| Activin RIB/ALK-4 | 27,338 | 1,936 | 14 |
| Chitobiase | 34,121 | 2,419 | 14 |
| OSBP1 | 25,462 | 1,805 | 14 |
| IL-23 | 11,722 | 831 | 14 |
| IL-12 R beta 1 | 24,178 | 1,715 | 14 |
| GCSH | 38,747 | 2,749 | 14 |
| PLOD2 | 17,373 | 1,233 | 14 |
| Nectin-3 | 21,640 | 1,537 | 14 |
| GRP75 | 15,350 | 1,091 | 14 |
| Soggy-1 | 21,783 | 1,548 | 14 |
| MIP-3 alpha | 12,400 | 881 | 14 |
| GFR alpha-4 | 26,319 | 1,876 | 14 |
| HMGB1 | 24,395 | 1,741 | 14 |
| PCK2 | 25,024 | 1,786 | 14 |
| LRP-1 | 19,282 | 1,378 | 14 |
| MMP-8 | 24,721 | 1,767 | 14 |
| HSP70 | 21,327 | 1,526 | 14 |
| EPCR | 26,477 | 1,894 | 14 |
| Epiregulin | 23,195 | 1,660 | 14 |
| Gas1 | 17,800 | 1,275 | 14 |
| CTLA-4/CD152 | 28,714 | 2,058 | 14 |
| IL-27 | 12,538 | 899 | 14 |
| TGF-beta 1 | 22,019 | 1,583 | 14 |
| Attractin | 15,292 | 1,099 | 14 |
| BNIP2 | 20,774 | 1,495 | 14 |
| BMP-5 | 21,307 | 1,535 | 14 |
| PKLR | 23,555 | 1,698 | 14 |
| CCR3 | 26,579 | 1,916 | 14 |
| Histone H2A | 15,496 | 1,118 | 14 |
| PDGF-C | 13,580 | 980 | 14 |
| IL-17B | 27,758 | 2,005 | 14 |
| Osteoactivin/GPNMB | 17,750 | 1,284 | 14 |
| CPE | 23,356 | 1,690 | 14 |

TABLE 1-continued

|  | Composition (Ex. 1) | Comparative Product X | Fold Change |
|---|---|---|---|
| CD40/TNFRSF5 | 25,587 | 1,853 | 14 |
| CA1 | 32,731 | 2,371 | 14 |
| Triosephosphate isomerase/TPIS | 8,857 | 642 | 14 |
| ADAMTS-17 | 18,090 | 1,312 | 14 |
| EYA2 | 21,449 | 1,557 | 14 |
| GFR alpha-1 | 15,007 | 1,089 | 14 |
| Amylin | 41,786 | 3,036 | 14 |
| DMP-1 | 13,760 | 1,001 | 14 |
| NUP98 | 24,583 | 1,788 | 14 |
| SERPING1 | 19,916 | 1,451 | 14 |
| CKB | 31,492 | 2,297 | 14 |
| CCR2 | 16,385 | 1,195 | 14 |
| pro-MMP13 | 11,194 | 817 | 14 |
| ApoC1 | 21,874 | 1,596 | 14 |
| Glucose 6 Phosphate Dehydrogenase/G6PD | 33,245 | 2,426 | 14 |
| Caldesmon/CALD1 | 27,072 | 1,979 | 14 |
| TLR2 | 9,606 | 702 | 14 |
| NGF R | 15,861 | 1,160 | 14 |
| PSA-Free | 19,062 | 1,395 | 14 |
| COCO | 17,843 | 1,307 | 14 |
| MRP 1 | 24,512 | 1,797 | 14 |
| MCAM | 29,993 | 2,203 | 14 |
| GRP78 | 19,150 | 1,410 | 14 |
| IL-9 | 23,601 | 1,738 | 14 |
| IL-1 R9 | 16,172 | 1,194 | 14 |
| NAIP | 21,107 | 1,559 | 14 |
| RBP4 | 18,599 | 1,374 | 14 |
| PABP | 23,000 | 1,701 | 14 |
| CEACAM-1 | 14,087 | 1,043 | 14 |
| ADAMTS-5 | 22,125 | 1,639 | 13 |
| ALPP | 27,361 | 2,028 | 13 |
| GPX1 | 14,338 | 1,064 | 13 |
| Cathepsin X/Z/P | 24,495 | 1,819 | 13 |
| ApoB | 13,243 | 984 | 13 |
| Contactin-2 | 17,865 | 1,329 | 13 |
| LRP-6 | 12,871 | 959 | 13 |
| MMP-2 | 21,512 | 1,603 | 13 |
| MFRP | 17,695 | 1,321 | 13 |
| Survivin | 14,394 | 1,077 | 13 |
| Siglec-1 | 12,748 | 954 | 13 |
| PD-ECGF | 27,988 | 2,094 | 13 |
| cTnT | 21,985 | 1,645 | 13 |
| Thioredoxin-1 | 18,018 | 1,350 | 13 |
| PGD | 24,343 | 1,824 | 13 |
| RPS23 | 12,653 | 949 | 13 |
| TPX | 15,924 | 1,194 | 13 |
| LAMP | 21,609 | 1,624 | 13 |
| Myotrophin | 23,751 | 1,786 | 13 |
| SSTR5 | 15,956 | 1,200 | 13 |
| IP-10 | 18,137 | 1,365 | 13 |
| PGRPL | 28,556 | 2,151 | 13 |
| GDF7 | 35,383 | 2,666 | 13 |
| FAM20C | 21,716 | 1,638 | 13 |
| ARFBP1 | 66,135 | 4,993 | 13 |
| Activin RIIA | 23,804 | 1,799 | 13 |
| Sonic Hedgehog (Shh N-terminal) | 23,283 | 1,760 | 13 |
| ApoC2 | 11,918 | 901 | 13 |
| CFI | 34,438 | 2,606 | 13 |
| Adipsin | 17,643 | 1,335 | 13 |
| C7 | 23,445 | 1,777 | 13 |
| ApoM | 10,437 | 791 | 13 |
| HRG | 19,505 | 1,482 | 13 |
| Fibulin 3 | 21,023 | 1,597 | 13 |
| HINT1 | 20,694 | 1,573 | 13 |
| GPBB | 17,496 | 1,335 | 13 |
| GDF5 | 32,503 | 2,485 | 13 |
| Histone H1.3 | 16,018 | 1,226 | 13 |
| RELM beta | 15,967 | 1,223 | 13 |
| glutathione S transferase Omega 1/GSTO1 | 20,548 | 1,575 | 13 |
| Serpin A3 | 18,682 | 1,433 | 13 |
| ErbB2 | 22,810 | 1,751 | 13 |
| XIAP | 13,150 | 1,010 | 13 |
| IBSP | 13,928 | 1,070 | 13 |
| MICA | 18,327 | 1,409 | 13 |
| Desmocollin-3 | 12,281 | 944 | 13 |
| Prolactin | 24,655 | 1,896 | 13 |
| Leptin (OB) | 15,996 | 1,232 | 13 |
| WISP-1/CCN4 | 12,639 | 974 | 13 |
| Aldolase B | 12,926 | 997 | 13 |
| NPAS3 | 21,153 | 1,635 | 13 |
| LOX-1 | 12,870 | 996 | 13 |
| hnRNP G | 17,601 | 1,364 | 13 |
| PACS1 | 20,636 | 1,599 | 13 |
| BIK | 17,348 | 1,347 | 13 |
| Glycerol 3 Phosphate Dehydrogenase | 30,027 | 2,331 | 13 |
| Olfactomedin-2 | 14,050 | 1,091 | 13 |
| GFR alpha-2 | 19,167 | 1,489 | 13 |
| MSH6 | 24,882 | 1,938 | 13 |
| ANGPTL4 | 11,861 | 926 | 13 |
| Prouroguanylin | 32,028 | 2,501 | 13 |
| PHAP1 | 27,112 | 2,118 | 13 |
| FKBP25 | 20,104 | 1,572 | 13 |
| BMP-8 | 22,135 | 1,733 | 13 |
| CFHR 1 | 18,843 | 1,476 | 13 |
| Osteocalcin | 13,329 | 1,044 | 13 |
| HBZ | 18,451 | 1,447 | 13 |
| HOXD11 | 22,083 | 1,733 | 13 |
| LEDGF | 22,979 | 1,805 | 13 |
| NeuroD1 | 12,350 | 971 | 13 |
| RanGAP1 | 19,746 | 1,552 | 13 |
| NF-M | 21,326 | 1,677 | 13 |
| SOX17 | 15,311 | 1,204 | 13 |
| PYY | 20,286 | 1,598 | 13 |
| IL-20 | 20,679 | 1,629 | 13 |
| Cytochrome c | 18,900 | 1,491 | 13 |
| IL-15 | 27,903 | 2,205 | 13 |
| CA 15-3 | 19,348 | 1,529 | 13 |
| Hemoglobin | 15,999 | 1,265 | 13 |
| DCBLD2 | 12,855 | 1,017 | 13 |
| Serpin I1 | 10,904 | 864 | 13 |
| DLL1 | 14,354 | 1,137 | 13 |
| FGF-21 | 12,809 | 1,016 | 13 |
| RNASE6 | 14,716 | 1,168 | 13 |
| Annexin A7 | 11,296 | 897 | 13 |
| PCCA | 35,047 | 2,787 | 13 |
| GLIPR2 | 25,308 | 2,018 | 13 |
| Desmuslin | 29,335 | 2,343 | 13 |
| C9 | 20,378 | 1,628 | 13 |
| Proteasome 20S b7 | 26,068 | 2,084 | 13 |
| ARX | 11,876 | 950 | 12 |
| LIF R alpha | 14,718 | 1,178 | 12 |
| C1s | 35,810 | 2,870 | 12 |
| Chymase | 13,436 | 1,078 | 12 |
| Prion protein PrP/PRNP | 25,503 | 2,047 | 12 |
| IFN-gamma | 21,005 | 1,686 | 12 |
| CNOT1 | 18,773 | 1,513 | 12 |
| UROD | 9,863 | 796 | 12 |
| IL-1 R6/IL-1 Rrp2 | 17,839 | 1,441 | 12 |
| PER1 | 26,283 | 2,124 | 12 |
| CFHR2 | 14,126 | 1,143 | 12 |
| Thymidine Kinase-1 | 22,402 | 1,814 | 12 |
| PTP gamma | 17,115 | 1,387 | 12 |
| LBP | 11,208 | 910 | 12 |
| BCAM | 21,449 | 1,743 | 12 |
| NM23-H1/H2 | 11,865 | 965 | 12 |
| Lysozyme | 21,909 | 1,785 | 12 |
| Frizzled-5 | 13,106 | 1,068 | 12 |
| PARC/CCL18 | 22,168 | 1,808 | 12 |
| ROR1 | 17,770 | 1,451 | 12 |
| Serpin A8 | 13,335 | 1,089 | 12 |
| Persephin | 16,031 | 1,309 | 12 |
| IL-13 R alpha 1 | 23,204 | 1,897 | 12 |
| IGFBP-3 | 20,671 | 1,690 | 12 |
| Neurturin | 15,921 | 1,302 | 12 |
| perilipin 3 | 27,977 | 2,288 | 12 |
| PSMB5 | 28,746 | 2,353 | 12 |
| PLUNC | 15,583 | 1,278 | 12 |
| Cathepsin G | 11,916 | 978 | 12 |
| Siglec-9 | 19,524 | 1,603 | 12 |

TABLE 1-continued

| | Composition (Ex. 1) | Comparative Product X | Fold Change |
|---|---|---|---|
| MMP-15 | 20,236 | 1,663 | 12 |
| Frizzled-7 | 14,450 | 1,188 | 12 |
| ARB1 | 16,372 | 1,346 | 12 |
| CL-P1 | 22,520 | 1,855 | 12 |
| Glypican 3 | 9,888 | 815 | 12 |
| MFG-E8 | 17,371 | 1,431 | 12 |
| GATA-3 | 13,033 | 1,074 | 12 |
| Frizzled-6 | 12,262 | 1,012 | 12 |
| beta B1 Crystallin/CRYBB1 | 30,557 | 2,523 | 12 |
| Siglec-5/CD170 | 19,094 | 1,578 | 12 |
| TOPORS | 17,006 | 1,406 | 12 |
| PIN | 24,926 | 2,062 | 12 |
| Hemoglobin A1c | 24,492 | 2,026 | 12 |
| S100A8 | 13,776 | 1,140 | 12 |
| EphB4 | 11,455 | 948 | 12 |
| CLC | 28,310 | 2,348 | 12 |
| Cystatin A | 13,139 | 1,090 | 12 |
| Transthyretin | 8,359 | 695 | 12 |
| GSR | 21,738 | 1,807 | 12 |
| GAPDH | 33,874 | 2,821 | 12 |
| Trappin-2 | 10,521 | 876 | 12 |
| Plastin L | 32,790 | 2,732 | 12 |
| PSMA1 | 12,406 | 1,034 | 12 |
| Cathepsin S | 11,811 | 987 | 12 |
| IGFBP-5 | 10,509 | 879 | 12 |
| LILRA3 | 21,136 | 1,770 | 12 |
| GITR Ligand/TNFSF18 | 26,583 | 2,227 | 12 |
| KRT31 | 25,914 | 2,171 | 12 |
| KCTD10 | 11,852 | 993 | 12 |
| BTD | 35,736 | 2,995 | 12 |
| LYVE-1 | 11,219 | 942 | 12 |
| ACE | 12,738 | 1,069 | 12 |
| ECM-1 | 26,136 | 2,195 | 12 |
| ZNF671 | 8,853 | 744 | 12 |
| FoxP3 | 11,982 | 1,007 | 12 |
| ROBO4 | 12,349 | 1,039 | 12 |
| Cystatin C | 17,281 | 1,455 | 12 |
| BIRC6 | 33,912 | 2,857 | 12 |
| Vitronectin | 16,789 | 1,415 | 12 |
| beta-Catenin | 10,687 | 901 | 12 |
| beta -I Tubulin | 19,039 | 1,606 | 12 |
| E-Cadherin | 15,550 | 1,313 | 12 |
| IL-1 sRII | 18,520 | 1,565 | 12 |
| Plectin | 24,920 | 2,109 | 12 |
| Spinesin | 15,999 | 1,354 | 12 |
| Endorepellin | 16,550 | 1,402 | 12 |
| Glut2 | 16,138 | 1,368 | 12 |
| Insulin R | 20,894 | 1,774 | 12 |
| Serpin D1 | 9,910 | 845 | 12 |
| Azurocidin | 19,931 | 1,699 | 12 |
| RPS10 | 20,711 | 1,765 | 12 |
| Catalase | 11,833 | 1,009 | 12 |
| Glut5 | 18,755 | 1,601 | 12 |
| HAI-2 | 11,962 | 1,021 | 12 |
| FGFR1 alpha | 20,102 | 1,716 | 12 |
| S100A4 | 11,037 | 943 | 12 |
| ARPC3 | 31,306 | 2,675 | 12 |
| Properdin | 23,270 | 1,989 | 12 |
| Glyoxalase II | 9,950 | 851 | 12 |
| Netrin-4 | 17,000 | 1,453 | 12 |
| FABP3 | 15,508 | 1,327 | 12 |
| ZBTB4 | 11,158 | 955 | 12 |
| LIMPII | 9,671 | 828 | 12 |
| Neuritin | 15,303 | 1,311 | 12 |
| BMP-3b/GDF-10 | 10,866 | 931 | 12 |
| Vasorin | 14,981 | 1,287 | 12 |
| Cortactin | 12,599 | 1,084 | 12 |
| Cystatin D | 34,225 | 2,945 | 12 |
| Smad 1 | 10,319 | 889 | 12 |
| MCP-4/CCL13 | 11,857 | 1,023 | 12 |
| Syndecan-1 | 12,293 | 1,061 | 12 |
| Osteopontin | 12,689 | 1,098 | 12 |
| ApoE | 11,628 | 1,009 | 12 |
| APN | 14,701 | 1,276 | 12 |
| IFN-alpha/beta R1 | 12,426 | 1,079 | 12 |
| Fas/TNFRSF6 | 16,250 | 1,412 | 12 |
| Erythropoietin | 23,681 | 2,059 | 12 |
| ApoB100 | 10,424 | 907 | 11 |
| Cathepsin H | 18,404 | 1,602 | 11 |
| TWEAK/TNFSF12 | 9,556 | 832 | 11 |
| Chordin-Like 1 | 17,692 | 1,542 | 11 |
| Pentraxin3/TSG-14 | 13,010 | 1,136 | 11 |
| AFP | 19,423 | 1,697 | 11 |
| CD61 | 14,932 | 1,305 | 11 |
| Cathepsin D | 13,552 | 1,185 | 11 |
| DOT1L | 26,325 | 2,303 | 11 |
| Desmocollin-2 | 16,532 | 1,447 | 11 |
| URB | 7,900 | 692 | 11 |
| PRSS3 | 34,998 | 3,065 | 11 |
| MASP3 | 16,807 | 1,472 | 11 |
| ADAMTS-19 | 17,518 | 1,535 | 11 |
| Ephrin B1 | 32,348 | 2,839 | 11 |
| TGF-beta 3 | 5,519 | 485 | 11 |
| ApoH | 13,306 | 1,169 | 11 |
| ALDH1A1 | 17,032 | 1,497 | 11 |
| Nectin-1 | 13,476 | 1,186 | 11 |
| GFAP | 10,095 | 889 | 11 |
| KLK-B1 | 11,245 | 992 | 11 |
| Secretogranin V/SCG5 | 26,389 | 2,329 | 11 |
| Peroxiredoxin 3 | 24,889 | 2,197 | 11 |
| EphB6 | 11,747 | 1,039 | 11 |
| MYHC | 24,624 | 2,177 | 11 |
| NABC1 | 14,986 | 1,326 | 11 |
| PSMD1 | 28,696 | 2,542 | 11 |
| AgRP | 25,506 | 2,263 | 11 |
| IL-23 R | 12,193 | 1,082 | 11 |
| Galanin | 19,866 | 1,772 | 11 |
| PIK3IP1 | 15,876 | 1,419 | 11 |
| IL-1 F10/IL-1HY2 | 14,933 | 1,335 | 11 |
| IL-28A | 12,491 | 1,119 | 11 |
| SOX4 | 23,277 | 2,091 | 11 |
| ANK | 18,919 | 1,701 | 11 |
| PON1 | 12,350 | 1,112 | 11 |
| Uromodulin | 11,681 | 1,052 | 11 |
| PPOX | 68,229 | 6,146 | 11 |
| Histone H4 | 16,945 | 1,527 | 11 |
| Metallothionein | 21,390 | 1,932 | 11 |
| FOLR3 | 25,145 | 2,271 | 11 |
| Neurokinin-A | 11,453 | 1,035 | 11 |
| Protein p65 | 12,098 | 1,093 | 11 |
| IL-33 | 14,059 | 1,271 | 11 |
| HDGF | 10,307 | 932 | 11 |
| APLP-1 | 17,989 | 1,628 | 11 |
| Frizzled-3 | 10,860 | 983 | 11 |
| PGRP-S | 10,093 | 914 | 11 |
| SOD4 | 21,887 | 1,983 | 11 |
| SERPINB1 | 17,880 | 1,620 | 11 |
| Tenascin C | 9,478 | 859 | 11 |
| GMF beta | 21,813 | 1,977 | 11 |
| Fyn | 14,718 | 1,335 | 11 |
| HPR | 23,855 | 2,164 | 11 |
| Neuropilin-2 | 12,929 | 1,174 | 11 |
| Lamin A + C | 17,020 | 1,545 | 11 |
| ZC3H4-N-t | 7,586 | 689 | 11 |
| GSTP1 | 9,959 | 905 | 11 |
| PON2 | 15,027 | 1,366 | 11 |
| DCXR | 36,583 | 3,326 | 11 |
| GRO | 19,747 | 1,796 | 11 |
| Hornerin | 21,824 | 1,987 | 11 |
| COX-2 | 11,446 | 1,043 | 11 |
| S100A10 | 11,005 | 1,003 | 11 |
| 53BP1 | 10,818 | 986 | 11 |
| PKM2 | 11,338 | 1,034 | 11 |
| S-100b | 21,976 | 2,004 | 11 |
| Lamin B1 | 17,999 | 1,643 | 11 |
| PZP | 13,658 | 1,247 | 11 |
| Chitotriosidase | 18,483 | 1,688 | 11 |
| Osteocrin | 13,127 | 1,200 | 11 |
| PlGF | 14,642 | 1,340 | 11 |
| LOK | 25,305 | 2,316 | 11 |
| ALBUMIN | 393,095 | 35,987 | 11 |
| SHANK1 | 10,900 | 1,000 | 11 |

TABLE 1-continued

| | Composition (Ex. 1) | Comparative Product X | Fold Change |
|---|---|---|---|
| TLR1 | 10,942 | 1,004 | 11 |
| HADHA | 20,020 | 1,837 | 11 |
| ApoD | 12,609 | 1,159 | 11 |
| PA2G4 | 22,780 | 2,096 | 11 |
| KIF3B | 14,052 | 1,294 | 11 |
| Ubiquitin + 1 | 20,890 | 1,924 | 11 |
| TXNRD2 | 22,225 | 2,048 | 11 |
| Eotaxin/CCL11 | 11,692 | 1,078 | 11 |
| HCFC1 | 9,083 | 838 | 11 |
| IL-20 R beta | 16,265 | 1,500 | 11 |
| Pancreastatin | 18,187 | 1,678 | 11 |
| FGF-10/KGF-2 | 24,214 | 2,238 | 11 |
| Brevican | 32,087 | 2,967 | 11 |
| CES1 | 13,529 | 1,253 | 11 |
| TIMP-2 | 7,625 | 709 | 11 |
| MMP-10 | 17,280 | 1,612 | 11 |
| CD30 Ligand/TNFSF8 | 16,618 | 1,554 | 11 |
| GIP | 16,022 | 1,498 | 11 |
| Kallikrein 10 | 17,316 | 1,622 | 11 |
| Ficolin-3 | 12,019 | 1,127 | 11 |
| HNF-3 alpha/FoxA1 | 9,474 | 889 | 11 |
| Thyroglobulin | 19,221 | 1,806 | 11 |
| TFPI | 9,557 | 898 | 11 |
| ICAM-3 (CD50) | 8,473 | 797 | 11 |
| RPL14 | 27,715 | 2,607 | 11 |
| S100A9 | 10,524 | 992 | 11 |
| CA2 | 25,433 | 2,397 | 11 |
| Hoxb3 | 25,742 | 2,427 | 11 |
| Serpin A9 | 9,448 | 891 | 11 |
| IL-20 R alpha | 20,061 | 1,896 | 11 |
| TFF1 | 15,618 | 1,476 | 11 |
| Pro-BDNF | 12,610 | 1,193 | 11 |
| NCAM2 | 22,340 | 2,115 | 11 |
| NPTXR | 12,663 | 1,200 | 11 |
| Guanylin | 23,174 | 2,196 | 11 |
| ALP | 23,389 | 2,217 | 11 |
| TMEFF1/Tomoregulin-1 | 14,826 | 1,406 | 11 |
| PSA-total | 14,934 | 1,417 | 11 |
| KIAA1468 | 24,926 | 2,367 | 11 |
| IL-7 R alpha | 13,163 | 1,250 | 11 |
| HSP10 | 15,512 | 1,474 | 11 |
| GASP-2/WFIKKN | 14,876 | 1,414 | 11 |
| SLPI | 16,991 | 1,616 | 11 |
| Neogenin | 15,240 | 1,453 | 10 |
| Cerberus 1 | 13,329 | 1,274 | 10 |
| PSMA7 | 18,938 | 1,811 | 10 |
| Beta Defensin 4 | 14,037 | 1,345 | 10 |
| FIH | 16,893 | 1,621 | 10 |
| CHC17 | 11,811 | 1,134 | 10 |
| Semenogelin I/SEMG1 | 12,988 | 1,248 | 10 |
| hHR23b | 25,816 | 2,480 | 10 |
| Proteasome 20S alpha | 28,990 | 2,785 | 10 |
| Histone H3.3 | 12,968 | 1,246 | 10 |
| SOST | 12,665 | 1,218 | 10 |
| EV15L | 18,278 | 1,759 | 10 |
| Fetuin A | 15,796 | 1,521 | 10 |
| Fetuin B | 14,710 | 1,419 | 10 |
| GULP1/CED-6 | 8,837 | 853 | 10 |
| WIF-1 | 8,303 | 802 | 10 |
| GDF3 | 22,278 | 2,152 | 10 |
| INSL3 | 14,768 | 1,428 | 10 |
| APC | 19,874 | 1,922 | 10 |
| TSLP | 10,278 | 994 | 10 |
| ROCK1 | 26,088 | 2,527 | 10 |
| TRA-1-60 | 20,295 | 1,967 | 10 |
| HOXA10 | 11,787 | 1,143 | 10 |
| MYH7 | 30,234 | 2,934 | 10 |
| ACLY | 26,989 | 2,624 | 10 |
| EVC2 | 32,549 | 3,168 | 10 |
| CTGF/CCN2 | 15,131 | 1,473 | 10 |
| TRA-1-81 | 20,176 | 1,965 | 10 |
| 14-3-3 sigma | 11,410 | 1,111 | 10 |
| NELL2 | 19,975 | 1,945 | 10 |
| Ferritin | 17,436 | 1,700 | 10 |
| Cytochrome C | 13,682 | 1,336 | 10 |
| B3GNT2 | 34,350 | 3,368 | 10 |
| Fibrinopeptide A | 17,802 | 1,746 | 10 |
| PISD | 29,273 | 2,873 | 10 |
| SAMSN1 | 9,699 | 952 | 10 |
| Glut3 | 23,318 | 2,289 | 10 |
| HSP40 | 11,379 | 1,118 | 10 |
| PD-1 | 9,723 | 956 | 10 |
| PDGF R beta | 21,814 | 2,145 | 10 |
| SNCG | 13,038 | 1,283 | 10 |
| ROCK2 | 10,959 | 1,079 | 10 |
| CRTH-2 | 13,486 | 1,329 | 10 |
| MP1 | 13,087 | 1,291 | 10 |
| CD200 | 10,717 | 1,058 | 10 |
| PDIA6 | 48,676 | 4,808 | 10 |
| Grb2 | 9,662 | 955 | 10 |
| CNTF R alpha | 23,160 | 2,290 | 10 |
| F11 | 23,087 | 2,286 | 10 |
| Frizzled-1 | 10,409 | 1,033 | 10 |
| BMP-9 | 11,732 | 1,166 | 10 |
| ROR2 | 12,403 | 1,234 | 10 |
| L-Selectin (CD62L) | 18,250 | 1,816 | 10 |
| Clusterin | 28,326 | 2,820 | 10 |
| AKR1C3 | 13,212 | 1,317 | 10 |
| NCAM-1/CD56 | 12,556 | 1,252 | 10 |
| S100P | 7,571 | 757 | 10 |
| COMP | 17,210 | 1,721 | 10 |
| FGFR1 | 24,579 | 2,461 | 10 |
| PARK7 | 11,114 | 1,116 | 10 |
| Laminin 2 alpha | 28,122 | 2,824 | 10 |
| PI 3-Kinase C2 beta | 16,361 | 1,645 | 10 |
| IRE1 | 19,601 | 1,971 | 10 |
| Filamin B | 28,758 | 2,892 | 10 |
| NT5C3 | 16,181 | 1,628 | 10 |
| Lumican | 12,928 | 1,302 | 10 |
| FGFR2 | 11,606 | 1,169 | 10 |
| AIF | 10,471 | 1,055 | 10 |
| IL-34 | 12,580 | 1,268 | 10 |
| Multimerin 2 | 27,651 | 2,788 | 10 |
| Latent TGF beta bp2 | 16,485 | 1,665 | 10 |
| ADM | 20,656 | 2,089 | 10 |
| Inhibin beta | 36,341 | 3,680 | 10 |
| FOLR1 | 13,583 | 1,377 | 10 |
| SET | 16,836 | 1,708 | 10 |
| Progranulin | 11,457 | 1,165 | 10 |
| RELM alpha | 13,733 | 1,399 | 10 |
| Endothelin Receptor A | 25,402 | 2,588 | 10 |
| FABP4 | 10,780 | 1,102 | 10 |
| PPP2R5C | 18,026 | 1,849 | 10 |
| ApoE3 | 10,881 | 1,117 | 10 |
| MN1 | 25,457 | 2,618 | 10 |
| RPS12 | 19,459 | 2,002 | 10 |
| MLCK | 24,528 | 2,535 | 10 |
| INSRR | 12,952 | 1,340 | 10 |
| 14-3-3 epsilon | 9,547 | 988 | 10 |
| HP1BP3 | 20,081 | 2,079 | 10 |
| Perilipin-1 | 24,670 | 2,555 | 10 |
| Furin | 12,443 | 1,289 | 10 |
| ABL1 | 14,878 | 1,541 | 10 |
| Mannosidase II | 26,978 | 2,796 | 10 |
| IL-17E | 16,876 | 1,751 | 10 |
| Grainyhead-like protein 1 homolog/GRHL1 | 13,556 | 1,407 | 10 |
| Neurotrimin | 16,955 | 1,759 | 10 |
| CLIC1 | 25,403 | 2,636 | 10 |
| LOXL1 | 22,311 | 2,321 | 10 |
| 14-3-3 theta | 10,852 | 1,130 | 10 |
| RhoGDI | 17,744 | 1,851 | 10 |
| ACTH | 16,988 | 1,776 | 10 |
| Afamin | 8,612 | 901 | 10 |
| FBPase 1 | 11,548 | 1,209 | 10 |
| Plasminogen | 10,100 | 1,058 | 10 |
| Kallikrein 11 | 12,470 | 1,306 | 10 |
| Desmoglein-1 | 14,365 | 1,505 | 10 |
| Myoglobin | 11,762 | 1,232 | 10 |
| Contactin-4 | 23,432 | 2,458 | 10 |
| PECAM-1/CD31 | 9,641 | 1,012 | 10 |
| ADH1C | 29,910 | 3,143 | 10 |

TABLE 1-continued

| | Composition (Ex. 1) | Comparative Product X | Fold Change |
|---|---|---|---|
| ATP5O | 35,641 | 3,745 | 10 |
| NOV/CCN3 | 8,775 | 925 | 9 |
| CRTAM | 14,936 | 1,575 | 9 |
| Serpin B3/SCCA1 | 6,547 | 691 | 9 |
| MBL | 10,337 | 1,092 | 9 |
| CA 125 | 20,079 | 2,123 | 9 |
| Smad 7 | 11,775 | 1,250 | 9 |
| Growth Hormone (GH) | 19,096 | 2,028 | 9 |
| OX40 | 13,382 | 1,421 | 9 |
| Serpin A5 | 14,822 | 1,575 | 9 |
| TRP-1 | 7,105 | 755 | 9 |
| PEPSINOGEN II | 10,821 | 1,151 | 9 |
| PEBP4 | 27,601 | 2,937 | 9 |
| mTOR | 17,890 | 1,904 | 9 |
| hnRNP L | 27,909 | 2,975 | 9 |
| TACE | 6,946 | 743 | 9 |
| 14-3-3 eta | 9,736 | 1,042 | 9 |
| IL-17C | 9,667 | 1,035 | 9 |
| MMP-7 | 7,507 | 804 | 9 |
| Kallikrein 7 | 11,843 | 1,269 | 9 |
| AFG3L2 | 26,067 | 2,795 | 9 |
| VEGI/TNFSF15 | 8,610 | 923 | 9 |
| APP | 14,183 | 1,521 | 9 |
| LAIR1 | 12,318 | 1,321 | 9 |
| Ran | 16,300 | 1,750 | 9 |
| Kallikrein 14 | 9,265 | 997 | 9 |
| HSP90 | 14,336 | 1,542 | 9 |
| Nesfatin | 14,048 | 1,512 | 9 |
| p27 | 13,818 | 1,489 | 9 |
| TIM-1 | 9,656 | 1,041 | 9 |
| Pancreatic Polypeptide | 17,427 | 1,879 | 9 |
| MYO5A | 30,334 | 3,277 | 9 |
| CPNE3 | 34,289 | 3,706 | 9 |
| Peroxiredoxin 2 | 9,101 | 985 | 9 |
| Nebulin | 27,898 | 3,020 | 9 |
| Aldehyde Oxidase 1/AOX1 | 10,993 | 1,190 | 9 |
| BAZ2B | 30,281 | 3,280 | 9 |
| Actinin alpha 1 | 11,273 | 1,222 | 9 |
| CA3 | 34,206 | 3,720 | 9 |
| CCT3 | 42,119 | 4,581 | 9 |
| MMR | 15,277 | 1,666 | 9 |
| Progesterone | 13,727 | 1,498 | 9 |
| HMGB2 | 24,511 | 2,680 | 9 |
| PDX-1 | 11,126 | 1,217 | 9 |
| Gastrokine 1 | 11,923 | 1,305 | 9 |
| Factor XIII | 24,822 | 2,720 | 9 |
| TGF-beta 2 | 8,701 | 956 | 9 |
| MMP-12 | 14,227 | 1,567 | 9 |
| Caspase-8 | 21,352 | 2,355 | 9 |
| PSMC3 | 18,155 | 2,003 | 9 |
| ITM2B | 10,106 | 1,119 | 9 |
| PDLIM1 | 19,468 | 2,155 | 9 |
| Plexin B1 | 8,623 | 955 | 9 |
| H6PD | 18,509 | 2,053 | 9 |
| IL-12 p70 | 12,656 | 1,405 | 9 |
| NAP1L1 | 30,042 | 3,338 | 9 |
| NPM1 | 9,222 | 1,025 | 9 |
| LRP 4 | 17,002 | 1,893 | 9 |
| Prostasin | 10,235 | 1,141 | 9 |
| p21 | 20,176 | 2,249 | 9 |
| SART1 | 8,487 | 949 | 9 |
| SEZ6L2 | 6,829 | 763 | 9 |
| VSIG4 | 6,627 | 742 | 9 |
| SEMA3A | 11,888 | 1,334 | 9 |
| Hemoglobin subunit gamma 2/HBG2 | 14,319 | 1,609 | 9 |
| IL-13 | 21,063 | 2,367 | 9 |
| ANGPTL6 | 19,750 | 2,220 | 9 |
| NR3C3 | 16,064 | 1,807 | 9 |
| PEDF | 12,963 | 1,461 | 9 |
| Livin | 11,439 | 1,294 | 9 |
| ABI3BP | 23,308 | 2,640 | 9 |
| Noelin | 14,079 | 1,597 | 9 |
| HTRA1 | 13,158 | 1,493 | 9 |
| FABP5 | 12,634 | 1,435 | 9 |
| Kremen-2 | 14,667 | 1,666 | 9 |
| SCGF | 11,582 | 1,316 | 9 |
| RPS3 | 10,927 | 1,242 | 9 |
| B4GalT1 | 12,904 | 1,467 | 9 |
| ACK1 | 20,317 | 2,316 | 9 |
| APOA1BP | 29,482 | 3,367 | 9 |
| ADAMTS-1 | 9,085 | 1,039 | 9 |
| THOP1 | 8,529 | 977 | 9 |
| IL-7 | 20,807 | 2,390 | 9 |
| TSH | 17,891 | 2,057 | 9 |
| CLIP170-N-t | 32,694 | 3,770 | 9 |
| EphA3 | 17,096 | 1,977 | 9 |
| IL-24 | 26,020 | 3,011 | 9 |
| Ntn1 | 18,855 | 2,187 | 9 |
| Fibrinogen gamma chain/FGG | 16,767 | 1,946 | 9 |
| Rab7a | 7,376 | 859 | 9 |
| SIM2 | 23,540 | 2,740 | 9 |
| Neuropeptide B | 27,884 | 3,248 | 9 |
| HCR/CRAM-A/B | 25,565 | 2,978 | 9 |
| Serpin A12 | 10,345 | 1,206 | 9 |
| OCT3/4 | 10,070 | 1,175 | 9 |
| FER | 35,277 | 4,119 | 9 |
| ITIH3 | 7,889 | 922 | 9 |
| LIN41 | 10,096 | 1,181 | 9 |
| Mer | 10,518 | 1,235 | 9 |
| Hepassocin | 18,043 | 2,119 | 9 |
| PSMD9 | 13,929 | 1,637 | 9 |
| hnRNP A1 | 10,191 | 1,200 | 8 |
| BCHE | 18,257 | 2,157 | 8 |
| Omentin | 13,372 | 1,583 | 8 |
| SF20 | 6,404 | 760 | 8 |
| IRS2 | 31,156 | 3,700 | 8 |
| URB2 | 36,414 | 4,325 | 8 |
| GPX3 | 11,319 | 1,345 | 8 |
| MMP-16/MT3-MMP | 11,312 | 1,345 | 8 |
| GCLC | 29,319 | 3,491 | 8 |
| Cytokeratin 18 | 11,134 | 1,326 | 8 |
| FH | 13,067 | 1,560 | 8 |
| IL-17RC | 22,955 | 2,742 | 8 |
| FGF-5 | 21,876 | 2,618 | 8 |
| GFR alpha-3 | 20,966 | 2,514 | 8 |
| GDI2 | 29,794 | 3,574 | 8 |
| Lamin B2 | 26,055 | 3,126 | 8 |
| ELAVL1 | 25,752 | 3,091 | 8 |
| UGGT | 10,288 | 1,235 | 8 |
| IL-17R | 23,688 | 2,847 | 8 |
| CTACK/CCL27 | 17,666 | 2,127 | 8 |
| DBI | 10,547 | 1,278 | 8 |
| KRTDAP | 19,460 | 2,358 | 8 |
| SAA | 15,444 | 1,872 | 8 |
| MYH2 | 30,261 | 3,670 | 8 |
| CRTAC1 | 20,741 | 2,517 | 8 |
| HEG1 | 17,178 | 2,085 | 8 |
| Annexin A2 | 15,247 | 1,852 | 8 |
| P-selectin | 18,794 | 2,289 | 8 |
| PAI-1 | 14,386 | 1,754 | 8 |
| Factor XIII B | 10,474 | 1,279 | 8 |
| Advillin-N-t | 26,785 | 3,272 | 8 |
| Destrin | 35,838 | 4,380 | 8 |
| LUZP1 | 27,499 | 3,371 | 8 |
| Serpin A10/ZPI | 6,054 | 743 | 8 |
| HSP32 | 9,879 | 1,214 | 8 |
| Kallikrein 5 | 13,551 | 1,669 | 8 |
| OIT3 | 25,744 | 3,187 | 8 |
| Dkk-1 | 14,974 | 1,857 | 8 |
| KRTHA3B | 29,821 | 3,697 | 8 |
| ENO1 + ENO2 + ENO3 | 35,176 | 4,365 | 8 |
| Endocan | 9,302 | 1,155 | 8 |
| MSHa | 16,052 | 1,995 | 8 |
| AKR1B1 | 16,054 | 1,995 | 8 |
| TXK | 19,646 | 2,443 | 8 |
| Pro-Cathepsin B | 8,992 | 1,119 | 8 |
| SOX2 | 12,143 | 1,513 | 8 |
| JAM-A | 8,059 | 1,004 | 8 |
| SERTAD2 | 8,481 | 1,058 | 8 |
| BMP-7 | 19,236 | 2,404 | 8 |
| SPINK1 | 10,560 | 1,321 | 8 |

TABLE 1-continued

| | Composition (Ex. 1) | Comparative Product X | Fold Change |
|---|---|---|---|
| CLIC4 | 33,130 | 4,145 | 8 |
| Human Agrin | 22,863 | 2,863 | 8 |
| Aldolase A | 31,884 | 4,008 | 8 |
| UNC5H4 | 5,974 | 752 | 8 |
| GLP-1 | 16,891 | 2,127 | 8 |
| ERRa | 10,066 | 1,268 | 8 |
| EphB2 | 14,119 | 1,780 | 8 |
| C5b-9 | 19,517 | 2,461 | 8 |
| RNA Polymerase II/POLR2A | 6,750 | 851 | 8 |
| ASPH | 18,420 | 2,323 | 8 |
| ANP | 23,818 | 3,005 | 8 |
| Antithrombin III | 37,705 | 4,765 | 8 |
| Cytokeratin 14 | 14,098 | 1,785 | 8 |
| PYK2 | 13,820 | 1,750 | 8 |
| GRP | 19,342 | 2,451 | 8 |
| AHNAK | 22,341 | 2,833 | 8 |
| hCG alpha | 18,589 | 2,361 | 8 |
| SorLA | 5,910 | 751 | 8 |
| EFTUD2 | 33,177 | 4,216 | 8 |
| Endorphin Beta | 15,399 | 1,961 | 8 |
| Cytokeratin 17 | 33,004 | 4,210 | 8 |
| USP5 | 18,828 | 2,402 | 8 |
| Granzyme A | 9,694 | 1,239 | 8 |
| CA 9 | 10,917 | 1,396 | 8 |
| QPRT | 16,202 | 2,073 | 8 |
| JARID2 | 8,814 | 1,128 | 8 |
| S100A1 | 6,426 | 823 | 8 |
| ADAMTS-L2 | 11,550 | 1,481 | 8 |
| Pleckstrin | 8,101 | 1,039 | 8 |
| RELT/TNFRSF19L | 15,791 | 2,026 | 8 |
| IBP160 | 28,730 | 3,689 | 8 |
| nNOS | 6,642 | 853 | 8 |
| GADD45A | 22,586 | 2,906 | 8 |
| C-peptide | 18,982 | 2,443 | 8 |
| Moesin | 25,077 | 3,230 | 8 |
| Hepcidin | 14,873 | 1,917 | 8 |
| CCR1 | 12,865 | 1,660 | 8 |
| Pro-MMP-7 | 9,106 | 1,178 | 8 |
| CLEC3B | 18,624 | 2,409 | 8 |
| Bax | 15,303 | 1,988 | 8 |
| HSP60 | 11,180 | 1,455 | 8 |
| PARVB | 31,655 | 4,124 | 8 |
| HAI-1 | 10,994 | 1,434 | 8 |
| FoxO1 | 9,442 | 1,233 | 8 |
| SOD1 | 8,497 | 1,111 | 8 |
| APCS | 14,920 | 1,952 | 8 |
| Desmoglein-2 | 10,269 | 1,345 | 8 |
| ProSAAS | 15,134 | 1,983 | 8 |
| ALDH9A1 | 27,565 | 3,613 | 8 |
| EphA4 | 20,368 | 2,670 | 8 |
| C4.4A | 10,539 | 1,392 | 8 |
| Corneodesmosin | 18,481 | 2,445 | 8 |
| MICB | 9,586 | 1,269 | 8 |
| HPD | 22,401 | 2,967 | 8 |
| CAD | 31,643 | 4,193 | 8 |
| HSPA8 | 9,705 | 1,289 | 8 |
| RPS20 | 12,675 | 1,684 | 8 |
| Serpin A7 | 6,137 | 816 | 8 |
| TNK1 | 19,330 | 2,569 | 8 |
| IDUA | 16,868 | 2,242 | 8 |
| SHP-1 | 6,067 | 809 | 8 |
| FGF-11 | 19,712 | 2,632 | 7 |
| Serpin A11 | 5,985 | 800 | 7 |
| TWF2 | 5,194 | 694 | 7 |
| SSEA-1 | 8,759 | 1,172 | 7 |
| Proteasome subunit beta type 2/PSB2 | 30,204 | 4,044 | 7 |
| FLG2 | 28,128 | 3,772 | 7 |
| MIP-1d | 9,655 | 1,297 | 7 |
| p53 | 13,609 | 1,828 | 7 |
| Kallikrein 6 | 10,949 | 1,477 | 7 |
| SHBG | 14,801 | 1,997 | 7 |
| Hemopexin | 10,666 | 1,440 | 7 |
| GRP | 19,335 | 2,611 | 7 |
| PTN | 8,435 | 1,140 | 7 |
| DEFA6 | 32,020 | 4,333 | 7 |
| Talin1 | 6,246 | 846 | 7 |
| NASP | 27,949 | 3,786 | 7 |
| MIP 2 | 18,758 | 2,544 | 7 |
| EIF3S2 | 20,875 | 2,838 | 7 |
| VCP | 6,570 | 895 | 7 |
| Chem R23 | 10,869 | 1,481 | 7 |
| Ceruloplasmin | 23,796 | 3,244 | 7 |
| TFF3 | 9,185 | 1,252 | 7 |
| HN1 | 19,340 | 2,647 | 7 |
| ITIH2 | 6,350 | 871 | 7 |
| APJ | 10,173 | 1,395 | 7 |
| HPRT | 14,540 | 2,001 | 7 |
| RYK | 12,827 | 1,766 | 7 |
| EN2 | 24,726 | 3,414 | 7 |
| ETL | 30,804 | 4,258 | 7 |
| TRKB | 14,269 | 1,976 | 7 |
| GM2A | 33,324 | 4,617 | 7 |
| KRT82 | 20,796 | 2,887 | 7 |
| ERp29 | 30,253 | 4,203 | 7 |
| MMP-13 | 10,277 | 1,429 | 7 |
| ATPB | 27,655 | 3,848 | 7 |
| Cardiotrophin-1/CT-1 | 8,538 | 1,192 | 7 |
| CBP | 18,072 | 2,524 | 7 |
| ZC3H8 | 7,211 | 1,009 | 7 |
| Presenilin 2 | 9,385 | 1,313 | 7 |
| CALML5 | 28,528 | 3,994 | 7 |
| Cystatin B | 15,694 | 2,199 | 7 |
| AR (Amphiregulin) | 10,446 | 1,465 | 7 |
| Presenilin 1 | 13,067 | 1,833 | 7 |
| SART3 | 10,756 | 1,511 | 7 |
| S100A7 | 8,422 | 1,183 | 7 |
| Laminin gamma 1 | 29,790 | 4,187 | 7 |
| LPS | 11,742 | 1,651 | 7 |
| MANF | 7,721 | 1,086 | 7 |
| ASH2L | 31,342 | 4,418 | 7 |
| GLRX1 | 10,292 | 1,452 | 7 |
| NRG3 | 25,315 | 3,582 | 7 |
| LH | 13,511 | 1,916 | 7 |
| ENSA | 28,511 | 4,045 | 7 |
| FRY | 24,131 | 3,424 | 7 |
| DDX3Y | 23,860 | 3,386 | 7 |
| GNB1 | 26,383 | 3,746 | 7 |
| Proteasome 20S alpha 5 | 21,606 | 3,070 | 7 |
| NF1 | 20,770 | 2,954 | 7 |
| Proteasome 26S S5 | 9,597 | 1,365 | 7 |
| TRPM7 | 9,005 | 1,281 | 7 |
| Oxytocin-neurophysin 1/OXT | 15,985 | 2,280 | 7 |
| C1RL | 33,839 | 4,831 | 7 |
| Thymosin b10 | 7,114 | 1,017 | 7 |
| BPIFB1 | 25,654 | 3,666 | 7 |
| VIP Receptor 2 | 11,093 | 1,588 | 7 |
| MFAP4 | 26,647 | 3,826 | 7 |
| Fibrillin 1 | 13,029 | 1,872 | 7 |
| Desmin | 7,344 | 1,056 | 7 |
| PAK7 | 8,754 | 1,260 | 7 |
| CD27/TNFRSF7 | 13,913 | 2,005 | 7 |
| Integrin alpha V | 10,766 | 1,553 | 7 |
| HRSP12 | 9,883 | 1,426 | 7 |
| 14-3-3 zeta | 11,343 | 1,641 | 7 |
| SAA4a | 6,313 | 914 | 7 |
| Syndecan-3 | 9,997 | 1,448 | 7 |
| Cezanne | 29,907 | 4,336 | 7 |
| PEPSINOGEN I | 7,920 | 1,149 | 7 |
| PPARg2 | 12,649 | 1,836 | 7 |
| LTBP4 | 27,354 | 3,987 | 7 |
| GATM - C-terminal | 27,891 | 4,067 | 7 |
| IL-17D | 12,239 | 1,785 | 7 |
| IL-12 p40 | 8,963 | 1,308 | 7 |
| TPA | 9,924 | 1,448 | 7 |
| SOD-3 | 5,873 | 857 | 7 |
| Serpin B6 | 7,301 | 1,068 | 7 |
| Legumain | 13,774 | 2,020 | 7 |
| OBCAM | 7,412 | 1,087 | 7 |
| MCP-2 | 9,181 | 1,347 | 7 |
| CA 19-9 | 18,939 | 2,790 | 7 |
| IL-10 R beta | 8,858 | 1,308 | 7 |

TABLE 1-continued

| | Composition (Ex. 1) | Comparative Product X | Fold Change |
|---|---|---|---|
| Procalcitonin | 11,925 | 1,763 | 7 |
| Thrombin | 9,030 | 1,338 | 7 |
| IL-1 F7/FIL1 zeta | 19,728 | 2,922 | 7 |
| EHD3 | 28,988 | 4,314 | 7 |
| Gelsolin | 13,443 | 2,002 | 7 |
| Calbindin D | 8,301 | 1,238 | 7 |
| FCGBP | 23,372 | 3,486 | 7 |
| CHORDC1 | 34,738 | 5,182 | 7 |
| gamma Catenin | 35,040 | 5,229 | 7 |
| BACE-1 | 7,911 | 1,184 | 7 |
| Calreticulin | 9,708 | 1,453 | 7 |
| EphA8 | 13,606 | 2,038 | 7 |
| Granzyme M | 26,422 | 3,977 | 7 |
| Thrombospondin-2 | 9,902 | 1,491 | 7 |
| Wilms Tumor 1 | 11,351 | 1,713 | 7 |
| FOXN3 | 20,571 | 3,105 | 7 |
| SPEN | 9,143 | 1,381 | 7 |
| VDUP-1 | 11,347 | 1,715 | 7 |
| POMC | 12,842 | 1,942 | 7 |
| Tyk2 | 12,720 | 1,924 | 7 |
| C6 -N-t | 31,458 | 4,763 | 7 |
| PDE1B | 38,835 | 5,883 | 7 |
| TAB182 | 6,300 | 955 | 7 |
| IL-16 | 8,799 | 1,335 | 7 |
| Rbm15 | 8,192 | 1,244 | 7 |
| Cytokeratin 19 | 14,290 | 2,178 | 7 |
| SOD2 | 5,893 | 898 | 7 |
| Eosinophil derived neurotoxin/EDN | 41,850 | 6,384 | 7 |
| Pro-MMP-9 | 11,329 | 1,731 | 7 |
| Lubricin | 28,213 | 4,317 | 7 |
| GMNN | 15,403 | 2,357 | 7 |
| 67LR | 27,082 | 4,151 | 7 |
| TRPS1 | 5,284 | 811 | 7 |
| Dopamine beta Hydroxylase/DBH | 31,998 | 4,911 | 7 |
| ITGB4BP | 14,950 | 2,297 | 7 |
| hnRNP U | 17,186 | 2,643 | 7 |
| IDH1 | 7,095 | 1,092 | 7 |
| SynCAM | 5,281 | 813 | 7 |
| KIAA1967 | 24,888 | 3,829 | 6 |
| CEA | 12,459 | 1,930 | 6 |
| Resistin | 10,650 | 1,650 | 6 |
| Syntaxin 7 | 6,052 | 942 | 6 |
| NET1 | 14,069 | 2,194 | 6 |
| CS | 29,999 | 4,681 | 6 |
| COL19A1 | 32,995 | 5,150 | 6 |
| EphB1 | 15,822 | 2,471 | 6 |
| EPPK1 | 20,109 | 3,142 | 6 |
| C9orf40 | 44,210 | 6,911 | 6 |
| LOX | 27,305 | 4,271 | 6 |
| Lymphotoxin beta R/TNFRSF3 | 9,071 | 1,421 | 6 |
| Neuropeptide Y | 13,823 | 2,170 | 6 |
| p39 | 15,911 | 2,503 | 6 |
| DDT | 12,641 | 1,991 | 6 |
| MCMP2 | 6,641 | 1,050 | 6 |
| GNPTG | 29,877 | 4,727 | 6 |
| Angiopoietin-like 2 | 11,963 | 1,895 | 6 |
| CIP29 | 19,262 | 3,070 | 6 |
| TOP2B | 6,184 | 986 | 6 |
| Corticosteroid-binding globulin | 28,310 | 4,518 | 6 |
| non-muscle Myosin IIA/Myosin | 17,195 | 2,747 | 6 |
| BAFF | 8,887 | 1,420 | 6 |
| C2 | 17,347 | 2,774 | 6 |
| Plxdc2 | 14,314 | 2,293 | 6 |
| FUCA2 | 14,367 | 2,307 | 6 |
| Ube2L3 | 7,345 | 1,180 | 6 |
| DMRN9 | 20,206 | 3,246 | 6 |
| CARHSP1 | 17,206 | 2,767 | 6 |
| GDF9 | 16,088 | 2,597 | 6 |
| SMAC | 9,532 | 1,539 | 6 |
| MAGP-2 | 10,786 | 1,742 | 6 |
| CYTL1 | 22,614 | 3,666 | 6 |
| GARNL1 | 34,998 | 5,680 | 6 |
| EMSY | 13,832 | 2,248 | 6 |
| BMPR-IB/ALK-6 | 11,233 | 1,828 | 6 |
| PCNA | 8,094 | 1,319 | 6 |
| Apex1 | 11,577 | 1,888 | 6 |
| LAMP1 | 8,127 | 1,328 | 6 |
| Filamin A | 19,524 | 3,192 | 6 |
| pro-Glucagon | 12,363 | 2,021 | 6 |
| VEGF R1 | 8,768 | 1,434 | 6 |
| Beta 2M | 15,913 | 2,603 | 6 |
| IL-10 R alpha | 12,254 | 2,007 | 6 |
| ROS | 9,181 | 1,508 | 6 |
| HE4 | 10,852 | 1,785 | 6 |
| ZDHHC18 | 6,742 | 1,110 | 6 |
| ALK | 17,158 | 2,828 | 6 |
| CLPS | 35,213 | 5,809 | 6 |
| RPL17 | 5,916 | 979 | 6 |
| Proteasome subunit beta type 4/PSB4 | 21,023 | 3,482 | 6 |
| Ubiquitin | 7,605 | 1,263 | 6 |
| LCMT2 | 13,775 | 2,290 | 6 |
| Versican isoform V0 | 5,391 | 897 | 6 |
| hnRNP A2B1 | 6,865 | 1,142 | 6 |
| Envoplakin | 29,028 | 4,837 | 6 |
| GPCR GPR116 | 24,956 | 4,167 | 6 |
| LTK | 12,381 | 2,077 | 6 |
| Vasopressin | 10,608 | 1,782 | 6 |
| Vitamin D Receptor | 7,490 | 1,261 | 6 |
| SDF4 | 5,342 | 903 | 6 |
| TRPC1 | 8,755 | 1,486 | 6 |
| CA150 | 25,973 | 4,431 | 6 |
| COTL1 | 36,104 | 6,178 | 6 |
| HMGN2 | 13,897 | 2,383 | 6 |
| NAPRT1 | 26,591 | 4,561 | 6 |
| hGH | 10,223 | 1,755 | 6 |
| SMA | 7,741 | 1,331 | 6 |
| Glutamyl hydrolase gamma/CGH | 27,350 | 4,730 | 6 |
| CCL14/HCC-1/HCC-3 | 14,063 | 2,437 | 6 |
| GRHPR | 30,827 | 5,343 | 6 |
| Prosaposin | 25,314 | 4,389 | 6 |
| COLEC10 | 32,916 | 5,716 | 6 |
| TROPONIN I | 8,726 | 1,518 | 6 |
| MDH2 | 31,056 | 5,402 | 6 |
| PSP | 8,033 | 1,398 | 6 |
| Ghrelin | 14,501 | 2,536 | 6 |
| MTUS1 | 11,090 | 1,946 | 6 |
| Netrin G2 | 13,883 | 2,440 | 6 |
| ALS | 30,187 | 5,306 | 6 |
| Notch-2 ICD | 6,616 | 1,166 | 6 |
| FBP 38 | 23,760 | 4,197 | 6 |
| FAK | 12,914 | 2,287 | 6 |
| Intergrin a6 | 6,580 | 1,169 | 6 |
| DAN | 6,687 | 1,191 | 6 |
| BLC/BCA-1/CXCL13 | 22,344 | 3,987 | 6 |
| Troponin C | 16,335 | 2,924 | 6 |
| PF4V1 | 6,813 | 1,220 | 6 |
| G3BP | 27,679 | 4,971 | 6 |
| ADAMDEC1 | 38,263 | 6,875 | 6 |
| CCDC126 | 38,542 | 6,933 | 6 |
| ACACA | 12,477 | 2,246 | 6 |
| EphA5 | 17,306 | 3,129 | 6 |
| Hck | 27,551 | 4,990 | 6 |
| NRG2 | 20,529 | 3,721 | 6 |
| hnRNP C1 + C2 | 15,767 | 2,863 | 6 |
| MYL3 | 16,977 | 3,084 | 6 |
| Peroxiredoxin 5 | 8,702 | 1,585 | 5 |
| Vitamin K-dependent protein S | 11,877 | 2,166 | 5 |
| PTK 7 | 6,270 | 1,146 | 5 |
| UQCRH | 6,473 | 1,187 | 5 |
| SYK | 9,040 | 1,660 | 5 |
| CART | 11,458 | 2,105 | 5 |
| Serpin A4 | 10,983 | 2,020 | 5 |
| TXNDC4 | 5,396 | 993 | 5 |
| Apo (a) | 26,621 | 4,897 | 5 |
| APM2 | 23,123 | 4,267 | 5 |
| ITGB5 | 7,511 | 1,387 | 5 |
| 14-3-3 gamma | 21,592 | 3,992 | 5 |
| Dermcidin | 32,907 | 6,087 | 5 |
| AKR7A2 | 22,592 | 4,183 | 5 |
| ORP150 | 43,150 | 7,991 | 5 |

TABLE 1-continued

| | Composition (Ex. 1) | Comparative Product X | Fold Change |
|---|---|---|---|
| VWF | 11,616 | 2,159 | 5 |
| Cytokeratin 4 | 34,318 | 6,379 | 5 |
| GPI | 10,744 | 1,999 | 5 |
| CCDC25 | 12,241 | 2,287 | 5 |
| MIP-1b | 21,425 | 4,003 | 5 |
| Midkine | 10,492 | 3,966 | 5 |
| DSPG3 | 10,258 | 1,924 | 5 |
| AKAP9 | 23,873 | 4,479 | 5 |
| BAD | 28,643 | 5,383 | 5 |
| Apolipoprotein L 2 | 20,390 | 3,838 | 5 |
| LMW-PTP/ACP1 | 6,299 | 1,187 | 5 |
| EFEMP2 | 34,688 | 6,544 | 5 |
| HTRA2 | 11,121 | 2,106 | 5 |
| Kallikrein 8 | 7,563 | 1,434 | 5 |
| KLF4 | 8,885 | 1,695 | 5 |
| EMILIN1 | 20,810 | 3,977 | 5 |
| XEDAR | 13,419 | 2,566 | 5 |
| Aconitase 1 | 36,013 | 6,906 | 5 |
| CHI3L1 | 14,823 | 2,844 | 5 |
| hCGb | 13,698 | 2,632 | 5 |
| DARS2 | 20,993 | 4,055 | 5 |
| UPB1 | 5,689 | 1,099 | 5 |
| ERp72 | 33,016 | 6,381 | 5 |
| HIP1R | 14,640 | 2,832 | 5 |
| BD-1 | 31,963 | 6,213 | 5 |
| Ctip2 | 32,968 | 6,411 | 5 |
| D4 GDI | 35,486 | 6,902 | 5 |
| CCK | 11,685 | 2,275 | 5 |
| PCPE-1 | 7,362 | 1,435 | 5 |
| CRP | 12,296 | 2,398 | 5 |
| Cux2 | 30,730 | 5,993 | 5 |
| MAGI2 | 6,121 | 1,195 | 5 |
| MyBPC3 | 7,566 | 1,481 | 5 |
| ARP2/3 | 32,580 | 6,412 | 5 |
| EEF2 | 28,328 | 5,578 | 5 |
| Kallikrein 2 | 12,048 | 2,376 | 5 |
| Tryptophanyl | 6,318 | 1,246 | 5 |
| LTA4H | 6,633 | 1,308 | 5 |
| PGAM1 | 11,278 | 2,225 | 5 |
| PSMA2 | 6,312 | 1,250 | 5 |
| alpha 1,2 Mannosidase IA/MAN1A1 | 24,257 | 4,805 | 5 |
| Cytokeratin 16 | 31,201 | 6,214 | 5 |
| SRMS | 13,275 | 2,644 | 5 |
| GDA | 10,897 | 2,179 | 5 |
| C3orf75 | 30,816 | 6,165 | 5 |
| FASTKD5 | 22,699 | 4,543 | 5 |
| CETP | 10,711 | 2,147 | 5 |
| DPP3 | 26,870 | 5,391 | 5 |
| ARFGEF3 | 27,311 | 5,495 | 5 |
| Calpain 1 | 30,366 | 6,110 | 5 |
| Csk | 14,867 | 3,010 | 5 |
| Cytokeratin 15 | 15,647 | 3,170 | 5 |
| DEFA1/3 | 10,344 | 2,102 | 5 |
| Nucleobindin 1/NUCB1 | 7,302 | 1,487 | 5 |
| Factor XII | 22,247 | 4,543 | 5 |
| ENO1 | 33,840 | 6,948 | 5 |
| BRSK1 | 34,652 | 7,193 | 5 |
| fast skeletal Myosin | 25,640 | 5,324 | 5 |
| Factor V | 19,277 | 4,008 | 5 |
| ASXL1 | 36,962 | 7,702 | 5 |
| mGLUR5 | 6,658 | 1,391 | 5 |
| Cytokeratin 10 | 31,077 | 6,498 | 5 |
| ESR1 | 14,873 | 3,114 | 5 |
| beta III Tubulin/CUBB3 | 30,266 | 6,360 | 5 |
| LDHB | 9,176 | 1,935 | 5 |
| TRPC6 | 7,283 | 1,538 | 5 |
| Serotonin | 9,128 | 1,932 | 5 |
| p23 | 17,449 | 3,697 | 5 |
| CPA1 | 12,799 | 2,725 | 5 |
| Ahsp | 31,108 | 6,630 | 5 |
| Kilon | 6,974 | 1,487 | 5 |
| Protein Z | 9,006 | 1,924 | 5 |
| Calpastatin | 14,611 | 3,123 | 5 |
| BIN2 | 32,472 | 6,951 | 5 |
| EphB3 | 29,870 | 6,398 | 5 |
| MFI2 | 6,428 | 1,380 | 5 |
| Cytokeratin 3 | 30,988 | 6,656 | 5 |
| EPHX2 | 18,886 | 4,066 | 5 |
| Cytokeratin 5 | 30,686 | 6,633 | 5 |
| PCAF | 15,372 | 3,331 | 5 |
| ASK1 | 32,379 | 7,036 | 5 |
| CLTA | 30,607 | 6,675 | 5 |
| CNDP1 | 11,231 | 2,453 | 5 |
| MPCA | 6,778 | 1,481 | 5 |
| Mimecan | 9,143 | 1,998 | 5 |
| HSC70 | 7,026 | 1,536 | 5 |
| Fumarylacetoacetate hydrolase/FAH | 10,349 | 2,263 | 5 |
| GHRF | 13,863 | 3,033 | 5 |
| ADH1B | 30,832 | 6,758 | 5 |
| ITIH1 | 9,129 | 2,006 | 5 |
| DNER | 15,966 | 3,513 | 5 |
| MBP | 6,419 | 1,419 | 5 |
| Apelin | 15,048 | 3,328 | 5 |
| LYPA1 | 17,405 | 3,861 | 5 |
| CACNB4 | 11,336 | 2,516 | 5 |
| BPGM | 37,917 | 8,508 | 4 |
| Cadherin 22 | 23,589 | 5,300 | 4 |
| HIBADH | 14,795 | 3,332 | 4 |
| VGF | 8,374 | 1,891 | 4 |
| ABAT | 33,350 | 7,579 | 4 |
| G0/G1switch 2 | 24,528 | 5,586 | 4 |
| Ephrin B2 | 12,903 | 2,939 | 4 |
| SCG3 | 6,856 | 1,563 | 4 |
| ERAB | 27,030 | 6,165 | 4 |
| CHREBP | 49,341 | 11,274 | 4 |
| Hemoglobin subunit delta/HBD | 15,276 | 3,496 | 4 |
| C1qTNF1 | 10,183 | 2,332 | 4 |
| Haptoglobin | 25,036 | 5,735 | 4 |
| D-Dimer | 22,417 | 5,135 | 4 |
| Calmodulin | 25,018 | 5,735 | 4 |
| EphA7 | 20,756 | 4,759 | 4 |
| alpha Tubulin | 25,139 | 5,767 | 4 |
| PRSS23 | 28,200 | 6,493 | 4 |
| Cytokeratin 20 | 35,636 | 8,215 | 4 |
| Tec | 8,887 | 2,056 | 4 |
| Coronin 3 | 18,867 | 4,368 | 4 |
| TIM-4 | 6,159 | 1,431 | 4 |
| CD 163 | 22,691 | 5,284 | 4 |
| MGP | 4,905 | 1,159 | 4 |
| Aspartate Aminotransferase/AST | 30,603 | 7,280 | 4 |
| MYH6 | 7,894 | 1,879 | 4 |
| Karyopherin beta 1 | 7,061 | 1,685 | 4 |
| DR3/TNFRSF25 | 8,186 | 1,955 | 4 |
| CECR1 | 17,760 | 4,255 | 4 |
| ACTBL2 | 32,611 | 7,816 | 4 |
| CNN2 | 32,734 | 7,851 | 4 |
| BMPR-IA/ALK-3 | 8,288 | 2,003 | 4 |
| BMP-4 | 16,296 | 3,954 | 4 |
| GDI1 | 30,857 | 7,512 | 4 |
| TYRO10 | 17,386 | 4,242 | 4 |
| TAF4 | 4,514 | 1,105 | 4 |
| hnRNP M1-M4 | 30,864 | 7,596 | 4 |
| ZAP70 | 13,752 | 3,393 | 4 |
| Stathmin 1 | 7,220 | 1,797 | 4 |
| HLA-C | 20,846 | 5,197 | 4 |
| Argininosuccinate Lyase/ASL | 20,255 | 5,052 | 4 |
| Integrin beta 6 | 6,793 | 1,695 | 4 |
| TRF 2 | 6,789 | 1,698 | 4 |
| Chromogranin C | 33,216 | 8,359 | 4 |
| CLEC14A | 18,246 | 4,600 | 4 |
| ENPP2 | 20,082 | 5,066 | 4 |
| Itk | 22,803 | 5,775 | 4 |
| MCM | 4,756 | 1,206 | 4 |
| Bcl-w | 14,284 | 3,625 | 4 |
| PI 3Kinase p85 beta | 17,592 | 4,477 | 4 |
| PTPRD | 14,394 | 3,667 | 4 |
| LEKTI/SPINK5 | 6,175 | 1,582 | 4 |
| Lyn | 14,424 | 3,703 | 4 |
| Fen 1 | 12,232 | 3,143 | 4 |
| Factor IX | 10,434 | 2,690 | 4 |

TABLE 1-continued

| | Composition (Ex. 1) | Comparative Product X | Fold Change |
|---|---|---|---|
| CRMP2 | 32,732 | 8,486 | 4 |
| EPB41 | 20,157 | 5,294 | 4 |
| MINA | 20,296 | 5,347 | 4 |
| PCBP1 | 6,569 | 1,731 | 4 |
| Lck | 14,313 | 3,795 | 4 |
| KHSRP | 23,444 | 6,216 | 4 |
| DAK | 20,065 | 5,326 | 4 |
| IL-1 R4/ST2 | 7,423 | 1,985 | 4 |
| Histone H2A.Z | 11,165 | 2,985 | 4 |
| ESD | 28,989 | 7,860 | 4 |
| CO4A2 | 23,998 | 6,563 | 4 |
| ZAG | 13,214 | 3,629 | 4 |
| C8G | 38,929 | 10,740 | 4 |
| HABP2 | 8,976 | 2,489 | 4 |
| Histone H1.2 | 12,303 | 3,442 | 4 |
| ACAA2 | 29,429 | 8,253 | 4 |
| Cytokeratin 13 | 29,943 | 8,407 | 4 |
| Bassoon | 26,516 | 7,480 | 4 |
| Alpha 1 Microglobulin | 8,964 | 2,531 | 4 |
| COL9A3 | 29,929 | 8,451 | 4 |
| BAF57 | 8,681 | 2,456 | 4 |
| PTH | 12,981 | 3,684 | 4 |
| ART3 | 31,673 | 9,030 | 4 |
| ADAMTS-4 | 20,840 | 6,073 | 3 |
| EEF1G | 31,761 | 9,274 | 3 |
| Androgen Receptor | 15,275 | 4,504 | 3 |
| MATK | 19,069 | 5,658 | 3 |
| KCC3 | 7,749 | 2,301 | 3 |
| Eps 15 | 21,734 | 6,459 | 3 |
| Non-muscle Actin/Actin | 5,608 | 1,688 | 3 |
| Chromogranin A | 10,162 | 3,063 | 3 |
| GST | 11,951 | 3,608 | 3 |
| FBP2 | 27,047 | 8,250 | 3 |
| BID | 16,213 | 4,999 | 3 |
| MMP-19 | 9,345 | 2,921 | 3 |
| MDH1 | 31,448 | 9,851 | 3 |
| Selenoprotein P | 12,514 | 3,929 | 3 |
| Arp2 | 28,472 | 8,970 | 3 |
| KMT2B | 19,797 | 6,293 | 3 |
| CPS1 | 29,253 | 9,391 | 3 |
| Calretinin | 15,726 | 5,049 | 3 |
| Apolipoprotein F | 31,493 | 10,152 | 3 |
| ACAA1 | 53,682 | 17,313 | 3 |
| HSP27 | 28,256 | 9,263 | 3 |
| CEP57 | 41,348 | 13,618 | 3 |
| IGFBP-1 | 28,402 | 9,409 | 3 |
| PCMT1 | 7,839 | 2,600 | 3 |
| BPIL1 | 27,615 | 9,174 | 3 |
| eIF4A1-N-t | 28,241 | 9,390 | 3 |
| Alpha Lactalbumin | 24,829 | 8,276 | 3 |
| PDGF R alpha | 10,413 | 3,483 | 3 |
| CENPF | 45,200 | 15,231 | 3 |
| Creatine Kinase MM/CKMM | 15,837 | 5,352 | 3 |
| Asialoglycoprotein Receptor 2/ASGR2 | 34,453 | 11,677 | 3 |
| Phosphoserine Aminotransferase/PSAT1 | 7,504 | 2,555 | 3 |
| Gastrin | 15,286 | 5,209 | 3 |
| Aldolase C | 30,554 | 10,440 | 3 |
| CAPZA1 | 33,615 | 11,534 | 3 |
| IDH3A | 11,628 | 3,991 | 3 |
| Keratin 38 | 28,863 | 10,019 | 3 |
| GOT2 | 19,183 | 6,788 | 3 |
| Alpha Fodrin | 48,914 | 17,520 | 3 |
| GLUD1 | 28,145 | 10,127 | 3 |
| D6 | 93,749 | 33,817 | 3 |
| GBE1 | 16,346 | 5,928 | 3 |
| Krt73 | 26,375 | 9,621 | 3 |
| E1 Ubiquitin Activating Enzyme/UBA1 | 31,440 | 11,579 | 3 |
| BCOR | 29,629 | 10,925 | 3 |
| CPN1 | 37,920 | 13,989 | 3 |
| PTEN | 7,858 | 2,919 | 3 |
| Cathelicidin | 52,356 | 19,480 | 3 |
| GPLD1 | 11,925 | 4,497 | 3 |
| MCM5 | 8,415 | 3,174 | 3 |
| NQO2 | 26,040 | 9,966 | 3 |
| GCDFP 15 | 17,450 | 6,716 | 3 |
| RET | 12,212 | 4,718 | 3 |
| A1BG | 21,781 | 8,423 | 3 |
| HEXA | 6,928 | 2,685 | 3 |
| Acetyl-CoA acetyltransferase/ACAA | 36,534 | 14,302 | 3 |
| Glucosidase 2 subunit beta/PRKCSH | 25,405 | 9,958 | 3 |
| KRT72 | 7,297 | 2,910 | 3 |
| KIF5B | 21,407 | 8,540 | 3 |
| PPP2R1B | 39,140 | 15,649 | 3 |
| gamma-Thrombin | 4,713 | 1,886 | 2 |
| Alcohol Dehydrogenase/ADH | 24,554 | 9,882 | 2 |
| EHD1 | 19,101 | 7,828 | 2 |
| COPS8 | 35,389 | 14,607 | 2 |
| FRK | 16,299 | 6,772 | 2 |
| IGF2BP2 | 14,289 | 6,058 | 2 |
| alpha Glucosidase II | 27,129 | 11,668 | 2 |
| KSR1 | 25,990 | 11,270 | 2 |
| CPN2 | 27,165 | 11,812 | 2 |
| LAG-3 | 9,531 | 4,216 | 2 |
| AK2 | 28,573 | 12,715 | 2 |
| PEPD | 31,127 | 13,886 | 2 |
| ADAS | 39,014 | 17,785 | 2 |
| Creatinine | 8,593 | 3,935 | 2 |
| COL4A3 | 60,917 | 27,992 | 2 |
| LMAN2 | 7,032 | 3,237 | 2 |
| RIP1 | 5,730 | 2,655 | 2 |
| Cytokeratin 9 | 29,530 | 13,696 | 2 |
| SPARCL1 | 10,411 | 4,868 | 2 |
| Filamin C | 22,129 | 10,356 | 2 |
| MIP-3 beta | 12,465 | 5,876 | 2 |
| KRT85 - N-terminal | 8,000 | 3,771 | 2 |
| LAD | 26,771 | 12,673 | 2 |
| GOLPH4 | 20,468 | 9,730 | 2 |
| Cytochrome b5 | 34,127 | 16,283 | 2 |
| ADH4 | 44,681 | 21,658 | 2 |
| ARPC2 | 37,369 | 18,137 | 2 |
| LYRIC | 5,750 | 2,801 | 2 |
| Angiopoietin-1 | 35,269 | 17,338 | 2 |
| FDPS | 45,949 | 22,810 | 2 |
| Apolipoprotein L 1 | 28,753 | 14,526 | 2 |
| DPEP2 | 19,516 | 10,038 | 2 |
| Vitamin D-BP | 11,041 | 5,761 | 2 |
| Ankrd26 | 19,308 | 10,115 | 2 |
| APA | 37,339 | 19,696 | 2 |
| ArgRS | 39,318 | 20,781 | 2 |
| Fibrinopeptide B | 24,202 | 12,927 | 2 |
| LAP3 | 26,573 | 14,350 | 2 |
| Ihh | 5,828 | 3,148 | 2 |
| ALDH16A1 | 33,383 | 18,088 | 2 |
| IQGAP1 | 24,104 | 13,223 | 2 |
| LASP1 | 5,886 | 3,255 | 2 |
| Integrin b1 | 12,457 | 7,147 | 2 |
| DPPI | 19,671 | 11,340 | 2 |
| TRAP220 | 16,448 | 9,486 | 2 |
| Glutathione Synthetase/GSS | 21,802 | 12,769 | 2 |
| BASP1 | 45,346 | 27,835 | 2 |
| Btk | 29,078 | 18,010 | 2 |
| ATP5A | 40,930 | 26,042 | 2 |
| Keratin 36 | 6,707 | 4,273 | 2 |
| ECHS1 | 29,681 | 18,911 | 2 |
| Desmocollin 1 | 37,169 | 24,297 | 2 |
| DRIL1 | 25,260 | 16,570 | 2 |
| LTF | 14,762 | 9,845 | 1 |
| GART | 27,356 | 18,249 | 1 |
| Contactin-3 | 30,249 | 20,237 | 1 |
| S100 A8/A9 | 15,811 | 10,676 | 1 |
| Arp3 | 38,823 | 26,920 | 1 |
| GOLPH2 | 36,285 | 25,479 | 1 |
| ISOC2 | 23,216 | 17,693 | 1 |
| alpha Actinin 4 | 31,888 | 25,074 | 1 |
| GREMLIN | 22,410 | 17,965 | 1 |
| Frizzled 8 | 26,113 | 21,577 | 1 |
| LAM b1 | 55,386 | 46,638 | 1 |

TABLE 1-continued

|  | Composition (Ex. 1) | Comparative Product X | Fold Change |
|---|---|---|---|
| PTHLP | 14,764 | 12,907 | 1 |
| LAF4 | 25,113 | 22,304 | 1 |
| MMP-20 | 21,745 | 21,591 | 1 |
| CAP1 | 54,249 | 57,481 | 1 |
| Fc gamma RIIIB | 18,108 | 19,332 | 1 |
| BAI-1 | 12,679 | 13,710 | 1 |
| Glypican 5 | 16,588 | 19,328 | 1 |
| Aspartyl Aminopeptidase/DNPEP | 35,637 | 43,824 | 1 |
| IQGAP2 | 30,386 | 39,526 | 1 |
| ALAD | 34,765 | 54,447 | 1 |
| ApoA4 | 28,211 | 50,991 | 1 |
| KIAA0319L | 10,004 | 18,789 | 1 |
| Calcitonin | 5,629 | 10,804 | 1 |
| Neurogranin | 19,438 | 75,993 | 0 |
| HRG-alpha | 15,320 | 278,947 | 0 |

What is claimed is:

1. A method for preparing an exosome composition, the method comprising:
   (a) culturing mesenchymal stem cells on one or more microcarriers in a culture media;
   (b) collecting the culture media as a first fraction and collecting the mesenchymal stem cells in a second fraction, the second fraction further comprising exosomes, extracellular matrix, and fragments thereof, and at least one microcarrier;
   (c) adding a solution to the second fraction;
   (d) filtering the second fraction through a first section of a tangential flow filtration system to obtain a first permeate comprising the exosomes and the extracellular matrix and fragments thereof;
   (e) filtering the first permeate through a second section of the tangential flow filtration system to generate a second permeate comprising exosomes and at least one extracellular matrix component;
   (f) combining the second permeate with the first fraction collected in step (b) to form a third fraction; and
   (g) collecting the third fraction as the exosome composition.

2. The method of claim 1, wherein step (a) comprises culturing the mesenchymal stem cells for a time sufficient to generate a conditioned media and step (b) comprises collecting the conditioned media as the first fraction.

3. The method of claim 1, wherein the method does not comprise ultra-centrifugation.

4. The method of claim 1, wherein the first section of the tangential flow filtration system comprises a filter having a pore size of about 0.5 to 1 micron and/or the second section of the tangential flow filtration system comprises a filter having a pore size of about 50 kD to about 500 kD.

5. The method of claim 1, further comprising obtaining the mesenchymal stem cells from a tissue sample.

6. The method of claim 5, wherein the tissue sample comprises umbilical cord blood, placental tissue, umbilical cord tissue, adipose tissue, bone marrow, skin, ocular tissue, or teeth.

7. The method of claim 1, further comprising filtering the third fraction through a third section of the tangential flow filtration system to form a third permeate and collecting the third permeate as the exosome composition.

8. The method of claim 7, wherein the third section of the tangential flow filtration system comprises a filter having a pore size of about 200 to 800 kD.

9. The method of claim 7, further comprising filtering the third permeate through a fourth section of the tangential flow filtration system to form a fourth permeate and collecting the fourth permeate as the exosome composition.

10. The method of claim 9, wherein the fourth section of the tangential flow filtration system comprises a filter having a pore size of about 50 to 100 kD.

11. The method of claim 1, wherein the solution added in step (c) comprises a lysis solution.

12. A method of preparing an MSC composition and an exosome composition, the method comprising
   (a) culturing mesenchymal stem cells on one or more microcarriers in a culture media;
   (b) collecting the culture media as a first fraction and collecting the mesenchymal stem cells as a second fraction, the second fraction further comprising exosomes, extracellular matrix and fragments thereof, and at least one microcarrier;
   (c) adding a solution to the second fraction;
   (d) filtering the second fraction through a first section of a tangential flow filtration system to obtain a first permeate comprising the exosomes, the extracellular matrix colonies and fragments thereof and a retentate comprising the mesenchymal stem cells;
   (e) collecting the retentate as the MSC composition;
   (f) filtering the first permeate through a second section of the tangential flow filtration system to generate a second permeate comprising exosomes and at least one extracellular matrix component;
   (g) combining the second permeate with the first fraction collected in step (b) to generate a third fraction; and
   (h) collecting the third fraction as the exosome composition.

13. The method of claim 12, wherein the solution added in step (c) comprises a lysis solution.

* * * * *